United States Patent
Lee et al.

(10) Patent No.: US 9,574,173 B2
(45) Date of Patent: Feb. 21, 2017

(54) GENERATION OF NEURAL STEM CELLS FROM HUMAN TROPHOBLAST STEM CELLS

(75) Inventors: Jau-Nan Lee, Kaohsiung (TW); Tony Tung-Ying Lee, Albuquerque, NM (US); Yuta Lee, Kaohsiung (TW); Eing-Mei Tsai, Kaohsiung (TW)

(73) Assignee: ACCELERATED BIOSCIENCES CORP., Manhattan Beach, CA (US)

( * ) Notice: Subject to any disclaimer, the term of this patent is extended or adjusted under 35 U.S.C. 154(b) by 639 days.

(21) Appl. No.: 13/296,876

(22) Filed: Nov. 15, 2011

(65) Prior Publication Data

US 2012/0135878 A1  May 31, 2012

Related U.S. Application Data

(60) Provisional application No. 61/413,892, filed on Nov. 15, 2010, provisional application No. 61/434,790, filed on Jan. 20, 2011.

(51) Int. Cl.
| | |
|---|---|
| *C12N 5/0735* | (2010.01) |
| *C12N 5/079* | (2010.01) |
| *C12Q 1/68* | (2006.01) |
| *G01N 33/50* | (2006.01) |
| *C12N 5/073* | (2010.01) |

(52) U.S. Cl.
CPC .......... *C12N 5/0605* (2013.01); *C12N 5/0618* (2013.01); *C12Q 1/6881* (2013.01); *G01N 33/5073* (2013.01); *C12N 2501/38* (2013.01); *C12N 2501/60* (2013.01); *C12N 2506/025* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 5,384,261 | A | 1/1995 | Winkler et al. |
| 5,445,934 | A | 8/1995 | Fodor et al. |
| 5,677,195 | A | 10/1997 | Winkler et al. |
| 5,708,153 | A | 1/1998 | Dower et al. |
| 5,744,305 | A | 4/1998 | Fodor et al. |
| 5,770,358 | A | 6/1998 | Dower et al. |
| 5,770,722 | A | 6/1998 | Lockhart et al. |
| 5,789,162 | A | 8/1998 | Dower et al. |
| 5,800,992 | A | 9/1998 | Fodor et al. |
| 5,854,033 | A | 12/1998 | Lizardi |
| 5,874,219 | A | 2/1999 | Rava et al. |
| 6,020,135 | A | 2/2000 | Levine et al. |
| 6,033,860 | A | 3/2000 | Lockhart et al. |
| 6,040,138 | A | 3/2000 | Lockhart et al. |
| 6,040,193 | A | 3/2000 | Winkler et al. |
| 6,330,349 | B1 | 12/2001 | Hays et al. |
| 6,344,316 | B1 | 2/2002 | Lockhart et al. |
| 6,630,349 | B1 | 10/2003 | Rossant et al. |
| 7,432,104 | B2 | 10/2008 | Mitalipova et al. |
| 7,510,876 | B2 | 3/2009 | D'Amour et al. |
| 7,534,608 | B2 | 5/2009 | Martinson et al. |
| 7,541,185 | B2 | 6/2009 | D'Amour et al. |
| 7,642,091 | B2 | 1/2010 | Lee et al. |
| 7,695,963 | B2 | 4/2010 | Agulnick et al. |
| 7,695,965 | B2 | 4/2010 | Martinson et al. |
| 7,704,738 | B2 | 4/2010 | D'Amour et al. |
| 7,892,534 | B2 | 2/2011 | Lee et al. |
| 8,071,562 | B2 | 12/2011 | Bader et al. |
| 8,163,553 | B2 | 4/2012 | Lee et al. |
| 8,247,229 | B2 | 8/2012 | Odorico et al. |
| 8,497,120 | B2 | 7/2013 | Lee et al. |
| 8,557,580 | B2 | 10/2013 | Daigh et al. |
| 8,691,274 | B2 | 4/2014 | Xu et al. |
| 8,691,974 | B2 | 4/2014 | Gatenholm et al. |
| 9,335,322 | B2 | 5/2016 | Lee et al. |
| 2003/0104616 | A1 | 6/2003 | Parikh et al. |
| 2004/0072288 | A1 | 4/2004 | Collas et al. |
| 2006/0062769 | A1 | 3/2006 | Habener et al. |
| 2006/0211110 | A1 | 9/2006 | Lee et al. |
| 2007/0026405 | A1 | 2/2007 | Alitalo et al. |
| 2007/0128174 | A1 | 6/2007 | Kleinsek et al. |
| 2009/0087417 | A1 | 4/2009 | Arenas et al. |
| 2009/0208466 | A1 | 8/2009 | Yoo et al. |
| 2009/0263361 | A1 | 10/2009 | Lee et al. |
| 2009/0263849 | A1 | 10/2009 | Sun et al. |
| 2011/0136162 | A1 | 6/2011 | Sun et al. |
| 2011/0151560 | A1 | 6/2011 | Xu |

(Continued)

FOREIGN PATENT DOCUMENTS

| | | |
|---|---|---|
| EP | 2233566 A1 | 9/2010 |
| EP | 2679669 A1 | 1/2014 |

(Continued)

OTHER PUBLICATIONS

Portmann-Lanz (Portmann-Lanz et al., Placental mesenchymal stem cells as potential autologous graft for pre- and perinatal neuroregeneration; Am J Obstetrics and Gynecology, vol. 194, 664-673, 2006).*
von Gunten (von Gunten et al., Sialic acid binding immunoglobulin-like lectins may regulate innate immune responses by modulating the life span of granulocytes; FASEB Journal, vol. 20, pp. 601-605, 2006).*
Phillips et al., Cdx2 as a Marker of Epithelial Intestinal Differentiation in the Esophagus; Am J Surg Pathol, vol. 27, No. 11, pp. 1442-1447, 2003.*
Chiba et al., Noggin and basic FGF were implicated in forebrain fate and caudal fate, respectively, of the neural tube-like structures emerging in mouse ES cell culture Exp Brain Res, vol. 163, pp. 86-99, 2005.*
Hori et al., Neural Progenitor Cells Lack Immunogenicity and Resist Destruction as Allografts; Stem Cells, vol. 21, pp. 405-416, 2003.*
Maden, M. Retinoic acid in the development, regeneration and maintenance of the nervous system; Nature Reviews, vol. 8, pp. 755-765, 2007.*
Adjaye, et al. Primary differentiation in the human blastocyst: comparative molecular portraits of inner cell mass and trophectoderm cells. Stem Cells. Nov.-Dec. 2005;23(10):1514-25. Epub Aug. 4, 2005.
Anderson. Human gene therapy. Science. May 8, 1992;256(5058):808-13.
Anneren, et al. The Srs family of tyrosine kinases is important for embryonic stem cell self-renewal. J Biol Chem. Jul. 23, 2004;279(30):31590-8. Epub May 17, 2004.

(Continued)

*Primary Examiner* — Addison D Ault
(74) *Attorney, Agent, or Firm* — Wilson Sonsini Goodrich & Rosati

(57) ABSTRACT

Provided herein are isolated neural stem cells. Also provided are methods for treatment of neurodegenerative diseases using suitable preparations comprising the isolated neural stem cells.

1 Claim, 34 Drawing Sheets

(56) References Cited

U.S. PATENT DOCUMENTS

| | | | |
|---|---|---|---|
| 2011/0165682 A1 | 7/2011 | Lee et al. | |
| 2011/0188728 A1* | 8/2011 | Sammak et al. | 382/133 |
| 2011/0250688 A1 | 10/2011 | Hasan | |
| 2012/0089238 A1 | 4/2012 | Kang et al. | |
| 2012/0116568 A1 | 5/2012 | Murphy et al. | |
| 2012/0148550 A1 | 6/2012 | Brodie et al. | |
| 2012/0190078 A1 | 7/2012 | Gatenholm et al. | |
| 2012/0190730 A1 | 7/2012 | Michael | |
| 2012/0277111 A1 | 11/2012 | Crabtree et al. | |
| 2012/0328579 A1 | 12/2012 | Lee et al. | |
| 2013/0004469 A1 | 1/2013 | Glazier et al. | |
| 2013/0017564 A1 | 1/2013 | Guillemot et al. | |
| 2013/0028872 A1 | 1/2013 | Bone et al. | |
| 2013/0164339 A1 | 6/2013 | Murphy et al. | |
| 2013/0259836 A1 | 10/2013 | Lee et al. | |
| 2013/0304233 A1 | 11/2013 | Dean et al. | |
| 2013/0337458 A1 | 12/2013 | Lee et al. | |
| 2014/0012407 A1 | 1/2014 | Murphy et al. | |
| 2014/0052285 A1 | 2/2014 | Butcher et al. | |
| 2014/0093932 A1 | 4/2014 | Murphy et al. | |
| 2014/0099709 A1 | 4/2014 | Presnell et al. | |
| 2014/0170118 A1 | 6/2014 | Lee et al. | |
| 2016/0051592 A1 | 2/2016 | Lee et al. | |

FOREIGN PATENT DOCUMENTS

| | | |
|---|---|---|
| JP | 2009533056 A | 9/2009 |
| WO | WO-03050249 B1 | 5/2004 |
| WO | WO-2005030961 A1 | 4/2005 |
| WO | WO 2006/091766 A2 | 8/2006 |
| WO | WO-2008002662 A2 | 1/2008 |
| WO | WO 2010/096496 A2 | 8/2010 |
| WO | WO 2011/050476 A1 | 5/2011 |
| WO | WO 2011/054100 A1 | 5/2011 |
| WO | WO 2012/068170 A2 | 5/2012 |
| WO | WO-2012070014 A2 | 5/2012 |
| WO | WO-2012104731 A2 | 8/2012 |
| WO | WO-2012122105 A1 | 9/2012 |
| WO | WO-2013040087 A2 | 3/2013 |
| WO | WO-2013181375 A1 | 12/2013 |
| WO | WO-2013189521 A1 | 12/2013 |
| WO | WO-2014039427 A1 | 3/2014 |
| WO | WO 2014/085493 A1 | 6/2014 |

OTHER PUBLICATIONS

Arnit, et al. Clonally Derived Human Embryonic Stem Cell Lines Maintain Pluripotency and Proliferative Potential for Prolonged Periods of Culture, Developmental Biology 227,271-278 (2000).
Bain, et al. Embryonic stem cells express neuronal properties in vitro. Dev. Biol. 1995; 168:342-357.
Bavaresco, et al. The role of ecto-5'-nucleotidase/CD73 in glioma cell line proliferation. Mol Cell Biochem. Dec. 2008;319(1-2):61-8. Epub Jul. 18, 2008.
Bjorklund, et al. Embryonic stem cells develop into functional dopaminergic neurons after transplantation in a Parkinson rat model. Proc Natl Acad Sci U S A. Feb. 19, 2002;99(4):2344-9. Epub Jan. 8, 2002.
Boiani, et al. Regulatory networks in embryo-derived pluripotent stem cells. Nature Rev. Mol. Cell Biol. 2005; 6:872-884.
Cavaleri, et al. Nanog: a new recruit to the embryonic stem cell orchestra. Cell. 2003; 113:551-552.
Chai, et al. FGF Is an Essential Regulator of the Fifth Cell Division in Preimplantation Mouse Embryos, Development Biology, vol. 198, pp. 105-115 (1998).
Chambers, et al. Functional expression cloning of Nanog, a pluripotency sustaining factor in embryonic stem cells. Cell. 2003; 113:643-655.
Chambers, et al. Self-renewal of teratocarcinoma and embryonic stem cells. Oncogene. 2004; 23:7150-7160.
Chen, et al. Expression of leukemia inhibitory factor and its receptor is not altered in the decidua and chorionic villi of human anembryonic pregnancy. Hum Reprod. Jul. 2004;19(7):1647-54. Epub Jun. 4, 2004.

Chen, et al. Promotion of feeder-independent self-renewal of embryonic stem cells by retinol (vitamin A). Stem Cells. Jul. 2008;26(7):1858-64. Epub Apr. 24, 2008.
Cheng, et al. Human Adult Marrow Cells Support Prolonged Expansion of Human Embryonic Stem Cells in Culture, Stem Cells, vol. 21 pp. 131-142 (2003).
Chenn, et al. Regulation of cerebral cortical size by control of cell cycle exit in neural precursors. Science. 2002; 297:365-369.
Copp, A.J. Interaction between inner cell mass and trophectoderm of the mouse blastocyst, J. Embryol. Exp. Morph., vol. 51, pp. 109-120 (1979).
International Preliminary Report on Patentability mailed Nov. 23, 2007 in connection with PCT/US2006/006512.
International Search Report mailed Nov. 23, 2007 in connection with PCT/US2006/006512.
Written Opinion mailed Nov. 23, 2007 in connection with PCT/US2006/006512.
Dunnett, et al. Cell therapy in Parkinson's disease—stop or go? Nat. Rev. Neurosci. 2001; 2:365-369.
Freed, et al. Transplantation of embryonic dopamine neurons for severe Parkinson's disease. N. Engl. J. Med. 2001; 344:710-719.
Gerami-Naini, et al. Trophoblast Differentiation in Embryoid Bodies Derived from Human Embryonic Stem Cells, Endocrinology, vol. 145(4) p. 1517-1524 (2004).
Gotz. Glial cells generate neurons—master control within CNS regions: developmental perspectives on neural stem cells. Neuroscientist. 2003; 9:379-97.
He, et al. Lymphoid enhancer factor 1-mediated Wnt signaling promotes the initiation of trophoblast lineage differentiation in mouse embryonic stem cells. Stem Cells. Apr. 2008;26(4):842-9. Epub Jan. 10, 2008.
Iancu, et al. Behavioral characterization of a unilateral 6-OHDA-lesion model of Parkinson's disease in mice, Behavioural Brain Research, vol. 162 pp. 1-10 (2005).
Ilancheran, et al. Human fetal membranes: a source of stem cells for tissue regeneration and repair? Placenta. Jan. 2009;30(1):2-10. Epub Nov. 7, 2008.
Jacobs, et al. Retinoic acid is required early during adult neurogenesis in the dentate gyrus. Proc Natl Acad Sci USA. Mar. 7, 2006;103(10):3902-7. Epub Feb. 27, 2006.
Kehler, et al. Oct4 is required for primordial germ cell survival, European Molecular Biology Organization reports, vol. 5 No. 1 1, pp. 1078-1083 (2004).
Keltz, et al. Modulation of leukemia inhibitory factor gene expression and protein biosynthesis in the human fallopian tube. Am J Obstet Gynecol. Dec. 1996;175(6):1611-9.
Kim, et al. Dopamine neurons derived from embryonic stem cells function in an animal model of Parkinson's disease. Nature. Jul. 4, 2002;418(6893):50-6. Epub Jun. 20, 2002.
Kimura, et al. Conditional loss of PTEN leads to testicular teratoma and enhances embryonic germ cell production. Development. 2003; 130:1691-1700.
Kunath, et al. Trophoblast Stem Cells, Stem Cell Biology, pp. 267-287, (2001).
Kurie, et al. Retinoic acid stimulates the protein kinase C pathway before activation of its beta-nuclear receptor during human teratocarcinoma differentiation. Biochim Biophys Acta. 1993; 1179(2):203-7.
Li, et al. Human embryonic stem cells possess immune-privileged properties. Stem Cells. 2004; 22:448-456.
Li, et al. Specification of motoneurons from human embryonic stem cells. Nat Biotechnol. Feb. 2005;23(2):215-21. Epub Jan. 30, 2005.
Lindvall, et al. Stem cell therapy for human neurodegenerative disorders—how to make it work. Nat Med. Jul. 2004;10 Suppl:S42-50.
Lindvall, et al. Stem cells for the treatment of neurological disorders. Nature. 2006; 441:1094-1096.
Lu, et al. All-trans retinoic acid promotes neural lineage entry by pluripotent embryonic stem cells via multiple pathways. BMC Cell Biol. 2009; 10:57.
Maden. Retinoic acid in the development, regeneration and maintenance of the nervous system. Nat. Rev. Neuroscience. 2007; 8:755-765.

(56) References Cited

OTHER PUBLICATIONS

Martin-Ibanez, et al. Interplay of leukemia inhibitory factor and retinoic acid on neural differentiation of mouse embryonic stem cells. J. Neuron. Res. 2007; 85:2686-2710.
Miller. Human gene therapy comes of age. Nature. Jun. 11, 1992;357(6378):455-60.
Mulligan. The basic science of gene therapy. Science. May 14, 1993;260(5110):926-32.
Myers, et al. Functional characterization of the brain-specific FGF-1 promoter, FGF-1.B. J. Biol. Chem. 1995; 270:8257-8266.
Napoli, et al. Microglial clearance function in health and disease. Neuroscience. Feb. 6, 2009;158(3):1030-8. Epub Jul. 1, 2008.
Nichols, et al. Formation of Pluripotent Stem Cells in the Mammalian Embryo Depends on the POU Transcription Factor Oct 4, Cell, vol. 95, pp. 379-391 (1998).
Niwa, et al. Interaction between Oct3/4 and Cdx2 determines trophectoderm differentiation. Cell. 2005; 123:917-929.
Niwa. Development. How is pluripotency determined and maintained? Development. Feb. 2007;134(4):635-46. Epub Jan. 10, 2007.
Panicker, et al. Stem cells and neurogenesis. Stem Cell Biology. 2001; 399-438.
Parolini, et al. Concise review: isolation and characterization of cells from human term placenta: outcome of the first international Workshop on Placenta Derived Stem Cells. Stem Cells. Feb. 2008;26(2):300-11. Epub Nov. 1, 2007.
Qi, et al. BMP4 supports self-renewal of embryonic stem cells by inhibiting mitogen-activated protein kinase pathways. Proc Natl Acad Sci U S A. Apr. 20, 2004;101(16):6027-32. Epub Apr. 9, 2004.
Qureshi, et al. Anti-DNA antibodies cross-reacting with laminin inhibit trophoblast attachment and migration: implications for recurrent pregnancy loss in SLE patients. Am J Reprod Immunol. Sep. 2000;44(3):136-42.
Reubinoff, et al. Neural progenitors from human embryonic stem cells. Nat. Biotech. 2001; 19:1134-1140.
Rossant, J. Stem Cells from the Mammalian Blastocyst, Stem Cells, vol. 19, pp. 477-482 (2001).
Roy, et al. Functional engraftment of human ES cell-derived dopaminergic neurons enriched by coculture with telomerase-immortalized midbrain astrocytes. Nat Med. Nov. 2006;12(11):1259-68. Epub Oct. 22, 2006.
Schulz, et al. Human embryonic stem cells as models for trophoblast differentiation. Placenta. Mar. 2008;29 Suppl A:S10-6.
Shamblott, et al. Derivation of pluripotent stem cells from cultured human primordial germ cells, Proc. Natl. Acad. Sci. USA, vol. 95, pp. 13726-13731 (1998).
Shamblott, et al. Human embryonic germ cell derivatives express a broad range of developmentally distinct markers and proliferate extensively in vitro, Proc. Natl. Acad. Sci., vol. 98 No. 1, pp. 113-118 (2001).
Singh, et al. Identification of human brain tumour initiating cells. Nature. 2004; 432:396-401.
Smith, et al. Inhibition of pluripotential embryonic stem cell differentiation by purified polypeptides. Nature. 1998; 336:688-690.
Smith, et al. Placental involvement in congenital neuroblastoma. J. Clin. Pathol. 1981; 34:785-789.
Song, et al. Astroglia induce neurogenesis from adult neural stem cells. Nature. 2002; 417:39-44.
Surani, et al. Genetic and epigenetic regulators of pluripotency. Cell. 2007; 128:747-762.
Swijenburg, et al. Immunosuppressive therapy mitigates immunological rejection of human embryonic stem cell xenografts. Proc Natl Acad Sci U S A. Sep. 2, 2008;105(35):12991-6. Epub Aug. 26, 2008.
Thornson, et al. Embroynic Stem Cell Lines Derived from Human Blastocysts, Science, vol. 282 pp. 1145-1147 (1998).
Torres, et al. Nanog maintains pluripotency of mouse embryonic stem cells by inhibiting NFkappaB and cooperating with Stat3. Nat Cell Biol. Feb. 2008;10(2):194-201. Epub Jan. 27, 2008.
Tropepe. Direct neural fate specification from embryonic stem cells: a primitive mammalian neural stem cell stage acquired through a default mechanism. Neuron. 2001; 30:65-78.
Tsai, et al. Involvement of replicative polymerases, Tel1p, Mec1p, Cdc13p, and the Ku complex in telomere-telomere recombination. Mol. Cell. Biol. 2002; 22:5679-5687.
Tsai, et al. The ubiquitin ligase gp78 promotes sarcoma metastasis by targeting KAI1 for degradation. Nat. Med. 2007; 13:1504-1509.
Van Brunt. Molecular farming: Transgenic animals as bio-reactors. Biotechnology. 1988; 6(10):1149-1154.
Wagner, et al. Induction of a midbrain dopaminergic phenotype in Nurr1-overexpressing neural stem cells by type 1 astrocytes. Nat. Biotechnol. 1999; 17:653-659.
Wanggren, et al. Leukaemia inhibitory factor receptor and gp130 in the human Fallopian tube and endometrium before and after mifepristone treatment and in the human preimplantation embryo. Mol Hum Reprod. Jun. 2007;13(6):391-7. Epub Apr. 12, 2007.
Wichterle, et al. Directed differentiation of embryonic stem cells into motor neurons. Cell. 2002; 110:385-397.
Williams, et al Myeloid leukemia inhibitory factor maintains the developmen- tal potential of embryonic stem cells. Nature. 1998; 336:684-687.
Wu, et al. Suppression of hydroxyl radical formation and protection of nigral neurons by 1-deprenyl (selegiline). Ann. N.Y. Acad. Sci. 1996; 786:379-389.
Xu, et al. BMP4 initiates human embryonic stem cell differentiation to trophoblast. Nat Biotechnol. Dec. 2002;20(12):1261-4. Epub Nov. 11, 2002.
Xu, R. In vitro induction of trophoblast from human embryonic stem cells. Methods Mol Med. 2006;121:189-202.
Yamanaka, et al. Cell and molecular regulation of the mouse blastocyst. Dev Dyn. Sep. 2006;235(9):2301-14.
Yan, et al. Retinoic acid promotes differentiation of trophoblast stem cells to a giant cell fate. Dev. Biol. 2001; 235:422-432.
Ying, et al. BMP induction of Id proteins suppresses differentiation and sustains embryonic stem cell self-renewal in collaboration with STAT3. Cell. 2003; 115:281-292.
Yu, et al. Progress towards gene therapy for HIV infection. Gene Ther. Jan. 1994;1(1):13-26. Abstract only.
Zhang, et al. Induction of neuronal differentiation of adult human olfactory neuroepithelial-derived progenitors. Brain Res. Feb. 16, 2006;1073-1074:109-19. Epub Feb. 7, 2006.
Zhu, et al. Grafted neural stem cells migrate to substantia nigra and improve behavior in Parkinsonian rats. Neurosci Lett. Oct. 25, 2009;462(3):213-8. Epub Jul. 9, 2009.
Alexiou, et al. miRGen 2.0: a database of microRNA genomic information and regulation. Nucleic Acids Res. Jan. 2010;38(Database issue):D137-41. doi: 10.1093/nar/gkp888. Epub Oct. 22, 2009.
Ameri, et al. FGF2 specifies hESC-derived definitive endoderm into foregut/midgut cell lineages in a concentration-dependent manner. Stem Cells. Jan. 2010;28(1):45-56. doi: 10.1002/stem.249.
Baroukh, et al. MicroRNA-124a regulates Foxa2 expression and intracellular signaling in pancreatic beta-cell lines. J Biol Chem. Jul. 6, 2007;282(27):19575-88. Epub Apr. 26, 2007.
Bernardo, et al. Biphasic induction of Pdx1 in mouse and human embryonic stem cells can mimic development of pancreatic beta-cells. Stem Cells. Feb. 2009;27(2):341-51. doi: 10.1634/stemcells.2008-0310.
Borowiak. The new generation of beta-cells: replication, stem cell differentiation, and the role of small molecules. Rev Diabet Stud. 2010 Summer;7(2):93-104. doi: 10.1900/RDS.2010.7.93. Epub Aug. 10, 2010.
Burlison, et al. Pdx-1 and Ptf1 a concurrently determine fate specification of pancreatic multipotent progenitor cells. Dev Biol. Apr. 1, 2008;316(1):74-86. doi: 10.1016/j.ydbio.2008.01.011. Epub Jan. 26, 2008.
Cunliffe, et al. Switching on the notochord. Genes Dev. Jul. 1, 1999;13(13):1643-6.
D'Amour, et al. Efficient differentiation of human embryonic stem cells to definitive endoderm. Nat Biotechnol. Dec. 2005;23(12):1534-41. Epub Oct. 28, 2005.

(56) References Cited

OTHER PUBLICATIONS

Edghill, et al. Hepatocyte nuclear factor-1 beta mutations cause neonatal diabetes and intrauterine growth retardation: support for a critical role of HNF-1beta in human pancreatic development. Diabet Med. Dec. 2006;23(12):1301-6.

Episkopou. SOX2 functions in adult neural stem cells. Trends Neurosci. May 2005;28(5):219-21.

Furuyama, et al. Continuous cell supply from a Sox9-expressing progenitor zone in adult liver, exocrine pancreas and intestine. Nat Genet. Jan. 2011;43(1):34-41. doi: 10.1038/ng.722. Epub Nov. 28, 2010.

Gradwohl, et al. neurogenin3 is required for the development of the four endocrine cell lineages of the pancreas. Proc Natl Acad Sci U S A. Feb. 15, 2000;97(4):1607-11.

Graphin-Botton, et al. Key events of pancreas formation are triggered in gut endoderm by ectopic expression of pancreatic regulatory genes. Genes Dev. Feb. 14, 2001;15(4):444-54.

Hart, et al. Mix11 is required for axial mesendoderm morphogenesis and patterning in the murine embryo. Development. Aug. 2002;129(15):3597-608.

Hochedlinger, et al. Nuclear transplantation, embryonic stem cells, and the potential for cell therapy. N Engl J Med. Jul. 17, 2003;349(3):275-86.

Izzi, et al. Foxh1 recruits Gsc to negatively regulate Mix11 expression during early mouse development. EMBO J. Jul. 11, 2007;26(13):3132-43. Epub Jun. 14, 2007.

Kroon, et al. Pancreatic endoderm derived from human embryonic stem cells generates glucose-responsive insulin-secreting cells in vivo. Nat Biotechnol. Apr. 2008;26(4):443-52. doi: 10.1038/nbt1393. Epub Feb. 20, 2008.

Lee, et al. Ectopic pregnancy-derived human trophoblastic stem cells regenerate dopaminergic nigrostriatal pathway to treat parkinsonian rats. PLoS One. 2012;7(12):e52491. doi: 10.1371/journal.pone.0052491. Epub Dec. 21, 2012.

Liew. Generation of insulin-producing cells from pluripotent stem cells: from the selection of cell sources to the optimization of protocols. Rev Diabet Stud. 2010 Summer;7(2):82-92. doi: 10.1900/RDS.2010.7.82. Epub Aug. 10, 2010.

Lim, et al. Enforced expression of Mix11 during mouse ES cell differentiation suppresses hematopoietic mesoderm and promotes endoderm formation. Stem Cells. Feb. 2009;27(2):363-74. doi: 10.1634/stemcells.2008-1008.

Lovis, et al. Regulation of the expression of components of the exocytotic machinery of insulin-secreting cells by microRNAs. Biol Chem. Mar. 2008;389(3):305-12. doi: 10.1515/BC.2008.026.

Makeyev, et al. The MicroRNA miR-124 promotes neuronal differentiation by triggering brain-specific alternative pre-mRNA splicing. Mol Cell. Aug. 3, 2007;27(3):435-48.

Marson, et al. Connecting microRNA genes to the core transcriptional regulatory circuitry of embryonic stem cells. Cell. Aug. 8, 2008;134(3):521-33. doi: 10.1016/j.cell.2008.07.020.

Morn, et al. Mouse Mix gene is activated early during differentiation of ES and F9 stem cells and induces endoderm in frog embryos. Dev Dyn. Mar. 2003;226(3):446-59.

Office action dated Aug. 18, 2009 for U.S. Appl. No. 11/361,588.
Office action dated Nov. 25, 2008 for U.S. Appl. No. 11/361,588.
Office action dated Dec. 18, 2012 for U.S. Appl. No. 13/415,595.

Offield, et al. PDX-1 is required for pancreatic outgrowth and differentiation of the rostral duodenum. Development. Mar. 1996;122(3):983-95.

Pauli, et al. Non-coding RNAs as regulators of embryogenesis. Nat Rev Genet. Feb. 2011;12(2):136-49. doi: 10.1038/nrg2904.

Pereira, et al. Brachyury and related Tbx proteins interact with the Mix11 homeodomain protein and negatively regulate Mix11 transcriptional activity. PLoS One. 2011;6(12):e28394. doi: 10.1371/journal.pone.0028394. Epub Dec. 2, 2011.

Pereira, et al. The Mix family of homeobox genes—key regulators of mesendoderm formation during vertebrate development. Dev Biol. Jul. 15, 2012;367(2):163-77. doi: 10.1016/j.ydbio.2012.04.033. Epub May 8, 2012.

Rajasethupathy, et al. Characterization of small RNAs in Aplysia reveals a role for miR-124 in constraining synaptic plasticity through Creb. Neuron. Sep. 24, 2009;63(6):803-17. doi: 10.1016/j.neuron.2009.05.029.

Schisler, et al. Stimulation of human and rat islet beta-cell proliferation with retention of function by the homeodomain transcription factor Nkx6.1. Mol Cell Biol. May 2008;28(10):3465-76. doi: 10.1128/MCB.01791-07. Epub Mar. 17, 2008.

Seymour, et al. SOX9 is required for maintenance of the pancreatic progenitor cell pool. Proc Natl Acad Sci U S A. Feb. 6, 2007;104(6):1865-70. Epub Jan. 31, 2007.

Shiraki, et al. Guided differentiation of embryonic stem cells into Pdx1-expressing regional-specific definitive endoderm. Stem Cells. Apr. 2008;26(4):874-85. doi: 10.1634/stemcells.2007-0608. Epub Jan. 31, 2008.

Silva, et al. Capturing pluripotency. Cell. Feb. 22, 2008;132(4):532-6. doi: 10.1016/j.cell.2008.02.006.

Sneddon, et al. Self-renewal of embryonic-stem-cell-derived progenitors by organ-matched mesenchyme. Nature. Nov. 29, 2012;491(7426):765-8. doi: 10.1038/nature11463. Epub Oct. 7, 2012.

Spence, et al. Sox17 regulates organ lineage segregation of ventral foregut progenitor cells. Dev Cell. Jul. 2009;17(1):62-74. doi: 10.1016/j.devcel.2009.05.012.

Tam, et al. Early endoderm development in vertebrates: lineage differentiation and morphogenetic function. Curr Opin Genet Dev. Aug. 2003;13(4):393-400.

Tam, et al. Sequential allocation and global pattern of movement of the definitive endoderm in the mouse embryo during gastrulation. Development. Jan. 2007;134(2):251-60. Epub Dec. 6, 2006.

Wells, et al. Vertebrate endoderm development. Annu Rev Cell Dev Biol. 1999;15:393-410.

Xi, et al. A poised chromatin platform for TGF-β access to master regulators. Cell. Dec. 23, 2011;147(7):1511-24. doi: 10.1016/j.cell.2011.11.032.

Barral, et al. Roles of molecular chaperones in protein misfolding diseases. Seminars in Cell & Developmental Biology. 2004; 15:17-29.

Coutinho, et al. An Evolving Hierarchical Family Classification for Glycosyltransferases. J. Mol. Biol. 2003; 328:307-317.

Okano, et al. Neural stem cells: involvement in adult neurogenesis and CNS repair. Phil. Trans. R. Soc. B. 2008; 363:2111-2122. doi:10.1098/rstb.2008.2264.

Schwartz, et al. Differentiation of Neural Lineage Cells from Human Pluripotent Stem Cells. Methods. Jun. 2008; 45(2):142-158. doi:10.1016/j.ymeth.2008.03.007.

Taupin. Adult neural stem cells: The promise of the future. Neuropsychiatric Disease and Treatment 2007:3(6) 753-760.

Yokoyama, et al. Involvement of Two Distinct N-Acetylglucosaminyltransferases and a Dual-Function Deacetylase in Neomycin Biosynthesis. ChemBioChem. 2008; 9:865-869.

Yu, et al. Stem cell sources and therapeutic approaches for central nervous system and neural retinal disorders. Neurosurg Focus. 2008; 24(3-4): E11. doi:10.3171/FOC/2008/24/3-4/E10.

International search report and written opinion dated May 3, 2012 for PCT/US2011/060868.

Bi, et al. Pre-activation of retinoid signaling facilitates neuronal differentiation of mesenchymal stem cells. Dev Growth Differ. 2010;52(5):419-31. doi: 10.1111/j.1440-169X.2010.01182.x.

Gage, et al. Neural stem cells: generating and regenerating the brain. Neuron. 2013;80(3):588-601. doi: 10.1016/j.neuron.2013.10.037.

Goncalves, et al. Sequential RARbeta and alpha signalling in vivo can induce adult forebrain neural progenitor cells to differentiate into neurons through Shh and FGF signalling pathways. Dev Biol. 2009;326(2):305-13. doi: 10.1016/j.ydbio.2008.11.018. Epub Dec. 7, 2008.

Goncalves, et al. Timing of the retinoid-signalling pathway determines the expression of neuronal markers in neural progenitor cells. Dev Biol. 2005;278(1):60-70.

Kennea, et al. Neural stem cells. J Pathol. 2002;197(4):536-50.

Kornblum, et al. Introduction to neural stem cells. Stroke. 2007;38(2 Suppl):810-6.

(56) References Cited

OTHER PUBLICATIONS

Office action dated Mar. 3, 2014 for U.S. Appl. No. 13/909,469.
Seaberg, et al. Stem and progenitor cells: the premature desertion of rigorous definitions. Trends Neurosci. 2003;26(3):125-31.
International search report and written opinion dated Mar. 13, 2013 for PCT/US2013/072073.
Jiang, et al. In vitro derivation of functional insulin-producing cells from human embryonic stem cells. Cell Res. Apr. 2007;17(4):333-44.
Office action dated Aug. 4, 2014 for U.S. Appl. No. 13/909,469.
Rossant, et al. Effect of culture conditions on diploid to giant-cell transformation in postimplantation mouse trophoblast, J. Embryol. exp. Morph., vol. 62, pp. 217-227 (1981).
Thomson, et al. Embroynic Stem Cell Lines Derived from Human Blastocysts, Science, vol. 282 pp. 1145-1147 (1998).
Wilcox. Insulin and insulin resistance. Clin Biochem Rev. May 2005;26(2):19-39.
Xu, et al. Activin, BMP and FGF pathways cooperate to promote endoderm and pancreatic lineage cell differentiation from human embryonic stem cells. Mech Dev. Sep.-Dec. 2011;128(7-10):412-27. doi: 10.1016/j.mod.2011.08.001. Epub Aug. 10, 2011.
Barany. Genetic disease detection and DNA amplification using cloned thermostable ligase. Proc Natl Acad Sci U S A. Jan. 1, 1991;88(1):189-93.
Choi, et al. Efficient drug screening and gene correction for treating liver disease using patient-specific stem cells. Hepatology. Jun. 2013;57(6):2458-68. doi: 10.1002/hep.26237.
Co-pending U.S. Appl. No. 14/952,023, filed Nov. 25, 2015.
D'Amour, et al. Production of pancreatic hormone-expressing endocrine cells from human embryonic stem cells. Nat Biotechnol. Nov. 2006;24(11):1392-401. Epub Oct. 19, 2006.
European search report and search opinion dated Apr. 15, 2016 for EP Application 13858016.2.
Guatelli, et al. Isothermal, in vitro amplification of nucleic acids by a multienzyme reaction modeled after retroviral replication. Proc Natl Acad Sci U S A. Mar. 1990;87(5):1874-8.
Guha, et al. Hepatocyte-based gene therapy. J Hepatobiliary Pancreat Surg. 2001;8(1):51-7.
Haimovici, et al. Effects of growth factors and growth factor-extracellular matrix interactions on mouse trophoblast outgrowth in vitro. Biol Reprod. Jul. 1993;49(1):124-30.
International search report and written opinion dated Mar. 15, 2016 for PCT Application No. PCTUS2015-062674.
Kuckenberg, et al. Lineage conversion of murine extraembryonic trophoblast stem cells to pluripotent stem cells.Mol Cell Biol. Apr. 2011;31(8):1748-56. doi: 10.1128/MCB.01047-10. Epub Feb. 7, 2011.
Kwoh, et al. Transcription-based amplification system and detection of amplified human immunodeficiency virus type 1 with a bead-based sandwich hybridization format. Proc Natl Acad Sci U S A. Feb. 1989;86(4):1173-7.
Liu, et al. In vivo liver regeneration potential of human induced pluripotent stem cells from diverse origins. Sci Transl Med. May 11, 2011;3(82):82ra39. doi: 10.1126/scitranslmed.3002376.
Lizardi, et al. Exponential amplification of recombinant-RNA hybridization probes. Nature Biotechnology 6.10 (1988): 1197-1202.
Office action dated Oct. 8, 2015 for U.S. Appl. No. 14/090,804.
Roelandt, et al. Human embryonic and rat adult stem cells with primitive endoderm-like phenotype can be fated to definitive endoderm, and finally hepatocyte-like cells. PLoS One. Aug. 11, 2010;5(8):e12101. doi: 10.1371/journal.pone.0012101.
Schwartz, et al. Multipotent adult progenitor cells from bone marrow differentiate into functional hepatocyte-like cells. J Clin Invest. May 2002;109(10):1291-302.
Tee, et al. Immunogenicity and immunomodulatory properties of hepatocyte-like cells derived from human amniotic epithelial cells. Curr Stem Cell Res Ther. Jan. 2013;8(1):91-9.

* cited by examiner

FIGURE 1
1(a)
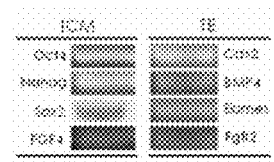
1(b)
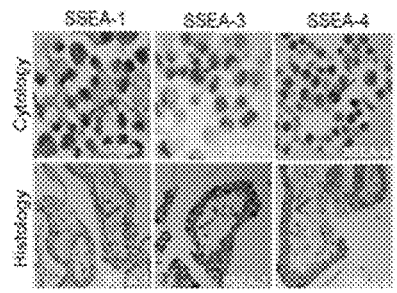
1(c) upper panel
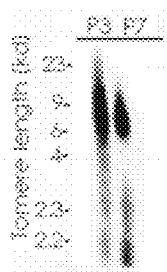
1(d)
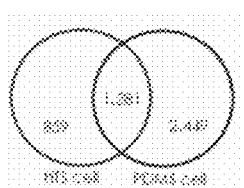
1(e)
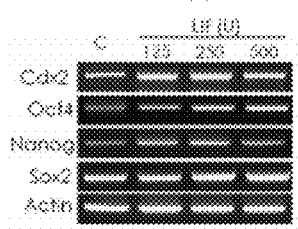
1(c) lower panel
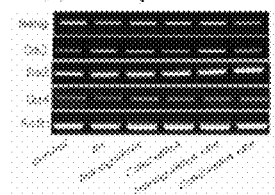
1(f) left panel
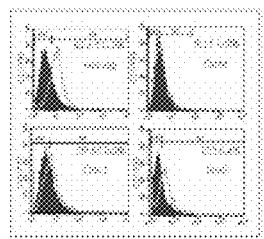
1(f) right panel
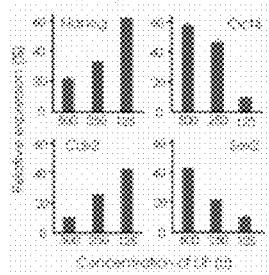
1(g)
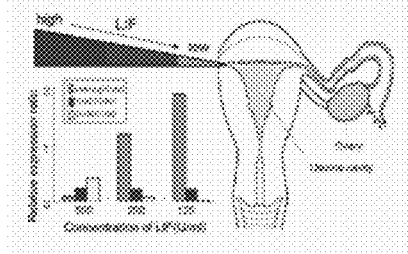
1(h) left
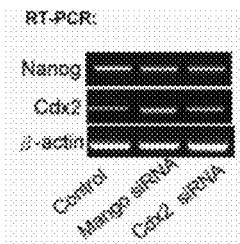
1(h) right
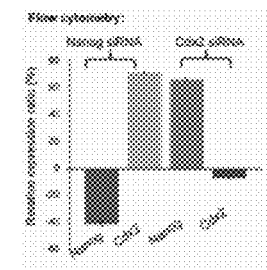
1(i)
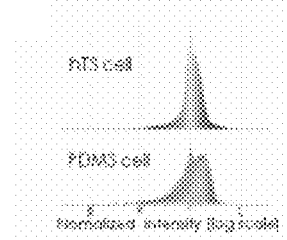

FIGURE 5
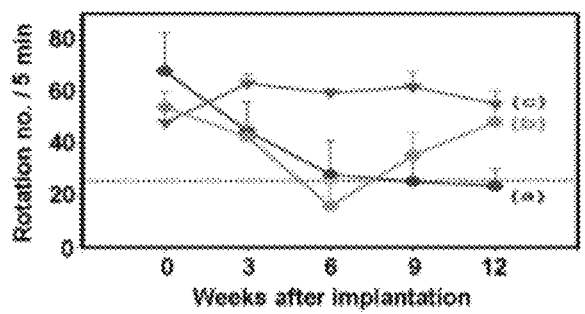
5a
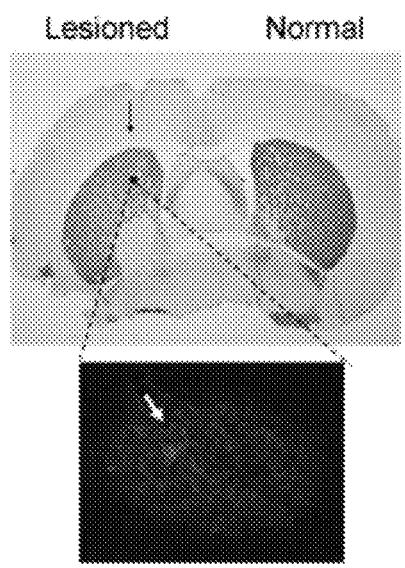
5b
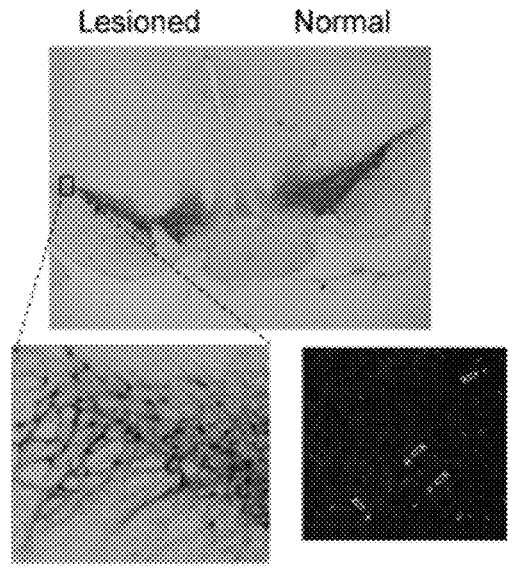
5c
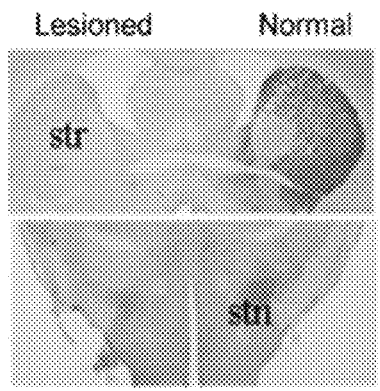
5d
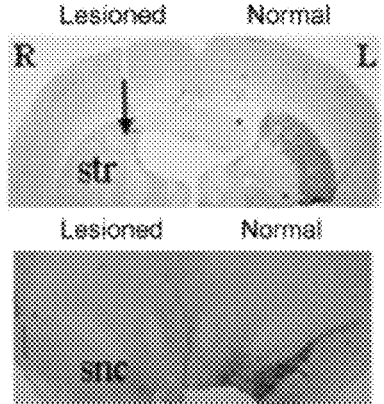
5e

FIGURE 10
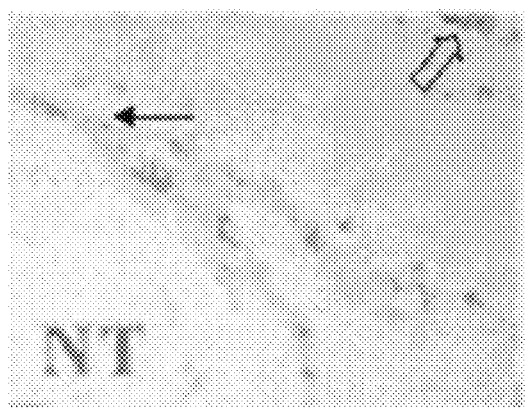
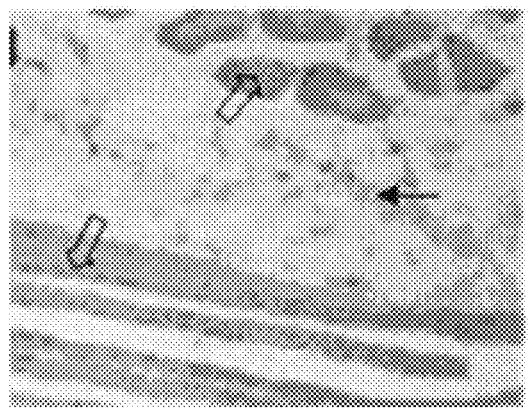

FIGURE 12

Recipes used for cell differentiations

| Differentiation | Protocol |
|---|---|
| Osteogenesis | α-MEM containing 20% FBS, 10μg/ml bFGF, 0.1μM dexamethasone, 10mMβ-glycerolphosphate and 0.2mM ascorbic acid |
| Chondrogenesis | α-MEM containing 10% FBS, 1% antibiotic/antimycotic, 6.25μg/ml insulin, 10 ng/ml TGF-β1 and 50 nM ascorbate-2-phosphate |
| Myogenesis | α-MEM containing 10% FBS, 10μg/ml bFGF, 0.1 mM dexamethasone, 50 mM hydrocortisone and 5% horse serum |
| Adipogenesis | α-MEM containing 20% FBS, 10μg/ml bFGF, 10μg/ml insulin, 1μMdexamethasone, 0.5mM isobutyl methylxanthine and 200μM indomethacin |
| Neurogenesis | α-MEM containing 20% FBS and 10μM all trans-retinoic acid |
| Pancreatic islet β-cells | L-DMEM containing 20% FBS, 5.5mmol/L glucose, 10mmol/L nicotinamide, 1mmol/L β-mercaptoethanol, H-DMEM containing 15 mmol/L glucose, 10mmol/L nicotinamide and 1mmol/L β-mercaptoethanol |

| Plasmid transfection | Reagents |
|---|---|
| HBS solution | 8.67g NaCl in 80 ml Milli Q, 2 ml 1M HEPES (GIBCO HEPES Buffer solution cat. No.:15630-080), adjusted pH to 7.4 and filterd by 0.2 μm filter and stored at 4°C. |

FIGURE 13

PCR primers used for RT-PCR

| Gene | Sequence (5'→3') | Product size (bp) | Anneal temp °C |
|---|---|---|---|
| Osteopontin | Forward: CTAGGCATCACCTGTGCCATACC<br>Reverse: CAGTGACCAGTTCATCAGATTCATC | 330 | 55.7 |
| Osteocalcin | Forward: CGCAGCCACCGAGACACCAT<br>Reverse: GGGCAAGGGCAAGGGGAAGA | 485 | 66 |
| Perlecan (PRLN) | Forward: CATAGAGACCGTCACAGCAAG<br>Reverse: ATGAACACCACACTGACAACC | 300 | 50 |
| Collagen typeII | Forward: ACGGCGAGAAGGGAGAAGTTG<br>Reverse: GGGGGTCCAGGGTTGCCATTG | 352 | 60.1 |
| Myogenin | Forward: AGCGCCCCCTCGTGTATG<br>Reverse: TGTCCCCGGCAACTTCAGC | 365 | 61 |
| MyoD1 | Forward: CGGCGGCGGAACTGCTACGAA<br>Reverse: GGGGCGGGGGCGGAAACTT | 452 | 65.8 |
| PPARγ-2 | Forward: GCTGTTATGGGTGAAACTCTG<br>Reverse: ATAAGGTGGAGATGCAGGCTC | 352 | 50.7 |
| Adipsin | Forward: GGTCACCCAAGCAACAAAGT<br>Reverse: CCTCCTGCGTTCAAGTCATC | 269 | 61 |
| β2-microglobulin | Forward: CTCGCGCTACTCTCTCTCTTTCTGG<br>Reverse: GCTTACATGTCTCGATCCCACTTAA | 335 | 57.3 |
| β-actin | Forward: GTGGGGCGCCCCAGGCACCA<br>Reverse: CTCCTTAATGTCACGCACGATTTC | 539 | 55.5 |
| Oct4 | Forward: GGAAAGGCTTCCCCCTCAGGGAAAGG<br>Reverse: AAGAACATGTGTAAGCTGCGGCCC | 454 | 64 |
| Cdx2-exon 2 | Forward: GTGTACACGGACCACCAGCG<br>Reverse: GGTGGCTGCTGCTGCTGTTG | 199 | 60 |

FIGURE 13 Continued

| Gene | Sequence (5'→3') | Product size (bp) | Anneal temp °C |
|---|---|---|---|
| Cdx2-exon 1 | Forward: AGCCAAGTGAAAACCAGGAC<br>Reverse: TTTCCTCTCCTTTGCTCTGC | 563 | 60 |
| Nanog | Forward: CTCAGCCTCCAGCAGATGC<br>Reverse: AGGCATCCCTGGTGGTAGG | 280 | 60 |
| Eomeso | Forward: GGCCACTGCGCGCTACTCC<br>Reverse: GGCTCCTGGGCCGAACTGC | 251 | 65 |
| FGF4 | Forward: CCTGGTGGCGCTCTCGTTG<br>Reverse: GCAGGCTGTCGCGGGTGTC | 199 | 60 |
| fgfr-2 | Forward: CACCGTGGCCGTGAAGATG<br>Reverse: GGGCTCGGAGGTATTCTCG | 199 | 61 |
| BMP4 | Forward: CGCTGGACCCGGGAGAAGC<br>Reverse: CTCCGGCGTCGGGTCAAGG | 280 | 63 |
| LIF | Forward: CGTGTACCTTGGCACCTCC<br>Reverse: CCTTACCCGAGGTGTCAGG | 199 | 60 |

Figure 18
18a
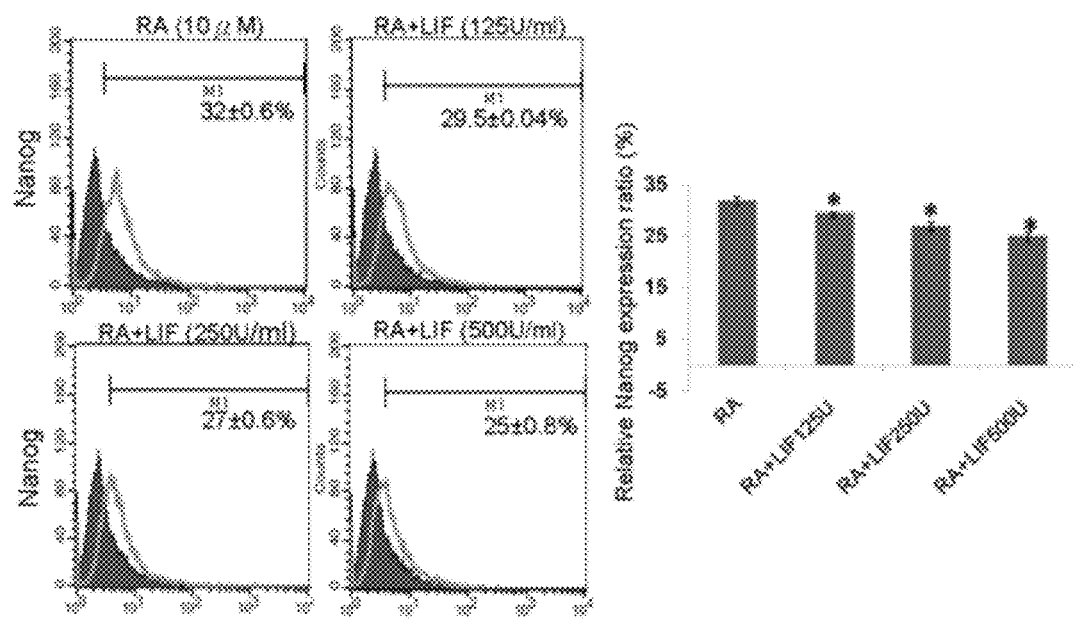
18b
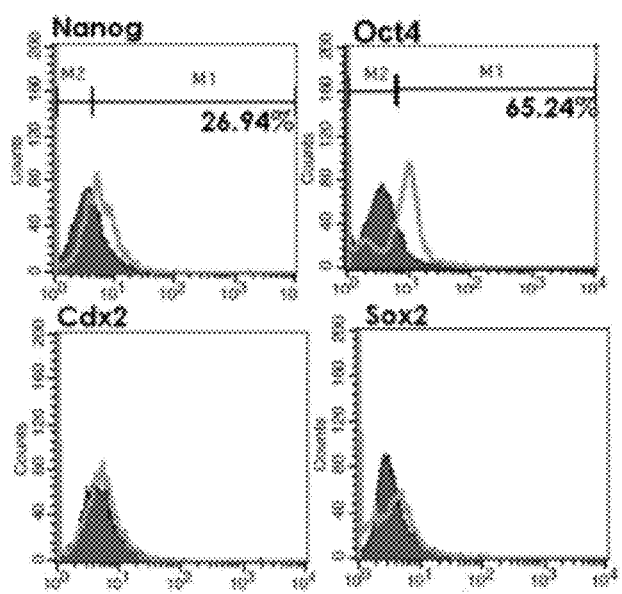

Figure 19
19a
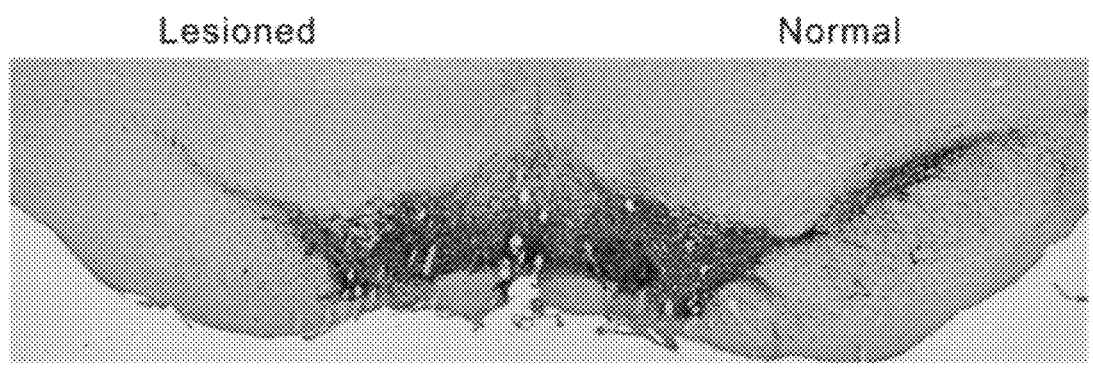
19b
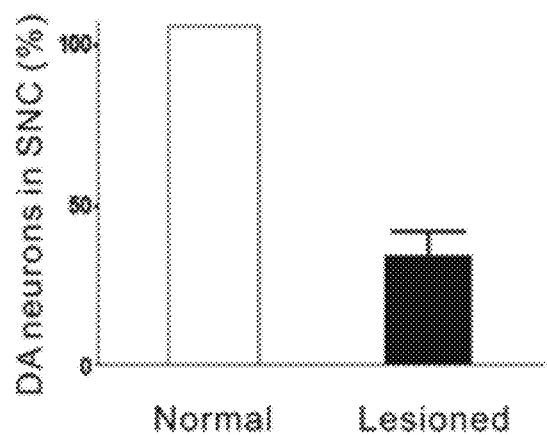

GENERATION OF NEURAL STEM CELLS FROM HUMAN TROPHOBLAST STEM CELLS

CROSS-REFERENCE

This application claims the benefit of U.S. Provisional Application No. 61/413,892, filed Nov. 15, 2010, and U.S. Provisional Application No. 61/434,790, filed Jan. 20, 2011, which applications are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 6, 2012, is named 38219726.txt and is 12, 129 bytes in size.

BACKGROUND OF THE INVENTION

The human trophoblast stem (hTS) cell is capable of indefinite proliferation in vitro in an undifferentiated state. The hTS cell maintains the potential multilineage differentiation capabilities. The hTS cell preparation can be induced to differentiate into cells of the trophoblast lineage in vitro or in vivo. Further, hTS cells can be induced to differentiate into neurons, such as dopaminergic neurons. The hTS cells can be used to treat a dysfunction or loss of the dopaminergic neurons in the nigrostriatal pathway, such as neurodegenerative disorders in humans.

SUMMARY OF THE INVENTION

Neurodegenerative disorders have profound socio-economic effects in the human population. Current drugs provide only limited benefit by alleviating certain symptoms of neurodegenerative disorders such as Parkinson's disease, Alzheimer's disease, Huntington's disease or the like. Parkinson's disease (PD) is caused by the dysfunction or loss of the dopaminergic neurons in the nigrostriatal pathway, and is a common neurodegenerative disorder in humans. Provided herein are isolated neural stem cells for alternative cell-based therapy in neurodegenerative disorders, including, Parkinson's disease, Huntington's disease, Alzheimer's disease, amyotrophic lateral sclerosis (ALS), multiple system atrophy, Lewy body dementia, peripheral sensory neuropathies or spinal cord injuries in mammals.

Provided herein, in one aspect, are isolated neural stem cells, wherein said isolated neural stem cells are derived from trophoblast tissue. In some embodiments, the trophoblast tissue is human trophoblast tissue.

In one embodiment, an isolated neural stem cell described herein expresses transcripts for one or more of caudal type homeobox 2 (Cdx2), Nanog homeobox, nestin, octamer-binding transcription factor 4(Oct-4), neurofilament, neurogenin-3 (Ngn3), neomycin-deleted gene (Neo-D), microtubule-associated protein-2 (MAP-2), CD133, retinoic acid receptor beta (RARβ), retinoid X receptor alpha (RXRα), retinoid X receptor beta (RXRβ), cellular retinoic acid binding protein 2 (CRABP-2), cellular retinol binding protein 1 (CRBP-1), retinaldehyde dehydrogenase 2 (RALDH-2) or retinaldehyde dehydrogenase 3 (RALDH-3).

In one embodiment, the isolated neural stem cell is a human neural stem cell. In one embodiment, the cell has a normal karyotype. In another embodiment, the isolated neural stem cell has one or more immune-privileged characteristics. In another embodiment, the one or more immune-privileged characteristics comprise absence of CD33 expression and/or CD133 expression.

Further provided herein are methods of differentiating the isolated neural stem cells into neurons, the method comprising: administering said isolated neural stem cell into the brain of a mammal, wherein said isolated neural stem cell differentiates into a neuron. In another embodiment, the neuron is a dopaminergic neuron, glutaminergic neuron, serotonergic neuron, or GABAergic (gamma aminobutyric acid) neuron.

In one embodiment, the administered (e.g., transplanted) isolated neural stem cells are pre-induced with an induction drug prior to said administering. In another embodiment, the isolated neural stem cells are not pre-induced with an induction drug prior to said administering.

In one embodiment, the brain of said mammal is damaged or has suffered neuronal loss, prior to said administering. In another embodiment, said damage is to a dopaminergic neuron, glutaminergic neuron, serotonergic neuron, or GABAergic (gamma aminobutyric acid) neuron. In another embodiment, said neuronal loss is to a dopaminergic neuron.

In one embodiment, said cell is transfected with an expression vector.

In another embodiment, the isolated neural stem cells, after being administered into the brain of said subject, migrate to substantia nigra pars compacta (SNC) region of the brain of the subject. In another embodiment, said administration improves sensorimotor function in said mammal. In another embodiment, said administration causes a reduction in said mammal's rigidity, akinesia or balance impairment.

Provided herein are methods of differentiating isolated neural stem cells into a dopaminergic neuron, the methods comprising: administering said isolated neural stem cells into the brain of a mammal, wherein said isolated neural stem cells express transcripts for one or more of Cdx2, Nanog, nestin, Oct-4, neurofilament, NgN3, Neo-D, MAP-2, CD133, RARβ, RXRα, RXRβ, CRABP-2, CRBP-1, RALDH-2 or RALDH-3, wherein said brain of said mammal is damaged or has suffered neuronal loss, wherein one or more of said isolated neural stem cells differentiates into a dopaminergic neuron.

Provided herein are methods of differentiating isolated neural stem cells into a dopaminergic neuron, the method comprising: administering said isolated neural stem cells into the brain of a mammal, wherein said isolated neural stem cell is derived from trophoblast tissue, wherein said brain of said mammal is damaged or has suffered neuronal loss, wherein one or more of said isolated neural stem cells differentiates into a dopaminergic neuron.

In one embodiment of the methods described above, said administration improves sensorimotor function in said mammal. In another embodiment of the methods described above, said administration causes a reduction in said mammal's rigidity, akinesia or balance impairment.

Provided herein are methods of differentiating an isolated human trophoblastic stem cell into a neural stem cell comprising: modulating the activity of a Cdx2, Nanog, nestin, Oct4, neurofilament, Ngn-3, Neo-D, MAP-2, CD133, RARβ, RXRα, RXRβ, CRABP-2, CRBP-1, RALDH-2, or RALDH-3 gene.

Provided herein are methods of differentiating an isolated human trophoblastic stem cell into a neural stem cell comprising: modulating the level of a Cdx2, Nanog, nestin, Oct4, neurofilament, Ngn-3, Neo-D, MAP-2, CD133, RARβ, RXRα, RXRβ, CRABP-2, CRBP-1, RALDH-2, or RALDH-3 transcript.

Provided herein are methods of differentiating an isolated human trophoblastic stem cell into a neural stem cell comprising: modulating the level or activity of a Cdx2, Nanog, nestin, Oct4, neurofilament, Ngn-3, Neo-D, MAP-2, CD133 RARβ, RXRα, RXRβ, CRABP-2, CRBP-1, RALDH-2, or RALDH-3 protein.

Provided herein are methods of screening a compound for use in treatment or prevention of a disease comprising: contacting an isolated human trophoblastic stem cell with said compound; and detecting a change in the activity of at least one gene, transcript or protein in said human trophoblastic stem cell. In one embodiment of the methods described above, the activity of at least one gene, transcript or protein in said human trophoblastic stem cell decreases as compared to a comparable isolated human trophoblastic stem cell not contacted with said compound. In another embodiment of the methods described above, the activity of at least one gene, transcript or protein in said human trophoblastic stem cell increases as compared to a comparable isolated human trophoblastic stem cell not contacted with said compound. In another embodiment of the methods described above, the disease is a neurodegenerative disorder. In another embodiment of the methods described above, the disease is Parkinson's, Alzheimer's, Schizophrenia, or Amyotrophic lateral sclerosis.

Provided herein are methods of screening a compound for use in treatment or prevention of a disease comprising: contacting an isolated human trophoblastic stem cell with said compound; and detecting a change in the level of at least one transcript or protein in said human trophoblastic stem cell. In one embodiment of the methods described above, the level of at least one transcript or protein in said human trophoblastic stem cell decreases as compared to an isolated human trophoblastic stem cell not contacted with said compound. In another embodiment of the methods described above, the level of at least one transcript or protein in said human trophoblastic stem cell increases as compared to a comparable isolated human trophoblastic stem cell not contacted with said compound. In another embodiment of the methods described above, the disease is a neurodegenerative disorder. In another embodiment of the methods described above, the disease is Parkinson's, Alzheimer's, Schizophrenia, or Amyotrophic lateral sclerosis.

Provided herein are methods of screening a compound for ability to induce changes in a cell comprising: contacting an isolated human trophoblastic stem cell with said compound; and detecting an induction of differentiation of said human trophoblastic stem cell.

Provided herein are methods of screening a compound for ability to induce changes in a cell comprising: contacting an isolated neural stem cell with said compound; and detecting an induction of differentiation of said neural stem cell.

Provided herein are methods of screening a compound for use in treatment or prevention of a disease comprising: contacting an isolated neural stem cell with said compound; and detecting a change in the activity of at least one gene, transcript or protein in said neural stem cell. In one embodiment of the methods described above, the activity of at least one gene, transcript or protein in said neural stem cell decreases as compared to a comparable isolated neural stem cell not contacted with said compound. In another embodiment of the methods described above, the activity of at least one gene, transcript or protein in said neural stem cell increases as compared to a comparable isolated neural stem cell not contacted with said compound. In another embodiment of the methods described above, the disease is a neurodegenerative disorder. In a particular embodiment, the disease is Parkinson's, Alzheimer's, Schizophrenia, or Amyotrophic lateral sclerosis.

Provided herein are methods of screening a compound for use in treatment or prevention of a disease comprising: contacting an isolated neural stem cell with said compound; and detecting a change in the level of at least one transcript or protein in said neural stem cell. In one embodiment of the methods described above, the level of at least one transcript or protein in said neural stem cell decreases as compared to a comparable isolated neural stem cell not contacted with said compound. In another embodiment of the methods described above, the level of at least one transcript or protein in said neural stem cell increases as compared to a comparable isolated neural stem cell not contacted with said compound. In another embodiment of the methods described above, the disease is a neurodegenerative disorder. In another embodiment of the methods described above, the disease is Parkinson's, Alzheimer's, Schizophrenia, or Amyotrophic lateral sclerosis.

One embodiment provided herein describes a method of treating a neurological disorder in a mammal in need thereof comprising administering at least one neural stem cell to said mammal, wherein the cell is immune privileged. In another embodiment, said mammal is a mouse, rat, pig, dog, monkey, orangutan or ape. In another embodiment, said mammal is a human.

In one embodiment, said mammal in need thereof has one or more symptoms associated with a neurological disorder. In another embodiment, said one or more symptoms is selected from the group consisting of rigidity, akinesia, balance impairment, tremor, gait disorder, maldispositional gait, dementia, excessive swelling (edema), muscle weakness, atrophy in the lower extremity, movement disorder (chorea), muscle rigidity, a slowing of physical movement (bradykinesia), loss of physical movement (akinesia), forgetfulness, cognitive (intellectual) impairment, loss of recognition (agnosia), impaired functions such as decision-making and planning, hemifacial paralysis, sensory deficits, numbness, tingling, painful paresthesias in the extremities, weakness, cranial nerve palsies, difficulty with speech, eye movements, visual field defects, blindness, hemorrhage, exudates, proximal muscle wasting, dyskinesia, abnormality of tonus in limb muscles, decrease in myotony, incoordination, wrong indication in finger-finger test or finger-nose test, dysmetria, Holmes-Stewart phenomenon, incomplete or complete systemic paralysis, optic neuritis, multiple vision, ocular motor disturbance such as nystagmus, spastic paralysis, painful tonic seizure, Lhermitte syndrome, ataxia, mogilalia, vesicorectal disturbance, orthostatic hypotension, decrease in motor function, bed wetting, poor verbalization, poor sleep patterns, sleep disturbance, appetite disturbance, change in weight, psychomotor agitation or retardation, decreased energy, feelings of worthlessness or excessive or inappropriate guilt, difficulty thinking or concentrating, recurrent thoughts of death or suicidal ideation or attempts, fearfulness, anxiety, irritability, brooding or obsessive rumination, excessive concern with physical health, panic attacks, and phobias. In another embodiment, said neurological disorder is Parkinson's disease, Alzheimer's disease, Huntington's disease, Amyotrophic lateral sclerosis, Friedreich's ataxia, Lewy body disease, spinal muscular atrophy, multiple system atrophy, dementia, schizophrenia, paralysis, multiple sclerosis, spinal cord injuries, brain injuries (e.g., stroke), cranial nerve disorders, peripheral sensory neuropathies, epilepsy, prion disorders, Creutzfeldt-Jakob disease, Alper's disease, cerebellar/spinocerebellar degeneration, Batten disease, corticobasal degeneration, Bell's palsy, Guillain-Barre Syndrome, Pick's disease, and autism.

Also provided herein, in one embodiment, is a method of treating a neurological disorder in a mammal in need thereof comprising administering at least one neural stem cell to said mammal, wherein the cell is immune privileged and derived from trophoblast tissue. In another embodiment, the immune privileged cell has low levels of CD33 expression. In another embodiment, the immune privileged cell has low levels of CD133 expression. In another embodiment, the neuronal progenitor stem cell does not elicit an immune response. In another embodiment, the neuronal progenitor stem cell does not form a tumor. In another embodiment, the neural stem cell expresses transcripts for one or more of Cdx2, Nanog, nestin, Oct-4, neurofilament, NgN3, Neo-D, MAP-2, CD133, RARβ, RXRα, RXRβ, CRABP-2, CRBP-1, RALDH-2 or RALDH-3.

In another embodiment, the method further comprises administering said one or more neural stem cell into the brain of a mammal, wherein the cell differentiates into a neuron. In another embodiment, said administering comprises injecting or implanting. In another embodiment, said neuron is a dopaminergic neuron, glutaminergic neuron, serotonergic neuron, or GABAergic (gamma aminobutyric acid) neuron. In another embodiment, said progenitor cell is pre-induced with an induction drug prior to said administering.

Also provided herein in one embodiment is a method of inducing or promoting a stem cell to differentiate into a cell with neuronal characteristics, comprising: (a) contacting the stem cell with an induction drug; (b) modulating one or more proteins with the induction drug in the stem cell, wherein the one or more proteins comprise wingless-type MMTV integration site 2B (Wnt2B), frizzled family receptor 6 (Fzd6), disheveled 3 (Dvl3), frequently rearranged in advanced T-cell lymphomas 1 (FRAT1), glycogen synthase kinase 3 beta (GSK3β), histone deacetylase 6 (HDAC6), β-catenin, guanine nucleotide binding protein subunit alpha 11 Gq class (Gα$_{q/11}$), guanine nucleotide binding protein beta (Gβ), retinoid X receptor alpha (RXRα), retinoic acid receptor beta (RARβ), glutamate receptor 1 (GLuR1), phosphoinositide-3-kinase (PI3K), rac-alpha serine/threonine-protein kinase (AKt1), rac-beta serine/threonine-protein kinase (AKt2), rac-gamma serine/threonine-protein kinase (AKt3), mammalian target of rapamycin (mTOR), Eukaryotic translation initiation factor 4E-binding protein (EIF4EBP), cAMP responsive element binding protein 1 (CREB1), tyrosine hydroxylase (TH), phospholipase C beta (PLC-β), Phosphatidylinositol 4,5-bisphosphate (PIP2), calcium/calmodulin-dependent protein kinase II inhibitor 2 (CaM-KII), eukaryotic translation initiation factor 4B (EIF4B), parkin, alpha-synuclein (SNCA), tublin, calcineurin, Collapsin response mediator protein 2 (CRMP-2), nuclear factor of activated T-cells (NFAT1), importin, lymphoid enhancer-binding factor 1 (LEFT), Pituitary homeobox 2 (Pitx2), myocyte enhancer factor 2A (MEF2A), or E1A binding protein p300 (EP300); and (c) inducing or promoting the stem cell to differentiate into a cell with neuronal characteristics.

In one embodiment, the stem cell is a mammalian trophoblast stem cell. In another embodiment, the stem cell is a mammalian embryonic stem cell. In another embodiment, the stem cell is a mammalian induced pluripotent stem cell. In another embodiment, wherein the stem cell is an endodermal, mesodermal, ectodermal or mesenchymal stem cell. In another embodiment, the stem cell is from a mouse, rat, human, chimpanzee, gorilla, dog, pig, goat, dolphin, or cow. In another embodiment, the stem cell is from a human. In another embodiment, the stem cell is a human trophoblast stem cell. In another embodiment, the cell with neuronal characteristics is a neural stem cell (NSC), dopamine producing cell, dopaminergic neuron, unipolar neuron, bipolar neuron, multipolar neuron, pyramidal cell, Purkinje cell, and anterior horn cell, basket cell, betz cell, Renshaw cell, granule cell, or medium spiny cell.

In one embodiment, the induction drug comprises retinoic acid, nicotinamide or beta-mercaptoethanol, vitamin B12, heparin, putrescine, biotin, or Fe2+, butylated hydroxyanisole, valproic acid, forskolin, 5-azacytidine, indomethacin, isobutylmethylxanthine, or insulin. In another embodiment, the modulating comprises increasing the activity of at least one of the one or more proteins. In another embodiment, the modulating comprises increasing the expression of at least one of the one or more proteins. In another embodiment, increasing expression comprises increasing the amount of mRNA encoding at least one of the one or more proteins or increasing the amount of at least one of the one or more proteins translated from an mRNA. In another embodiment, the modulating comprises decreasing the activity of at least one of the one or more proteins. In another embodiment, the modulating comprises decreasing the expression of at least one of the one or more proteins. In another embodiment, decreasing expression comprises decreasing the amount of mRNA encoding at least one of the one or more proteins or decreasing the amount of at least one of the one or more proteins translated from an mRNA.

Also described herein the method of inducing or promoting a stem cell to differentiate into a cell with neuronal characteristics, wherein the neuronal characteristics comprises the expression of dopamine, subunits of the glutamate N-methyl D-aspartate (NMDA) receptor, synapsin I, a-calcium channel marker, growth associated protein 43 (GAP-43), voltage-dependent K+ channel, a voltage-dependent Ca+ channel, or a voltage-dependent Na+ channel.

In one embodiment, the method of inducing or promoting a stem cell to differentiate into a cell with neuronal characteristics, comprises modulating one or more proteins with the induction drug in the stem cell, wherein the one or more proteins is Wnt2B. In another embodiment, Wnt2B is activated. In another embodiment, Wnt2B is inactivated. In another embodiment, Wnt2B is activated and then inactivated. In another embodiment, Wnt2B is inactivated and then activated. In another embodiment, Wnt2B promotes differentiation or proliferation of the stem cell. In another embodiment, Wnt2B promotes or induces dopamine expression.

In one embodiment, the method of inducing or promoting a stem cell to differentiate into a cell with neuronal characteristics, comprises modulating one or more proteins with the induction drug in the stem cell, wherein the one or more proteins is GSK3β. In another embodiment, GSK3β is activated. In another embodiment, GSK3β is inactivated. In another embodiment, GSK3β is activated and then inactivated. In another embodiment, GSK3β is inactivated and then activated. In another embodiment, GSK3β promotes differentiation or proliferation of the stem cell. In another embodiment, GSK3β modulates microtubule assembly.

In one embodiment, the method of inducing or promoting a stem cell to differentiate into a cell with neuronal characteristics, comprises modulating one or more proteins with the induction drug in the stem cell, wherein the one or more proteins is CREB1. In another embodiment, CREB1 is activated. In another embodiment, CREB1 is inactivated. In another embodiment, CREB1 is activated and then inactivated. In another embodiment, CREB1 is inactivated and then activated. In another embodiment, CREB1 promotes differentiation or proliferation of the stem cell. In another embodiment, CREB1 promotes or induces dopamine expression.

In one embodiment, the method of inducing or promoting a stem cell to differentiate into a cell with neuronal characteristics, comprises modulating one or more proteins with the induction drug in the stem cell, wherein the one or more proteins is CaMKII. In another embodiment, CaMKII is activated. In another embodiment, CaMKII is inactivated. In another embodiment, CaMKII is activated and then inactivated. In another embodiment, CaMKII is inactivated and then activated. In another embodiment, CaMKII promotes differentiation or proliferation of the stem cell. In another embodiment, CaMKII modulates microtubule assembly.

In one embodiment, the method of inducing or promoting a stem cell to differentiate into a cell with neuronal characteristics, comprises modulating one or more proteins with the induction drug in the stem cell, wherein the one or more proteins is MAPT. In another embodiment, MAPT is activated. In another embodiment, MAPT is inactivated. In another embodiment, MAPT is activated and then inactivated. In another embodiment, MAPT is inactivated and then activated. In another embodiment, MAPT promotes differentiation or proliferation of the stem cell. In another embodiment, MAPT modulates microtubule assembly.

Provided herein in one embodiment is a method of inducing or promoting a stem cell to differentiate into a cell with reduced immunogenicity, comprising: (a) contacting the stem cell with an induction drug; (b) modulating one or more proteins with the induction drug in the stem cell, wherein the one or more proteins comprise Wnt2B, Fzd6, Dvl3, FRAT1, GSK3β, HDAC6, β-catenin, $G\alpha_{q/11}$, Gβ, RXRα, RARβ, GLuR1, PI3K, AKt1, AKt2, AKt3, mTOR, EIF4EBP, CREB1, TH (tyrosine hydroxylase), PLC-β, PIP2, CaMKII, EIF4B, parkin, SNCA, tublin, calcineurin, CRMP-2, NFAT1, importin, LEFT, Pitx2, MEF2A, or EP300; and (c) inducing or promoting the stem cell to differentiate into a cell with reduced immunogenicity.

In one embodiment, the stem cell is a mammalian trophoblast stem cell. In another embodiment, the stem cell is a mammalian embryonic stem cell. In another embodiment, the stem cell is a mammalian induced pluripotent stem cell. In another embodiment, wherein the stem cell is an endodermal, mesodermal, ectodermal or mesenchymal stem cell. In another embodiment, the stem cell is from a mouse, rat, human, chimpanzee, gorilla, dog, pig, goat, dolphin, or cow. In another embodiment, the stem cell is from a human. In another embodiment, the stem cell is a human trophoblast stem cell.

Described herein in one embodiment is the method of inducing or promoting a stem cell to differentiate into a cell with reduced immunogenicity, wherein the cell with reduced immunogenicity is a neural stem cell (NSC), dopamine producing cell, dopaminergic neuron, unipolar neuron, bipolar neuron, multipolar neuron, pyramidal cell, Purkinje cell, and anterior horn cell, basket cell, betz cell, Renshaw cell, granule cell, or medium spiny cell. In another embodiment, the cell with reduced immunogenicity does not induce an immune response or can inhibit an immune response. In another embodiment, the cell with reduced immunogenicity does not induce an immune response or can inhibit an immune response by a T cell, B cell, macrophage, microglia cell, mast cell, or NK cell.

In one embodiment, the method of inducing or promoting a stem cell to differentiate into a cell with reduced immunogenicity comprises contacting the stem cell with an induction drug, wherein the induction drug comprises retinoic acid, nicotinamide or beta-mercaptoethanol, vitamin B12, heparin, putrescine, biotin, or Fe2+, butylated hydroxyanisole, valproic acid, forskolin, 5-azacytidine, indomethacin, isobutylmethylxanthine, or insulin.

In one embodiment, the method of inducing or promoting a stem cell to differentiate into a cell with reduced immunogenicity comprises modulating one or more proteins with the induction drug in the stem cell, wherein modulating comprises increasing the activity of at least one of the one or more proteins. In another embodiment, said modulating comprises increasing the expression of at least one of the one or more proteins. In another embodiment, increasing expression comprises increasing the amount of mRNA encoding at least one of the one or more proteins or increasing the amount of at least one of the one or more proteins translated from an mRNA. In another embodiment, said modulating comprises decreasing the activity of at least one of the one or more proteins. In another embodiment, said modulating comprises decreasing the expression of at least one of the one or more proteins. In another embodiment, decreasing expression comprises decreasing the amount of mRNA encoding at least one of the one or more proteins or decreasing the amount of at least one of the one or more proteins translated from an mRNA.

In one embodiment, the method of inducing or promoting a stem cell to differentiate into a cell with reduced immunogenicity further comprises inducing or promoting the stem cell to differentiate into a cell with neuronal characteristics, wherein the neuronal characteristics comprises the expression of dopamine, subunits of the glutamate NMDA receptor, synapsin I, a-calcium channel marker, GAP-43, voltage-dependent K+ channel, a voltage-dependent Ca+ channel, or a voltage-dependent Na+ channel.

In one embodiment, the method of inducing or promoting a stem cell to differentiate into a cell with reduced immunogenicity comprises modulating one or more proteins with the induction drug in the stem cell, wherein the one or more proteins is NFAT. In another embodiment, NFAT is activated. In another embodiment, NFAT is inactivated. In another embodiment, NFAT is activated and then inactivated. In another embodiment, NFAT is inactivated and then activated. In another embodiment, NFAT promotes differentiation or proliferation of the stem cell. In another embodiment, NFAT modulates microtubule assembly.

Also described herein is a method of inducing or promoting a human trophoblast stem cell to differentiate into a tNSC (trophoblast neural stem cell) with reduced immunogenicity or that can inhibit an immune response, comprising: (a) contacting the human trophoblast stem cell with an induction drug; (b) modulating one or more proteins with the induction drug in the stem cell, wherein the one or more proteins comprise Wnt2B, Fzd6, Dvl3, FRAT1, GSK3β, HDAC6, β-catenin, $G\alpha_{q/11}$, Gβ, RXRα, RARβ, GLuR1, PI3K, AKt1, AKt2, AKt3, mTOR, EIF4EBP, CREB1, TH (tyrosine hydroxylase), PLC-β, PIP2, CaMKII, EIF4B, parkin, SNCA, tublin, calcineurin, CRMP-2, NFAT1, importin, LEFT, Pitx2, MEF2A, or EP300; and (c) inducing or promoting the human trophoblast stem cell to differentiate into a tNSC.

In one embodiment, the method of inducing or promoting a human trophoblast stem cell to differentiate into a tNSC (trophoblast neurological stem cell) with reduced immunogenicity or that can inhibit an immune response, comprises contacting the human trophoblast stem cell with an induction drug, wherein the induction drug comprises retinoic acid, nicotinamide or beta-mercaptoethanol, vitamin B12, heparin, putrescine, biotin, or Fe2+, butylated hydroxyanisole, valproic acid, forskolin, 5-azacytidine, indomethacin, isobutylmethylxanthine, or insulin. In another embodiment, the tNSC does not induce an immune response or can inhibit an immune response by an immune cell. In another embodiment, the immune cell is a T cell, B cell, macrophage, microglia cell, mast cell or NK cell.

Also described herein is a method of inhibiting a tumor cell comprising: contacting the tumor cell with a compound; modulating aryl hydrocarbon receptor (AhR) in the tumor cell; and inhibiting the tumor cell by the modulation. Additionally described herein is a method of decreasing tumor cell growth comprising: contacting the tumor cell with a therapeutic agent; modulating AhR in the tumor cell; and decreasing growth in the tumor cell by the modulation. In one embodiment modulating AhR comprises inhibiting AhR protein activity in said cell. In another embodiment modulating AhR comprises inhibiting AhR gene expression in said cell. In another embodiment the tumor cell is killed. In another embodiment the tumor is a lung, breast, colon, brain, bone, liver, prostate, stomach, esophageal, skin or leukemia tumor. In another embodiment tumor is a solid or liquid tumor. In another embodiment AhR is modulated with an AhR agonist. In another embodiment AhR is modulated with an AhR antagonist. In another embodiment AhR is modulated with a compound that has anti-estrogenic activity. In another embodiment AhR is modulated with a compound that has anti-androgenic activity. In another embodiment the tumor cell is in a mammal. In another embodiment the tumor cell is in a human.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF FIGURES

The novel features of the invention are set forth with particularity in the appended claims. A better understanding of the features and advantages described herein will be obtained by reference to the following detailed description that sets forth illustrative embodiments, in which the principles of the invention are utilized, and the accompanying drawings of which:

FIG. 1 shows characteristics of pluripotence and renewal in hTS cells. (1a) hTS cells express specific genes of both inner cell mass (ICM) and trophectoderm measured by RT-PCR analysis. (1b) Illustrates expression and intracellular localization of specific stage embryonic antigen (SSEA)-1, -3, and -4 as visualized by immunocytochemical staining (darkened spots). In hTS cells (upper panels), SSEA-1 is expressed mostly in the cytoplasm (left upper panel), SSEA-3 is expressed in the nucleus (middle upper panel), and SSEA-4 is expressed in both the cytoplasm and membrane (upper right panel). These SSEA-expressed cells were histologically identical to the ectopic villous cytotrophoblasts (lower panels). (1c) Unchanged telomere length at 3rd and 7th passages of hTS cells culture measured by the Terminal Restriction Fragment (TRF) Southern blot analysis (upper and lower panels). (1d) Venn diagram illustrates the microarray analysis of gene expression in hTS (859 genes) and trophoblast associated placenta derived mesenchymal stem cells (PDMS cells) (2449 genes). A total of 2,149 and 3,730 genes expressed in the hTS cells and trophoblast associated PDMS cells (fold change >2-fold). (1e) Illustrates results from reverse transcription polymerase chain reaction (RT-PCR) analysis of transcription factor expression in response to different concentrations of leukemia inhibitory factor (LIF) (i.e., 500, 250, 125 U/ml; U: units/ml, Actin: β-actin as the control sample). Withdrawal of LIF suppresses Oct4 and Sox2, but overexpresses Nanog and Cdx2 in hTS cells. (1f) Flow cytometric analysis of LIF (125 U/ml) promoted expressions of Nanog, Cdx2, Sox2, and Oct4 in hTS cells (left panel). Histogram shows a negative dose-dependent manner in Nanog and Cdx2 (left panels) and a positive dose-dependent manner in Oct4 and Sox2 (right panel). (1g) A diagram of the physiological distribution of LIF levels in the different segments of fallopian tubes in women, specifically the physiological reduction of LIF levels from ampulla toward isthmus in the fallopian tubes. The relative ratio of Oct4, Nanog and Sox2 to Cdx2 each show a dose-dependency in three different segments of the fallopian tube. (1h) Effect of different siRNAs to specific transcriptors Nanog and Cdx2 was analyzed by RT-PCR (left) and flow cytometric analyses (right) in hTS cells, illustrating a reciprocal relationship between Nanog and Cdx2 in the maintenance of pluripotency of hTS cells. Data indicated mean±SD for 3 assays. (1i) Histogram of gene intensity shows a homogeneous pattern in hTS cells, while PDMS cells show a biphasic pattern.

FIG. 5 illustrates the analysis of the transplantation of GFP-tagged tNSCs ($3\times10^6$) into Parkinson's Disease (PD) rats. (5a) Analysis of apomorphine induced rotation test; Group a (dark-shaded circles, n=4), which correlates to PD rats that received tNSCs transplantation, shows significant reduction in contralateral rotation from 3 weeks to 12 weeks postimplantation; Group b (light-shaded circles, n=4), which correlate to PD rats that received 5-day RA-treated hTS cells, shows an initial significant improvement at 6 weeks postimplantation but this improvement decreased gradually through week 12; and Group c (triangles, n=4), which correlates to the untreated PD rats as the control group, shows no improvement. Statistic analysis by repeated measure ANOVA: p value=0.001 and LSD post hoc comparisons after repeated measure ANOVA in between two groups: p=0.037 (group a vs. c) and p=0.008 (group b vs. c) at 6 weeks; p=0.019 (group a vs. c) at 9 weeks; p=0.005 (group a vs. c) and p=0.018 (group a vs. b) at 12 weeks. * indicates p<0.05. (5b) Illustrates TH-positive immunohistochemical staining in the lesioned striatum of Group a at 18 weeks postimplantation (upper panel); immunofluorescence microscopic analysis indicates that the immunofluorescent GFP-tagged tNSCs still persisted in the lesioned striatum with a patchy formation at the injection site (lower panel). (5c) illustrates TH-positive neurons regenerated in the lesioned substantia nigra compacta (SNC) of Group a at 18 weeks postimplantation (upper panel); amplification of the terminal region is shown (lower left panel), Scale bar: 100 μm; immunofluorescence microscopic analysis indicates that the immunofluorescent GFP-tagged tNSCs persisted in a scattered distribution (lower right panel, arrows indicating GFP-tagged tNSCs). (5d) Illustrates immunohistochemical staining of Group b at 18 weeks postimplantation: no TH-positive cells were found in the left lesioned striatum (str, upper panel) or subthalamic nucleus (stn, lower panel). (5e) Illustrates immunohistochemical staining of Group c at 18 weeks postimplantation: no TH-stained cells were found in the left lesioned striatum (str, upper panel) or lesioned SNC (lower panel); arrow indicates implanting needle track.

FIG. 10 illustrates that the histological analysis of transplantation of hTS cells into the male severe combined immune deficiency (SCID) mice subcutaneously caused only minor chimeric reaction with myxoid-like bizarre cells at 6-8 weeks postimplantation (filled, black arrows designate bizarre cells; unfilled arrows designate muscle fiber; "NT" designates needle track).

FIG. 12 illustrates certain media that were used for cell differentiation.

FIG. 13 illustrates PCR primers (SEQ ID NOS 11-48, respectively, in order of appearance) that were used for RT-PCR.

FIG. 18 illustrates that effect of LIF on Nanog expression. (18a) illustrates LIF promoted expressions of Nanog. Left panels illustrate that Nanog expression is significantly suppressed in a negative dose-dependent fashion by flow cytometric analysis in hTS cells. Data indicated mean±SD for three assays. *p<0.01 (Student's t test, n=3). Right panel illustrates relative Nanog expression when hTS cells are preincubated with RA (10 µM) overnight followed by treating LIF with different levels (i.e., 125, 250 and 500 U/ml each) for 1-day. (18b) illustrates RA induction (1 day incubation, 10 µM) in hTS cells stimulated expression of Nanog and Oct4, but not Cdx2 and Sox2 by flow cytometric analysis.

FIG. 19 illustrates the assessment of behavioral improvements in elderly PD rats. (19a) illustrates immunohistochemistry of TH+ neurons on a series of brain sections (30 µm) at 12 weeks postimplantation revealed that abundant newly regenerated TH-positive neurons appeared in the lesioned nigrostriatal pathway (left portion). In the SNC areas, the TH-positive neurons appeared in a feature with multiple outgrowths projecting from the cell body to form neuronal circuitries with the host tissue. The number of regenerated dopaminergic neurons in one rat accounted for 28.2% of the opposite normal side (n=5). (19b) The number of dopaminergic neurons in the lesioned SNC of a rat regenerated to 28.2% compared to the normal side.

illustrates hTS cells were transfected with the a DNA mixture of F1B-GFP plasmid construct to yield a success rate of over 95%; (20*c*) illustrates time course of RA induced production of eIF4B; (20*d*) illustrates activation of c-Src was inhibited by using eIF4B; (20*e*) illustrates IP analysis indicating that active c-Src binds directly to Stat3 (signal transducer and activator of transcription); (20*f*) illustrates c-Src siRNA inhibited expression of Stat3; (20*g*) illustrates Nanog expression was inhibited by Stst3 siRNA; and (20*h*) illustrates a scheme of the RA-induced c-Src/Stat3/Nanog pathway via subcellular c-Src mRNA localization in hTS cells.

Figure 21:
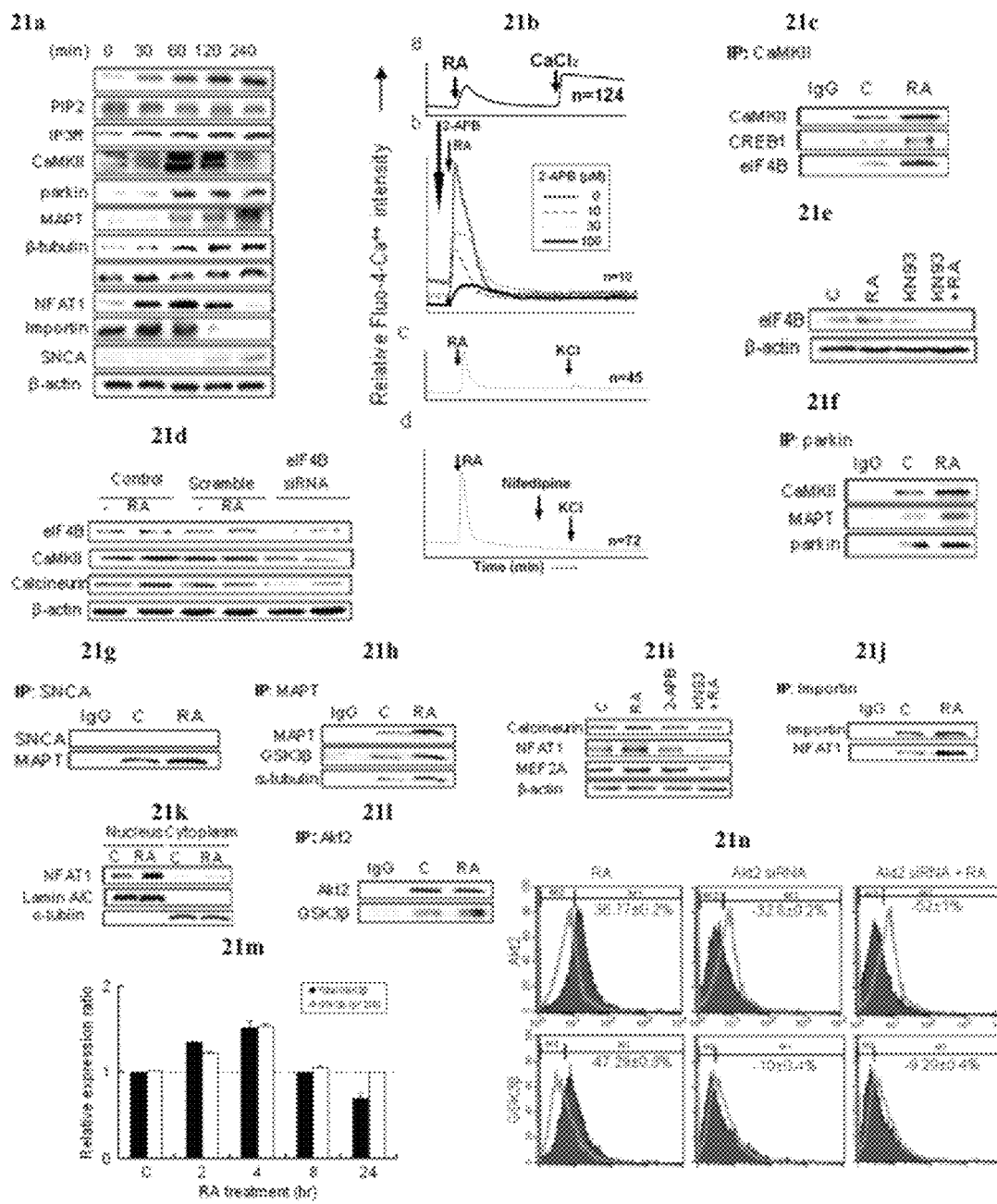

FIG. 21 illustrates activation of $G\alpha_{q/11}$ signaling pathway: (21*a*) illustrates expressions of $G\alpha_{q/11}$ pathway-related components after RA treatment (10 μM) over time by Western blots; (21*b*) illustrates real-time live cell imaging microscopy (Cell-R system, Olympus, Tokyo) in hTS cells which were cultured in the calcium-free medium and pre-loaded with Fluo4 (1 μM) in BSS buffer 20 min before RA treatment. (a) The RA-induced depletion of intracellular calcium was rescued by adding $CaCl_2$ (2 mM) with a SOCE pattern. (b) RA-induced intracellular calcium levels were inhibited by 2-APB (10 min) in a significant dose-dependent manner ($R^2$=0.8984). (c) After depletion of ER calcium, KCl (60 mM) enabled to activate L-type calcium channels. (d) KCl-dependent L-type calcium channels were blocked by inhibitor nifedipine (5 μM) after ER calcium depletion. n: total cells counted; (21*c*) illustrates that CaMKII directly interacted with CREB1 and eIF4B; (21*d*) illustrates eIF4B siRNA inhibited expressions of CaMKII, calcineurin, and eIF4B by Western blots; (21*e*) illustrates KN93 (1 μM, 2 hr) inhibited eIF4B expression by Western blots; (21*f*) illustrates parkin directly interacted with CaMKII and MAPT; (21*g*) illustrates SNCA directly interacted with MAPT; (21*h*) illustrates MAPT interacted with GSK3β and α-tubulin; (21*i*) illustrates 2-APB inhibited expressions of Calcineurin, NFAT1, and MEF2A by Western blots; (21*j*) illustrates direct interaction between Importin and NFAT1; (21*k*) illustrates RA stimulated NFAT1 nuclear translocation by fractional assay. Lamin A/C: nuclear marker and α-tubulin: cytoplasmic marker; (21*l*) illustrates Akt2 directly interacted with GSK3β; (21*m*) illustrates flow analysis of GSK3β expression in cells treated with RA for 4 hr (blank column) and for 24 hr (black column) with different antibodies revealed in dynamic changes. Data show mean±SD, n=3; (21*n*) illustrates flow cytometric analysis showed that Akt2 siRNA inhibited RA-induced GSK3β expression.

Figure 22:
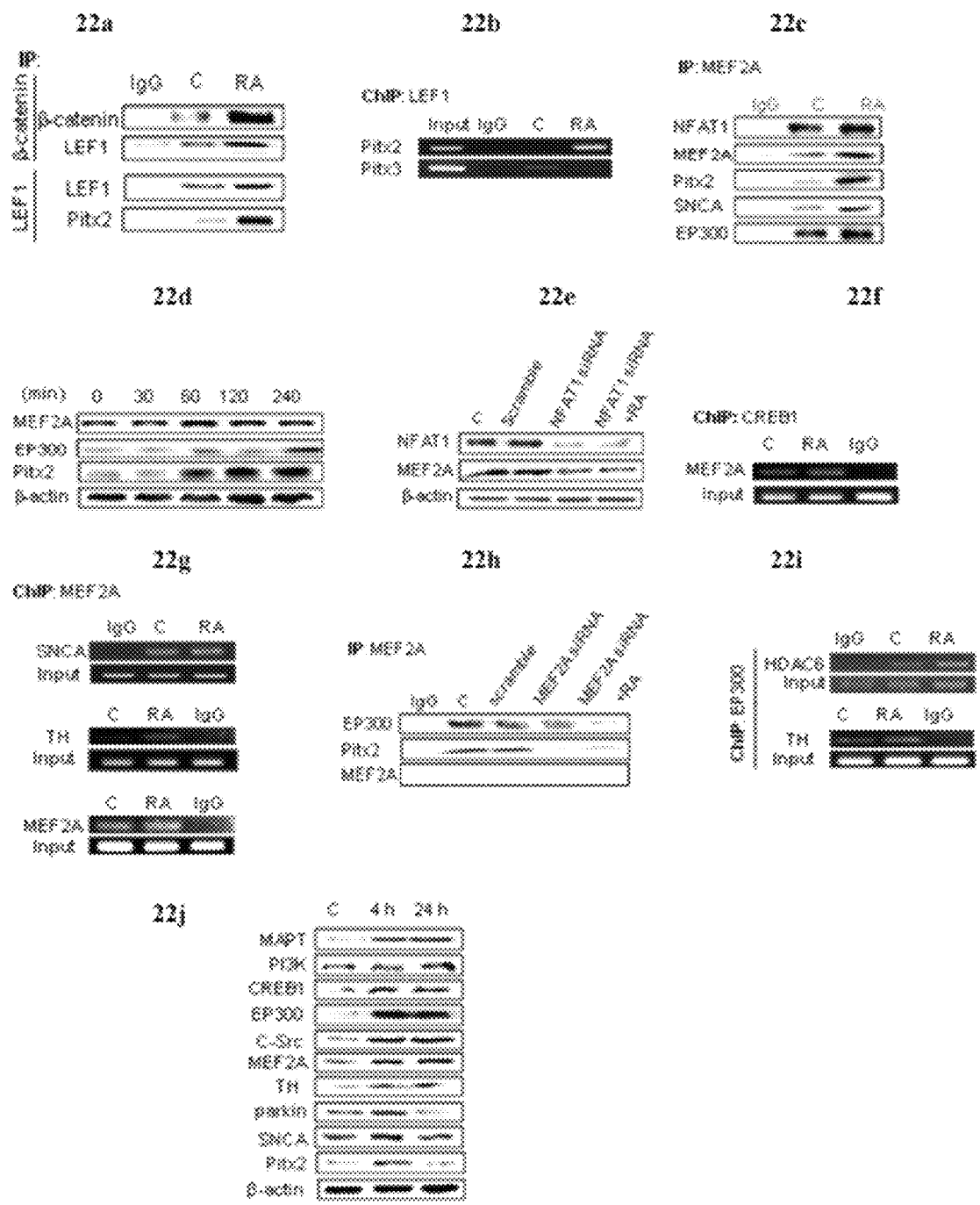

FIG. 22 illustrates formation of transcriptional complex: (22*a*) illustrates interaction between β-catenin and LEF1 (upper) and between LEF1 and Pitx2; (22*b*) illustrates LEF1 transcribed genes Pitx2 gene but not Pixt3 by RA treatment (4 hr); (22*c*) illustrates MEF2A directly interacted with NFAT1, MEF2A, Pitx2, SNCA, and EP300 by Western blots; (22*d*) illustrates RA induced production of MEF2A, EP300, and Pitx2 over time by Western blots; (22*e*) illustrates NFAT1 siRNA inhibited expression of MEF2A by Western blots; (22*f*) illustrates CREB1 targeted at the promoter of gene MEF2A; (22*g*) illustrates MEF2A transcribed genes SNCA (upper), TH (middle), and MEF2A itself (lower); (22*h*) illustrates MEF2A siRNA inhibited expressions of EP300, Pitx2, and MEF2A by Western blots; (22*i*) illustrates EP300 targeted at promoter of genes HDAC6 (upper) and TH (lower); (22*j*) illustrates identification of the various molecular activities at time points, 4 hr and 24 hr by Western blots. Abbreviation, IP: immunoprecipitation assay; ChIP: chromatin immunoprecipitation assay.

Figure 23:
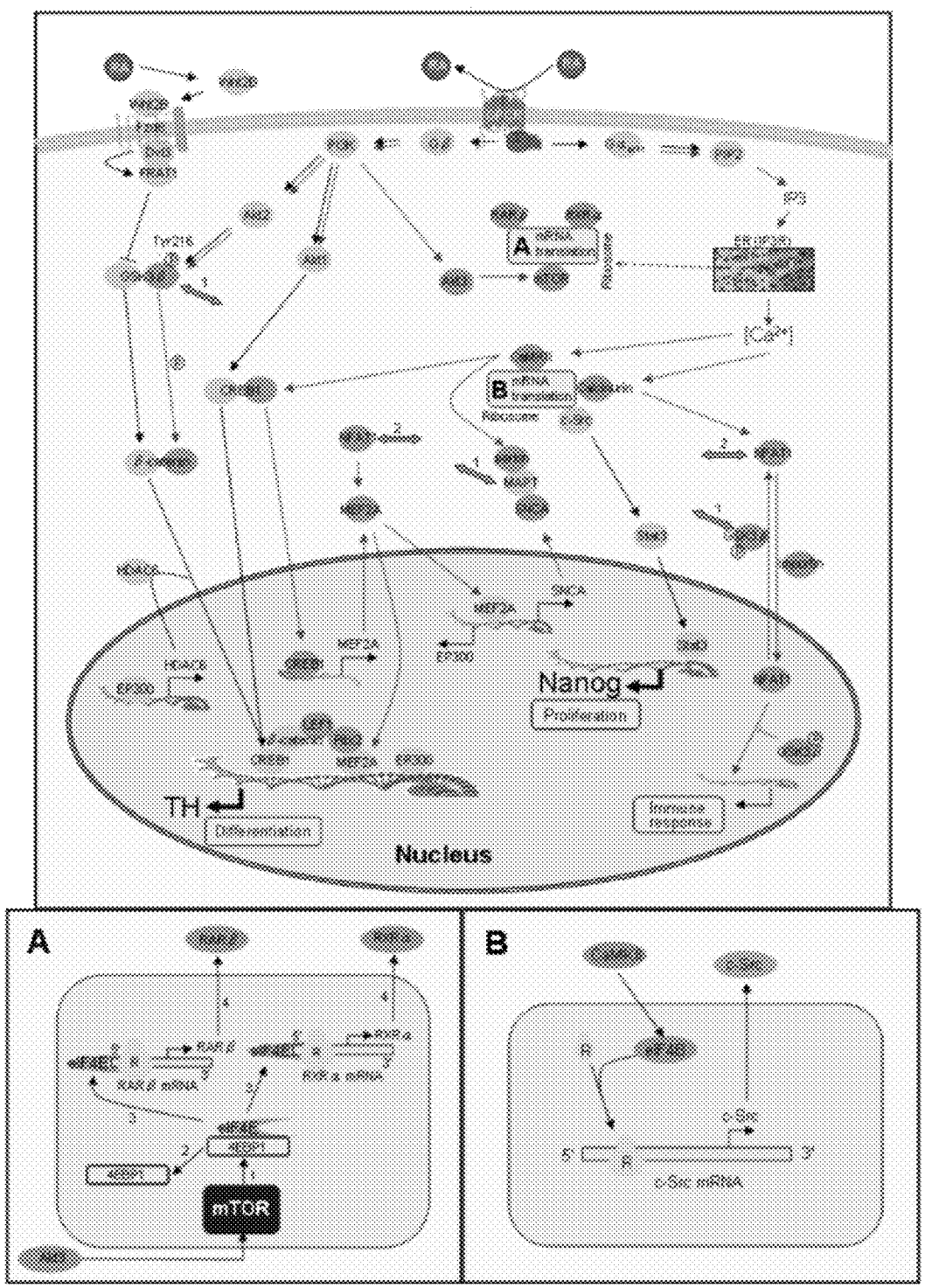

FIG. 23 illustrates the schematic regulatory networks of RA-induced neurogenesis in hTS cells (upper panel). Two mRNA translational machineries: the cap-dependent (left lower) and cap-independent (right lower). Grey line: the spatiotemporal signaling pathways; black line: the transcriptional pathways; double-headed arrow: molecule in a linkage to other pathway.

Figure 24:
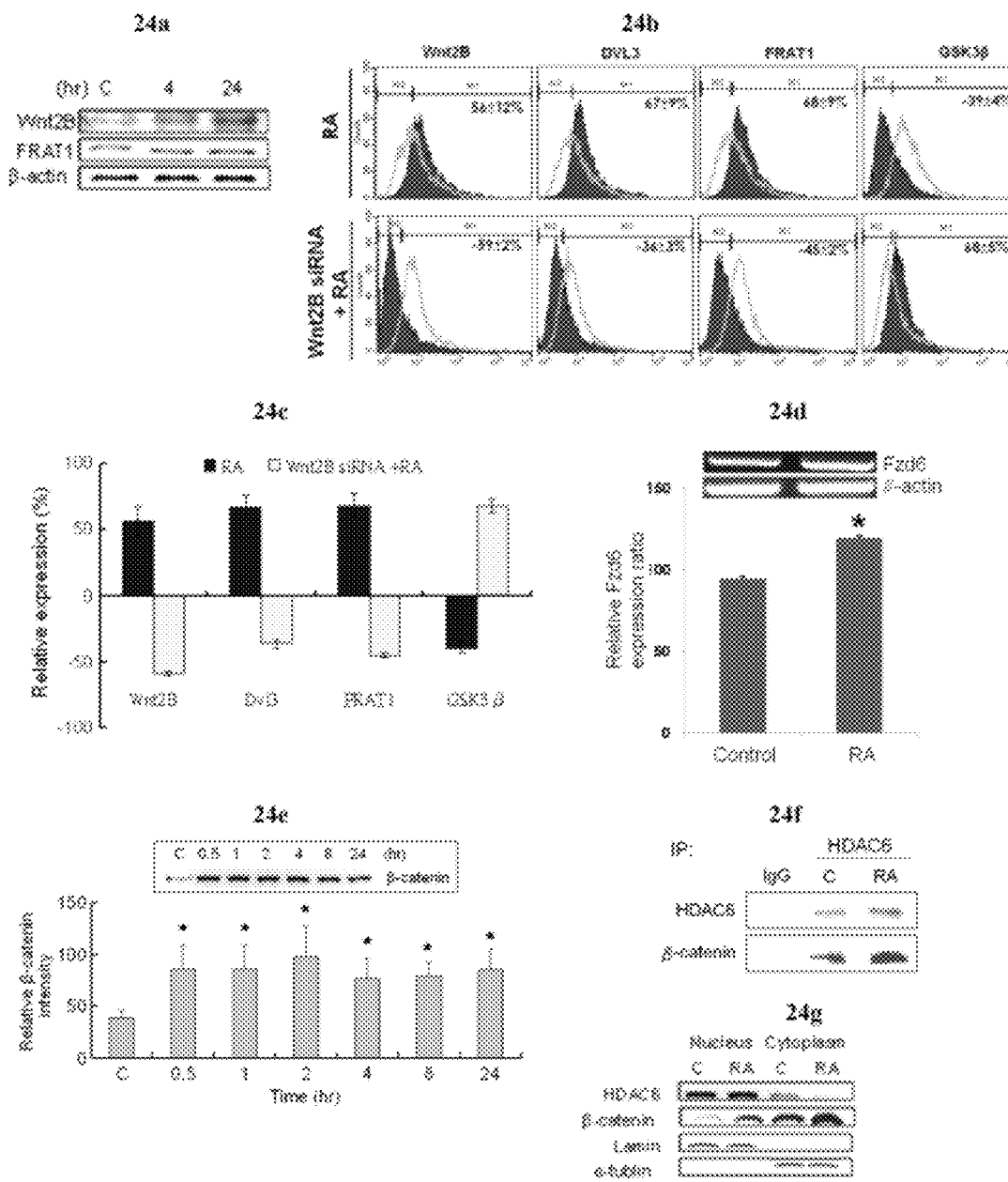

FIG. 24 illustrates that RA signaling promotes Wnt2B/Fzd6/β-catenin pathway: (24*a*) illustrates flow cytometry analysis indicating that RA (10 μM) induced significantly activations of Wnt2B, Dvl3, and FRAT1 but inhibited GSK3β overnight evidenced by inhibitory action of pre-treated Wnt2B siRNA. Data shows mean±SD; n=3; (24*b*) illustrates that increased Fzd6 mRNA expression by RA RT-PCR. Data shows mean±SD; n=3, *: p<0.05 by Student's test; (24*c*) illustrates RA induced changes of expression in β-catenin and HDAC6 over time by Western blots; (24*d*) illustrates that IP assay revealed a physical interaction between HDAC6 and β-catenin by overnight incubation with RA; (24*e*) illustrates RA induced nuclear/cytoplasmic translocation of β-catenin by fractionation assay after overnight incubation. Lamin and α-tubulin serve as nuclear and cytoplasmic markers, respectively; (24*f*) illustrates confocal immunofluorescence microscopy showing dynamic changes of the RA-induced β-catenin and HDAC6 indicated nuclear translocation of β-catenin at 30 min, which was inhibited by HDAC6 siRNA; (24*g*) illustrates that punctate β-catenin appeared in the synaptic regions at 5 min of RA treatment (arrow).

Figure 25:
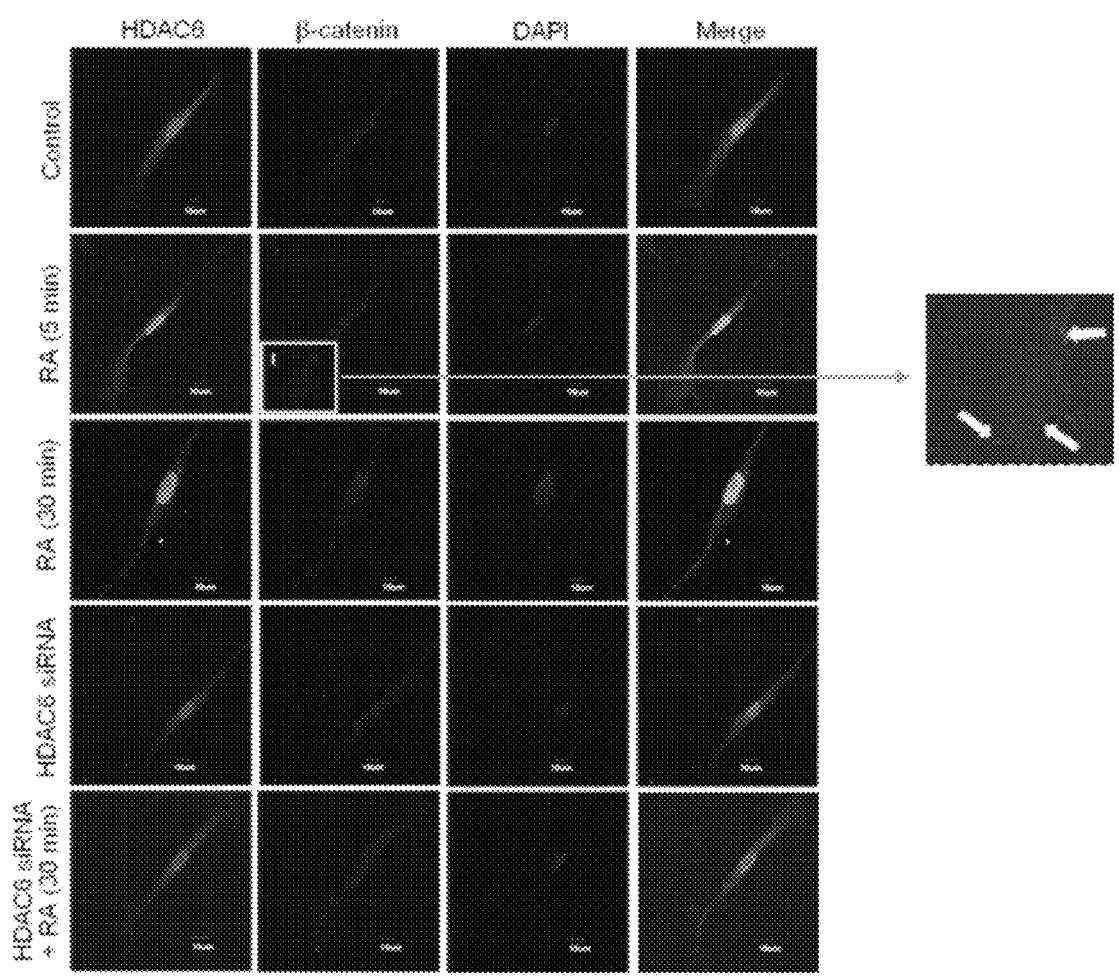

FIG. 25 illustrates confocal immunofluorescence microscopy analysis. In the presence of siRNA against HDAC6, nuclear localization of β-catenin was blocked.

Figure 26:
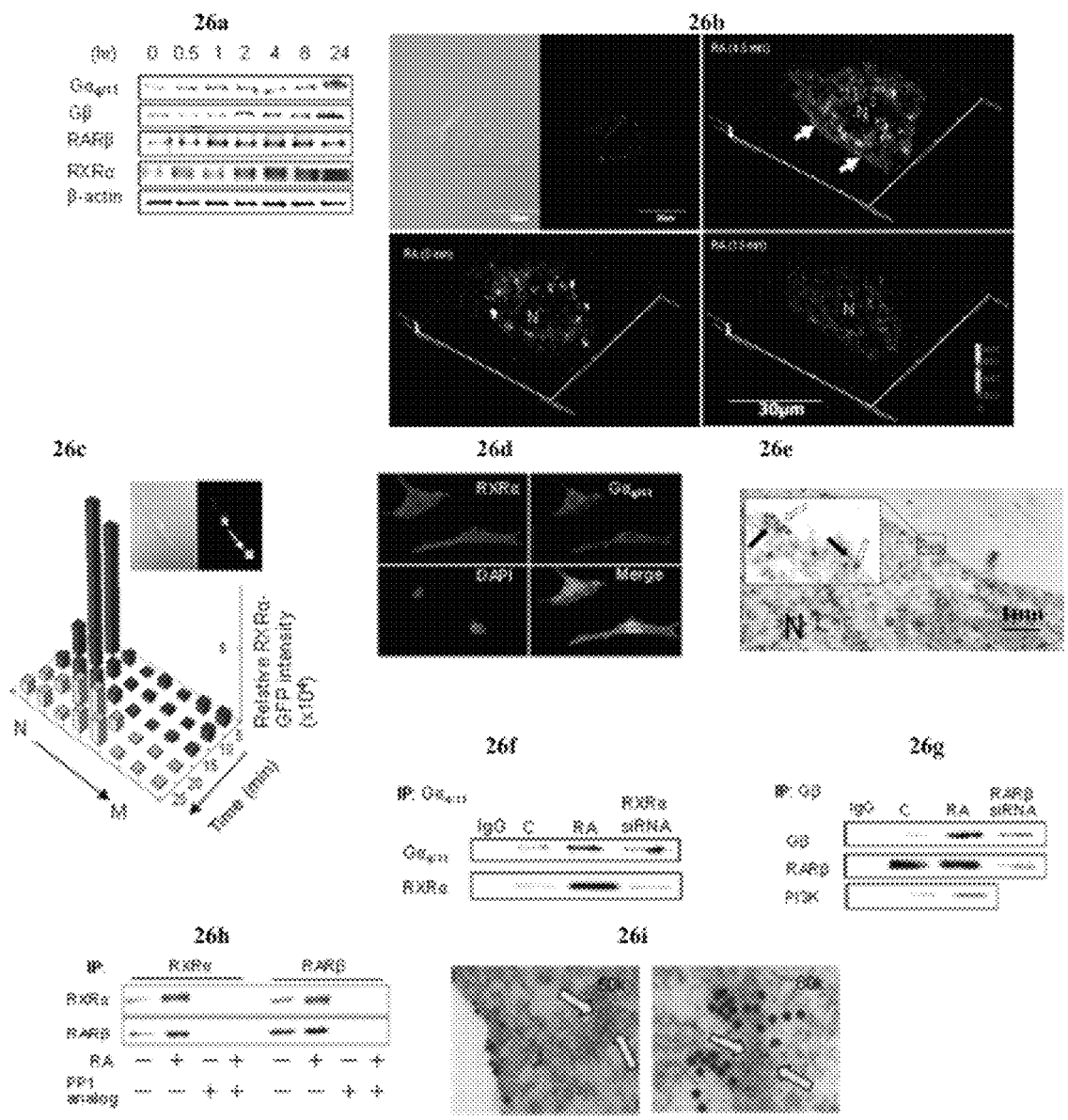

FIG. 26 illustrates molecular events at the cell membrane: (26*a*) illustrates RA induced productions of $G\alpha_{q/11}$, Gβ. RXRα, and RARβ over time by Western blots. β-actin as control; (26*b*) illustrates real-time confocal immunofluorescence microscopy analysis, revealing the movement of representative GFP-tagged RXRα from the perinuclear regions towards the cell membrane (arrow) after RA stimulation at 0, 4.5, and 13 min. No RXRα was visible in the nucleus. Normal phase contrast (left upper) and fluorescent image (right upper). Bar indicates 30 μm; (26*c*) illustrates a dynamic movement and changes in intensity of the relatively quantitative GFP-tagged RXRα from the nucleus (N) to the cell membrane (M) in time course. Normal phase contrast and fluorescent imaging show at upper right; (26*d*) illustrates that a representative imaging revealed co-expression of RXRα and $G\alpha_{q/11}$ at the cell membrane by RA at 5 min; (26*e*) illustrates double immunogold labeling of RXRα (6 μm; black arrow) and $G\alpha_{q/11}$ (20 μm; white arrow) at the cell membrane observed after RA treatment for 20 min. N: nucleus; (26*f*) illustrates RXRα siRNA inhabited the RA-induced interaction of $G\alpha_{q/11}$ and RXRα (24 hr); (26*g*) illustrates RARβ siRNA inhibited the RA-induced interaction of Gβ and RARβ as well as interaction of Gβ and PI3K (24 hr). IP: immunoprecipitation assay; IgG: negative control; C: positive control; (26*h*) illustrates IP assay analysis showing a selective c-Src inhibitor PP1 analog was able to prevent the formation of RXRα-RARβ heterodimer; (26*i*) illustrates anchorage of the RA-induced gold particle-tagged RXRα in the endoplasmic reticulum (ER) observed by double immunogold transmission electron microscopy.

Figure 27:
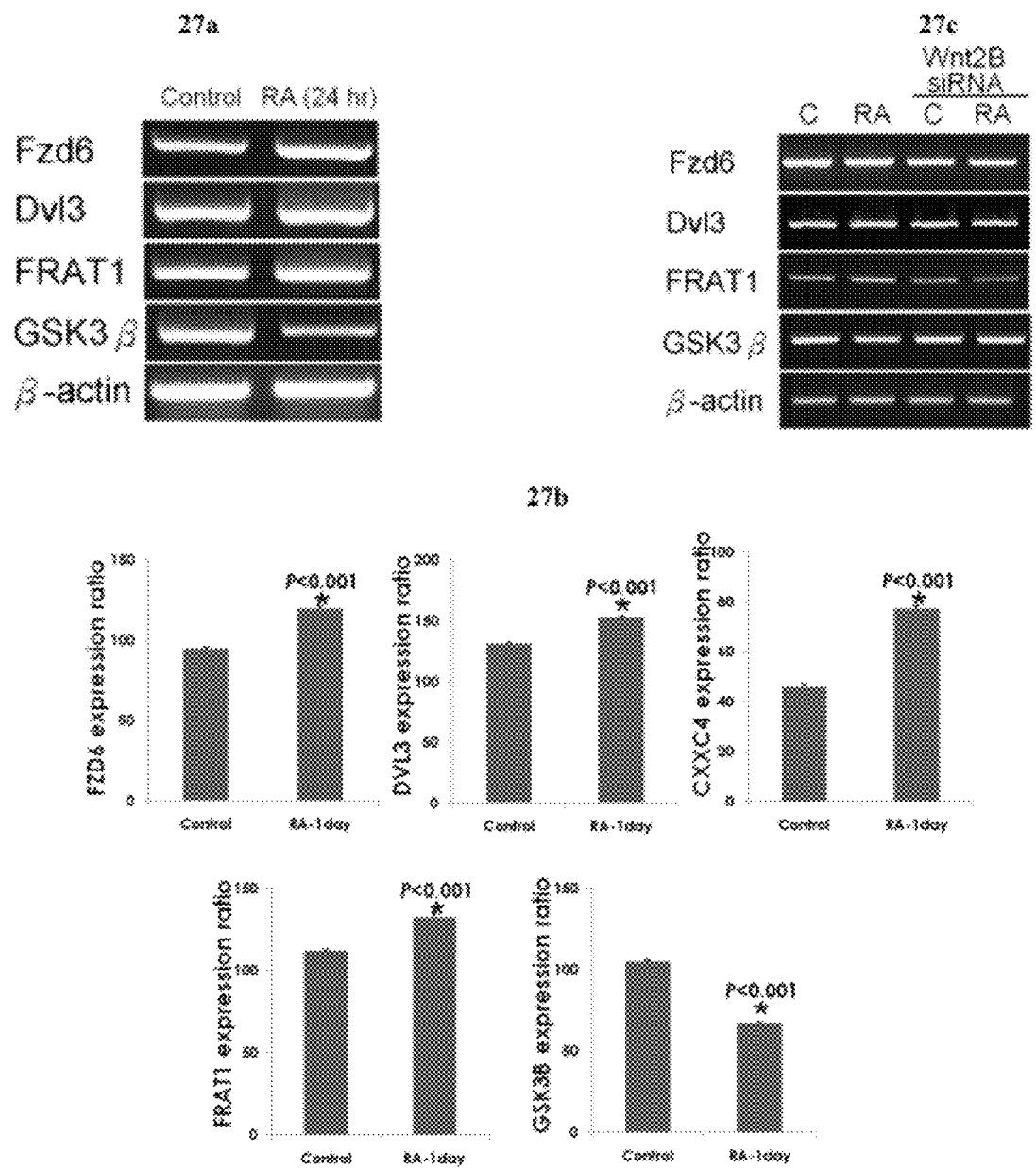

FIG. 27 illustrates that RA stimulates canonical Wnt2B pathway by RT-PCR; RA induced expressions of components of Wnt2B signaling pathway after overnight treatment (10 μM) in hTS cells, showing in a significant statistically;

Wnt2B siRNA inhibited the RA-induced components of Wnt2B pathway after overnight treatment.

Figure 28:
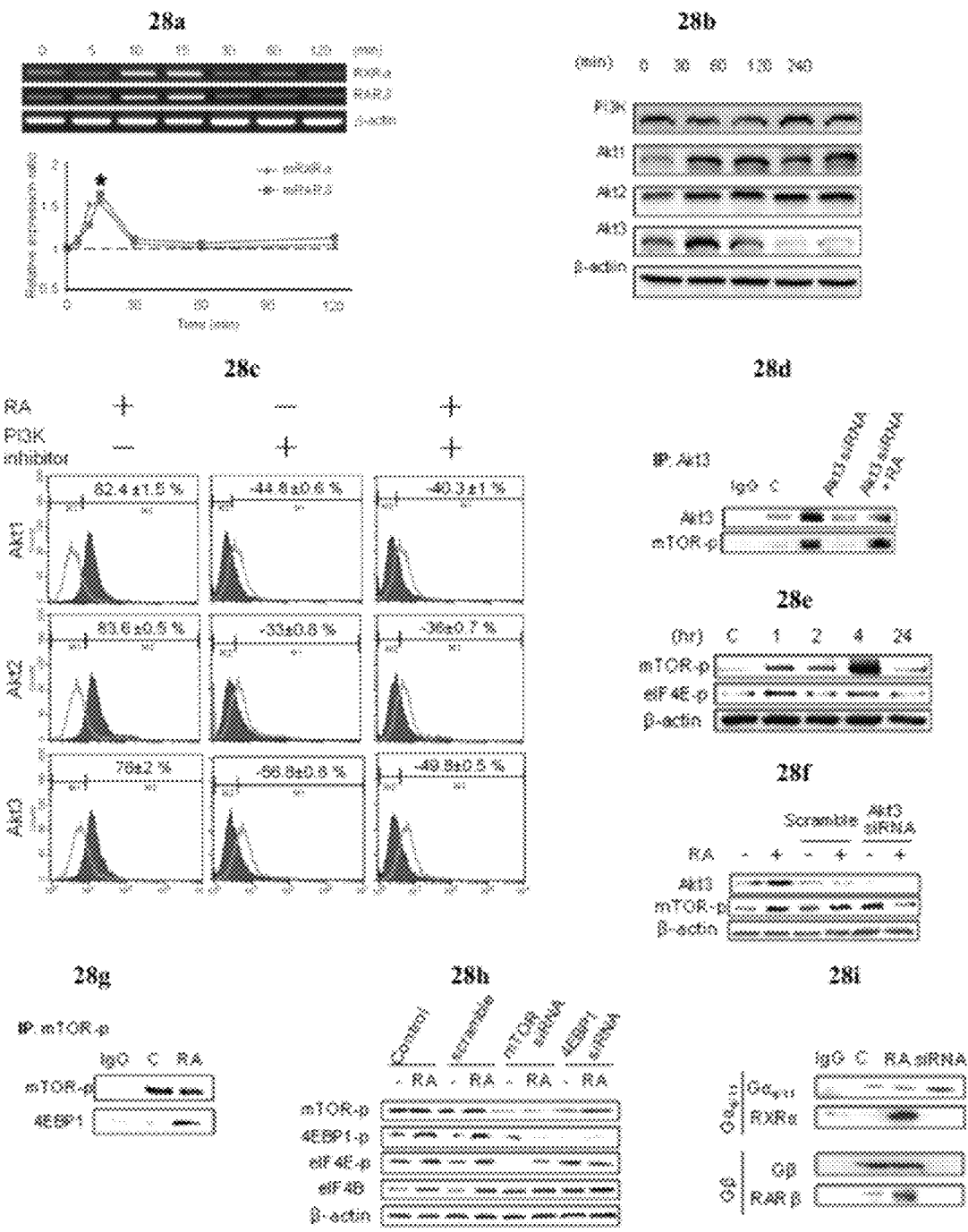

FIG. 28 illustrates local syntheses of RXRα and RARβ: (28a) illustrates that RA (10 μM) induced rapidly transient elevation of both RXRα mRNA and RARβ mRNA at 15 min by RT-PCR. Data show mean±SD, n=3, t test *: p<0.05; (28b) illustrates that RA induced expressions of PI3K and Akt isoforms over time by Western blots; (28c) illustrates that PI3K inhibitor 124005 inhibited the RA-induced Akt isoforms (24 hr) by flow cytometry. Data show mean±SD, n=3; (28d) illustrates Akt3 interacted with mTOR but inhibited by Akt3 siRNA by Western blots; (28e) illustrates RA induces temporal expression of mTOR by Western blots; (28f) illustrates Akt3 siRNA inhibited the RA-induced phosphorylation of mTOR; (28g) illustrates mTOR directly interacted with 4EBP1 (4 hr); (28h) illustrates hTS cells treated by RA (4 hr) with or without preincubation of mTOR siRNA or 4EBP1 siRNA were analyzed by Western blots for expressions of mTOR, 4EBP1, eIF4E, and eIF4B; (28i) illustrates eIF4E siRNA inhibited RA-induced interaction (4 hr) between RXRα and $G\alpha_{q/11}$ (upper) and between RARβ and Gβ (lower) by Western blots.

Figure 29:
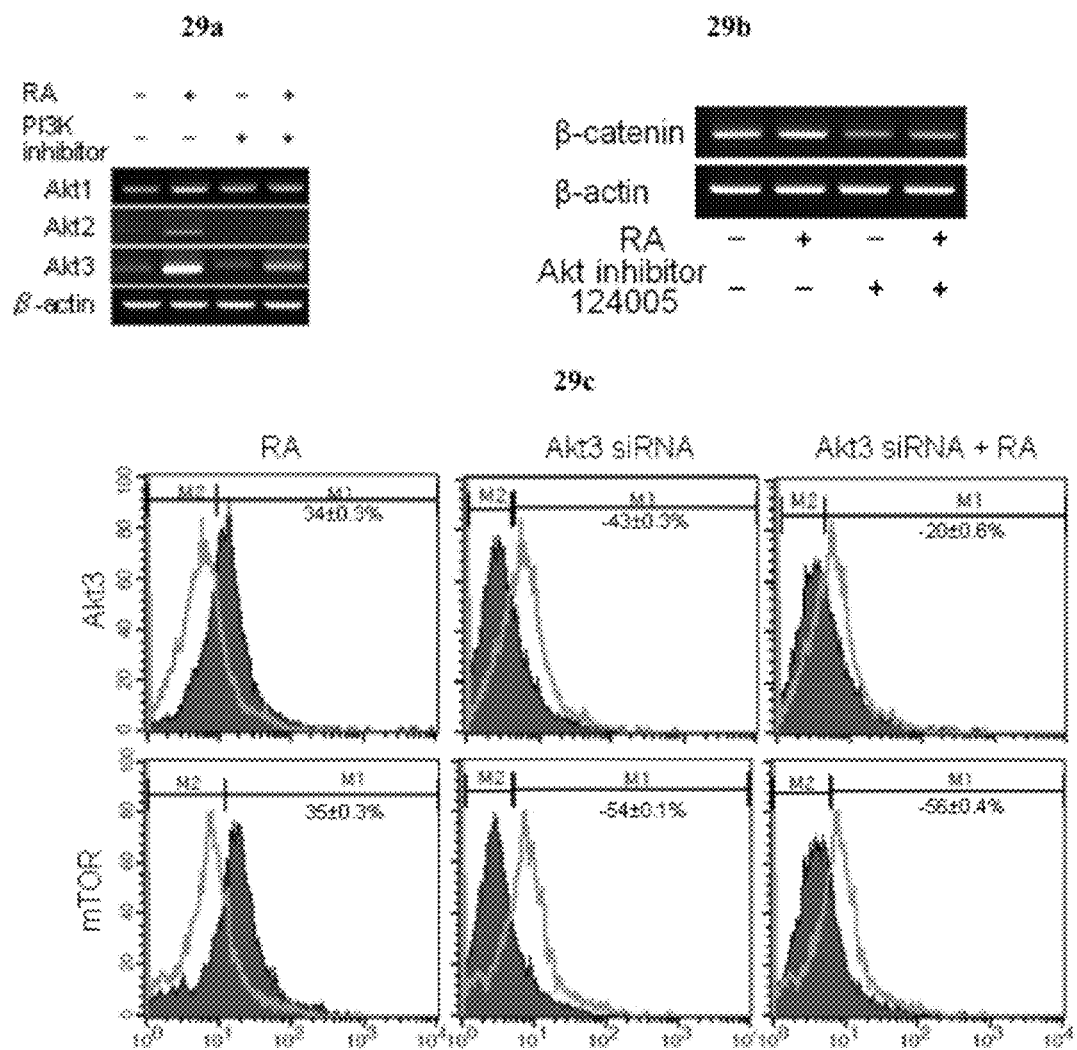

FIG. 29: (29a) illustrates that PI3K inhibitor suppressed the RA-induced expression of Akt isoforms, Akt1, 2, and 3 after overnight treatment in hTS cells by RT-PCR; (29b) Akt2 inhibitor inhibited expression of β-catenin mRNA by RT-PCR; (29c) Akt3 siRNA suppressed expression of mTOR by flow cytometry.

Figure 30:
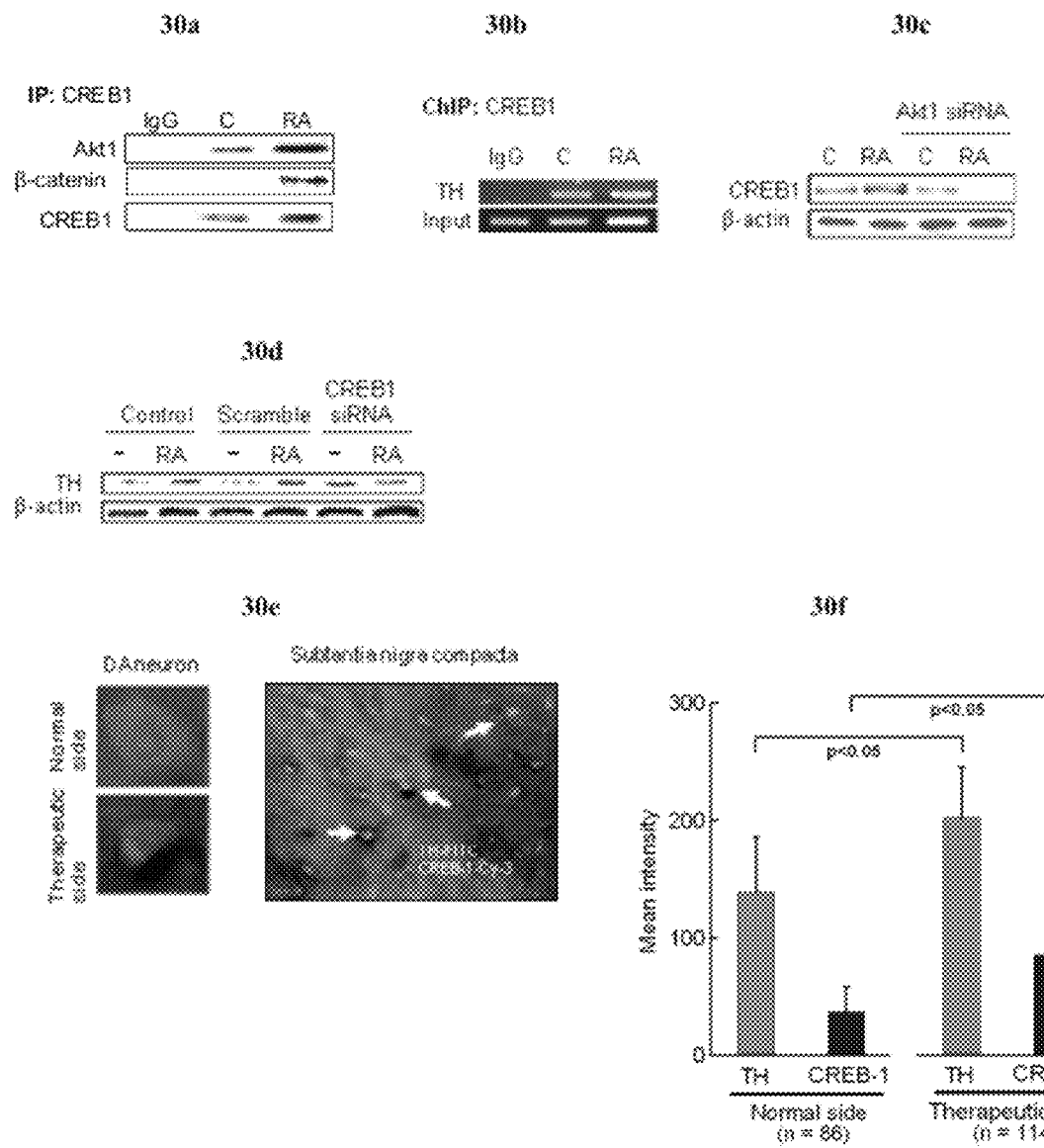

FIG. 30 illustrates CREB1 promotes transcription of TH: (30a) illustrates that CREB1 directly interacted with Akt1 and β-catenin by Western blots; (30b) illustrates that Akt1 siRNA inhibited expression of CREB1. β-actin: control; (30c) illustrates that CREB1 targeted at promoter of TH gene; (30d) illustrates that CREB1 siRNA inhibited expression of TH by Western blots; (30e) illustrates that immunofluorescence tissue analysis revealed co-expression of TH-FITC (blue color) and TH-Cy-3 (red color) in DA neurons (white arrow) in the therapeutic SNC side at 12 weeks postimplantation of tNSCs in PD rat brain (right panel). Amplified DA neuron in the normal side (left upper) and the therapeutic sides (left lower). Positive CREB1 stain was found in the nucleous; (30f) illustrates that histograms showing the relative mean intensities of TH and CREB1 expressed in DA neurons in the normal (left; n=86) and the therapeutic sides (right; n=114). Error bars: mean±SD; n: total cells counted; p<0.05: significant statistically.

Figure 31:
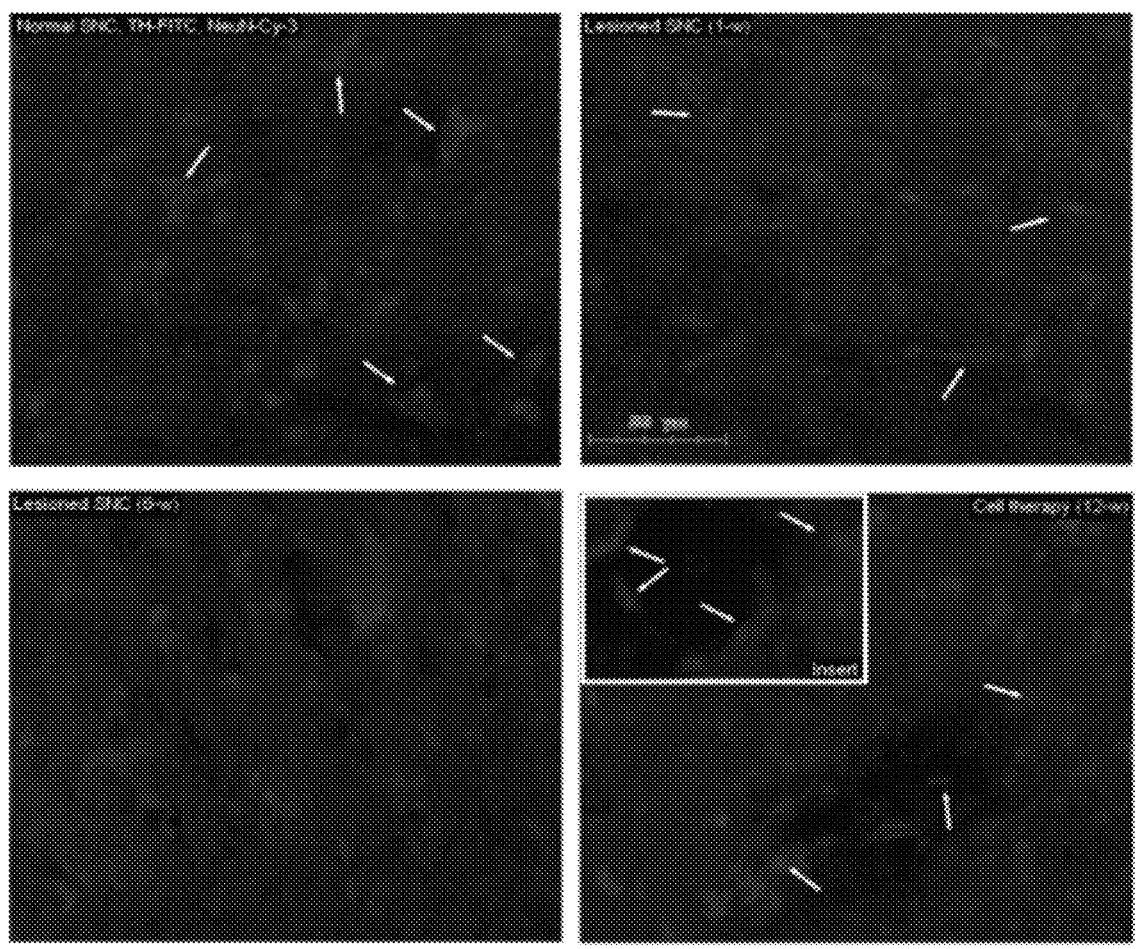

FIG. 31 illustrates immunohistofluoresence analysis: TH(+) and NeuN(+) motor neurons (arrow) in the SNC of control (left upper). Decreased TH(+) (arrow) at 1-week after 6-OHDA injury (right upper). Apparent reduction in TH(+) neurons with disarrangement of TH-positive neural terminals (green granules), and various degenerative cavity formation (red explosive circle) at 6-week post-injury (left lower). After transplantation, TH(+) neurons (arrow) at wall of the degenerative cavity (red explosive circle; insert) with TH(+) neural terminals (green color) projecting into the cavity (right lower).

Figure 32:
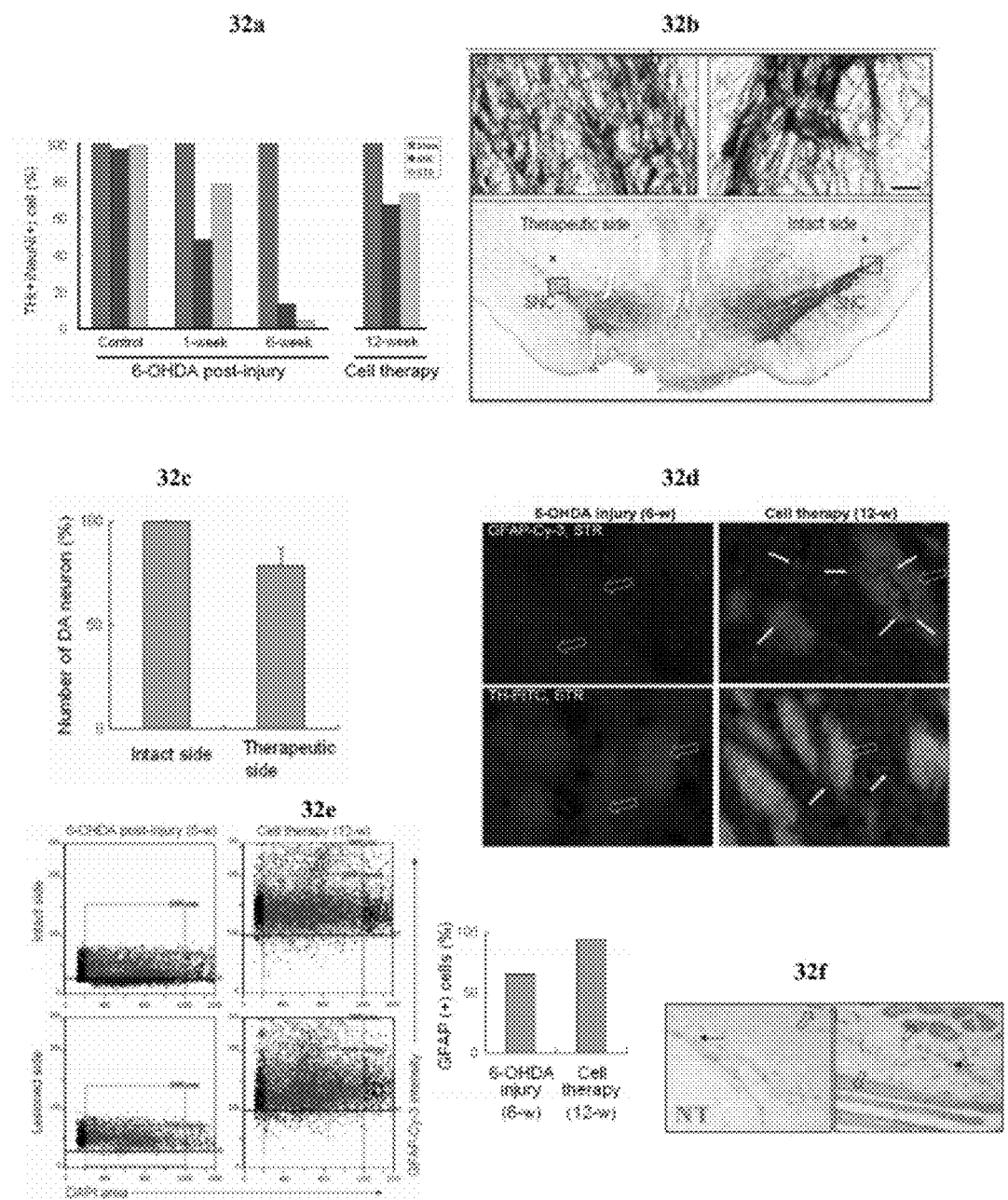

FIG. 32 illustrates in vivo regeneration of TH(+) and GFAP(+) cells with less immunoresponses: (32a) illustrates a number of TH(+) cells at 1- and 6-week reduced to 48% and 13% in the lesioned SNC (dark grey) and 78% and 4% in the lesioned striatum (light grey), respectively, post-injury. After transplantation, TH(+) cells re-grew up to 67% and 73% in the lesioned SNC and striatum, respectively (right panel). Data analyzed by the software Tissuequest 2.0 (TissueGnostics Gmbh, Vienna, Austria); (32b) illustrates regeneration of dopaminergic neurons in the lesioned SNC (lower panel) with amplification (left upper, insert a) compared with the intact side (right upper, insert b); (32c) illustrates transplantation of tNSCs at 12 weeks yielded 78.4±8.3% (mean±SEM; n=4) of recovery rate in TH-positive neurons (arrow) in the lesioned SNC compared to the intact side; (32d) illustrates degeneration of TH-FITC(+) and GFAP-Cy-3(+) Wilson's pencils (blank arrow) at 6-week post-injury in the lesioned striatum (left column). At 12 weeks postimplantation (right column), several GFAP(+) cells (arrow) appeared inside the fine fibers of re-established Wilson's pencils (blank arrow); (32e) illustrates immunohistofluorescence imaging analysis, cells were counted in the gate (left scatter plots) determined by the location of cell size (8-10 μm in diameter) and its corresponding intensity of GFAP-Cy-3. Gate (red scatter plot): glial cells counted; black scatter plots: exclusive cells with bizarre size; blue scatter plots: cells with abnormal GFAP intensity. In the striatum, the GFAP(+) cells were 65.5% in the lesioned side before treatment and became 93.9% after cell therapy compared to the intact side (right panel); (32f) illustrates hTS cells implantation into the SCID mice raised only minor immunoreactions and without tumorigenesis observed. Myxoid-like bizarre cells (black arrow), muscle fibers (blank arrow), and needle track (NT).

Figure 33:
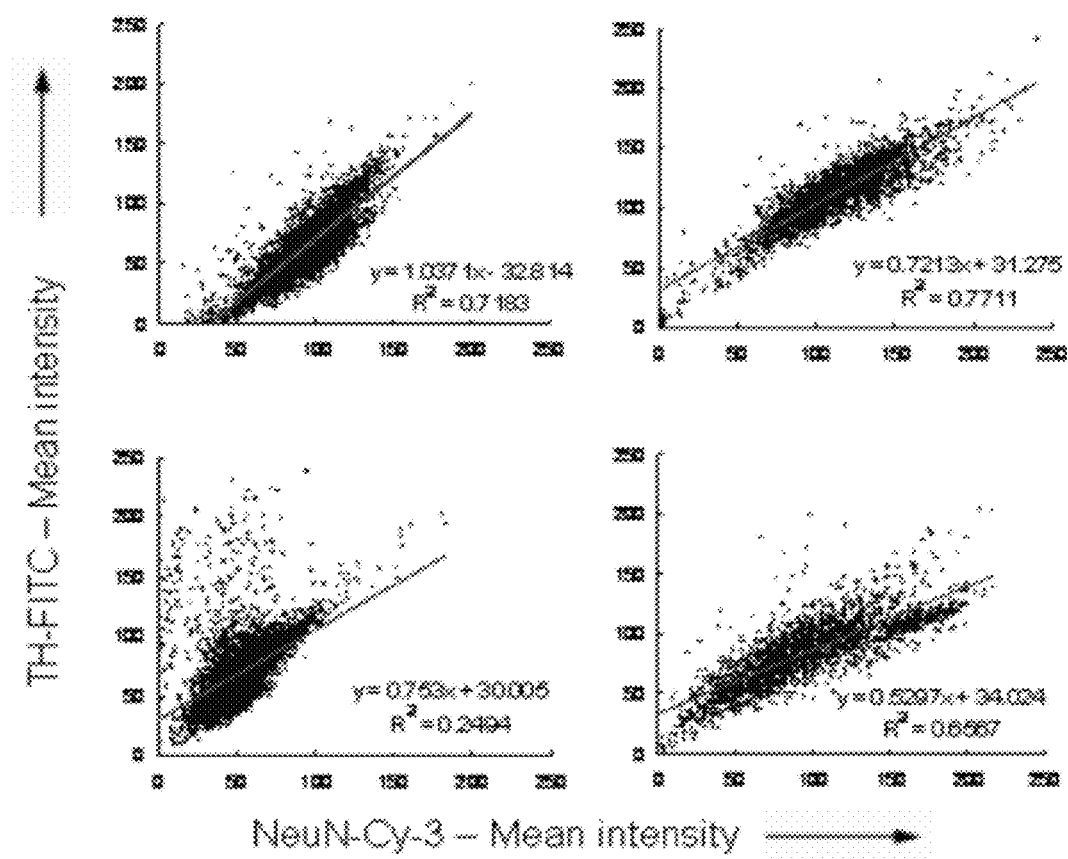

FIG. 33 illustrates the qualification of TH(+) cells in the SNC before and after cell therapy, using the coefficient of determination between TH-FITC and NeuN-Cy-3, measured by immunohistofluorescent scatter plots in the chronic PD rats. (33 left upper) illustrates normal SNC: $R^2$=0.72; (33 right upper) illustrates SNC by 6-OHDA damage (1-week): $R^2$=0.77; (33 left lower) illustrates SNC by 6-OHDA damage (6-week): $R^2$=0.25; (33 right lower) SNC after tNSCs transplantation (12-week): $R^2$=0.66. Results shown represent the average of 2 rats.

DETAILED DESCRIPTION OF THE INVENTION

Neural tissue-derived stem cells, phenotype-specified progenitor cells derived from pluripotential embryonic stem cells (ESC), and neural cells derived from various transdifferentiated non-neural stem cells have all been investigated in preclinical studies for their ability to generate neurons and glia, and the use of neural stem cells in clinical trials has been described. Though embryonic stem (ES) cells have shown potential as cell therapeutics, Bjorklund, L. M., et al. Proc. Nat. Acad. Sci. 2002, 99, 2344-49, access to such therapies is limited and associated with ethical concerns.

Stem cells possess the capacity for self-renewal and to produce committed progenitors including neural stem cells. Reubinoff B. E. et al., Nat. Biotech. 2001, 19, 1134-1140.

Provided herein are isolated neural stem cells that are derived from trophoblast tissue. Further provided herein are isolated neural stem cells (tNSCs) that are robust and survive several passages in cell culture and also possess characteristics of pluripotency and immune privilege. In one embodiment described herein, a method is described for induction of dopaminergic neurons from tNSCs derived from human trophoblast stem (hTS) cells. Further provided herein are methods that allow for survival and growth of the grafted tNSCs into dopaminergic neurons, and methods for assessment of recovery of impaired behaviors to achieve results with reduced variability compared to current therapeutic regimens.

Also provided herein are isolated neural stem cells derived from hTS cells that are cultured without using mouse embryonic feeder cells, circumventing problematic contaminations. Provided herein are methods for generation of hTS cell-derived tNSCs efficiently and reproducibly, leading to a uniformly mixed subset of populations that is distinguishable from the other methods used to induce dopaminergic neurons from cells of other origins. Provided herein are methods for transplantation of the dopaminergic tNSCs into the brain as a cell suspension thereby circumventing uneven growth that is associated with tissue grafts.

Provided herein are methods of modulating a stem cell with an induction drug to differentiate into a cell with neuronal characteristics. In one embodiment the induction drug modulates the expression or activity of modulating one or more proteins in the stem cell. In one embodiment one of the one or more proteins is Wnt2B, Fzd6, Dvl3, FRAT1, GSK3β, HDAC6, β-catenin, Gα$_{q/11}$, GP, RXRα, RARβ, GLuR1, PI3K, AKt1, AKt2, AKt3, mTOR, EIF4EBP, CREB1, TH (tyrosine hydroxylase), PLC-β, PIP2, CaMKII, EIF4B, parkin, SNCA, tublin, calcineurin, CRMP-2, NFAT1, importin, LEF1, Pitx2, MEF2A, or EP300. In one embodiment the stem cell can be a trophoblast, embryonic or induced progenitor stem cell. In one embodiment the cell with neuronal characteristics is a NSC, dopamine producing cell, dopaminergic neuron, unipolar neuron, bipolar neuron, multipolar neuron, pyramidal cell, Purkinje cell, and anterior horn cell, basket cell, betz cell, Renshaw cell, granule cell, or medium spiny cell.

Also provided herein are methods of modulating a stem cell with an induction drug to differentiate into a cell with reduced immunogenicity. In one embodiment the induction drug modulates the expression or activity of modulating one or more proteins in the stem cell. In one embodiment one of the one or more proteins is Wnt2B, Fzd6, Dvl3, FRAT1, GSK3β, HDAC6, β-catenin, Gα$_{q/11}$, Gβ, RXRα, RARβ, GLuR1, PI3K, AKt1, AKt2, AKt3, mTOR, EIF4EBP, CREB1, TH (tyrosine hydroxylase), PLC-β, PIP2, CaMKII, EIF4B, parkin, SNCA, tublin, calcineurin, CRMP-2, NFAT1, importin, LEF1, Pitx2, MEF2A, or EP300. In one embodiment the stem cell can be a trophoblast, embryonic or induced progenitor stem cell. In one embodiment the cell with reduced immunogenicity does not induce an immune response or can inhibit an immune response by a T cell, B cell, macrophage, microglia cell, mast cell, or natural killer (NK) cell.

Human Trophoblast Stem Cells (hTS Cells)

Human fallopian tubes are the site of fertilization and the common site of ectopic pregnancies in women, where several biological events take place such as the distinction between inner cell mass (ICM) and trophectoderm and the switch from totipotency to pluripotency with the major epigenetic changes. These observations provide support for fallopian tubes as a niche reservoir for harvesting blastocyst-associated stem cells at the preimplantation stage. Ectopic pregnancy accounts for 1 to 2% of all pregnancies in industrialized countries and are much higher in developing countries. Given the shortage in availability of human embryonic stem cell (hES cells) and fetal brain tissue, described herein is the use of human trophoblast cells (hTS cells) derived from ectopic pregnancy as a substitution for scarcely available hES cells for generation of progenitor cells.

In one embodiment, the human trophoblast cells derived from ectopic pregnancies do not involve the destruction of a human embryo. In another embodiment, the human trophoblast cells derived from ectopic pregnancies do not involve the destruction of a viable human embryo. In another embodiment, the human trophoblast cells are derived from trophoblast tissue associated with non-viable ectopic pregnancies. In another embodiment, the ectopic pregnancy cannot be saved. In another embodiment, the ectopic pregnancy would not lead to a viable human embryo. In another embodiment, the ectopic pregnancy threatens the life of the mother. In another embodiment, the ectopic pregnancy is tubal, abdominal, ovarian or cervical.

During blastocyst development, ICM contact per se or its derived diffusible 'inducer' triggers a high rate of cell proliferation in the polar trophectoderm, leading to cell movement toward the mural region throughout the blastocyst stage and can continue even after the distinction of the trophectoderm from the ICM. The mural trophectoderm cells overlaying the ICM are able to retain a 'cell memory' of ICM. Normally, at the beginning of implantation the mural cells opposite the ICM cease division because of the mechanical constraints from the uterine endometrium. However, no such constraints exist in the fallopian tubes, resulting in the continuing division of polar trophectoderm cells to form extraembryonic ectoderm (ExE) in the stagnated blastocyst of an ectopic pregnancy. In one embodiment, the ExE-derived TS cells exist for at least a 4-day window in a proliferation state, depending on the interplay of ICM-secreted fibroblast growth factor 4 (FGF4) and its receptor fibroblast growth factor receptor 2 (Fgfr2). In another embodiment, the ExE-derived TS cells exist for at least a 1-day, at least a 2-day, at least a 3-day, at least a 4-day, at least a 5-day, at least a 6-day, at least a 7-day, at least a 8-day, at least a 9-day, at least a 10-day, at least a 11-day, at least a 12-day, at least a 13-day, at least a 14-day, at least a 15-day, at least a 16-day, at least a 17-day, at least a 18-day, at least a 19-day, at least a 20-day window in a proliferation state. Until clinical intervention occurs, these cellular processes can yield an indefinite number of hTS cells in the preimplantation embryos; such cells retaining cell memory from ICM, reflected by the expression of ICM-related genes.

Figure 7:
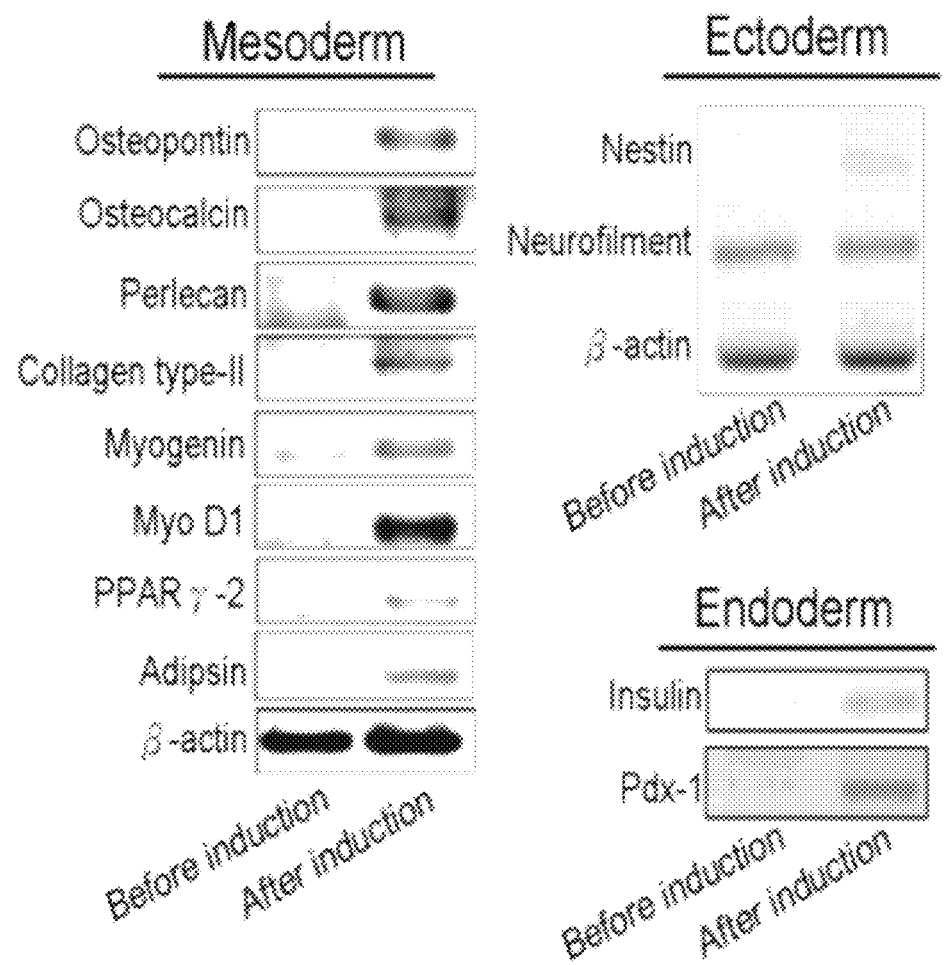
FIG. 7 illustrates that hTS cells express components of all three primary germ layers, including the ectoderm, the mesoderm and the endoderm after appropriate inductions; left column of each panel correlates to gene expression before induction; right column of each panel correlates to gene expression after induction.
Figure 8:
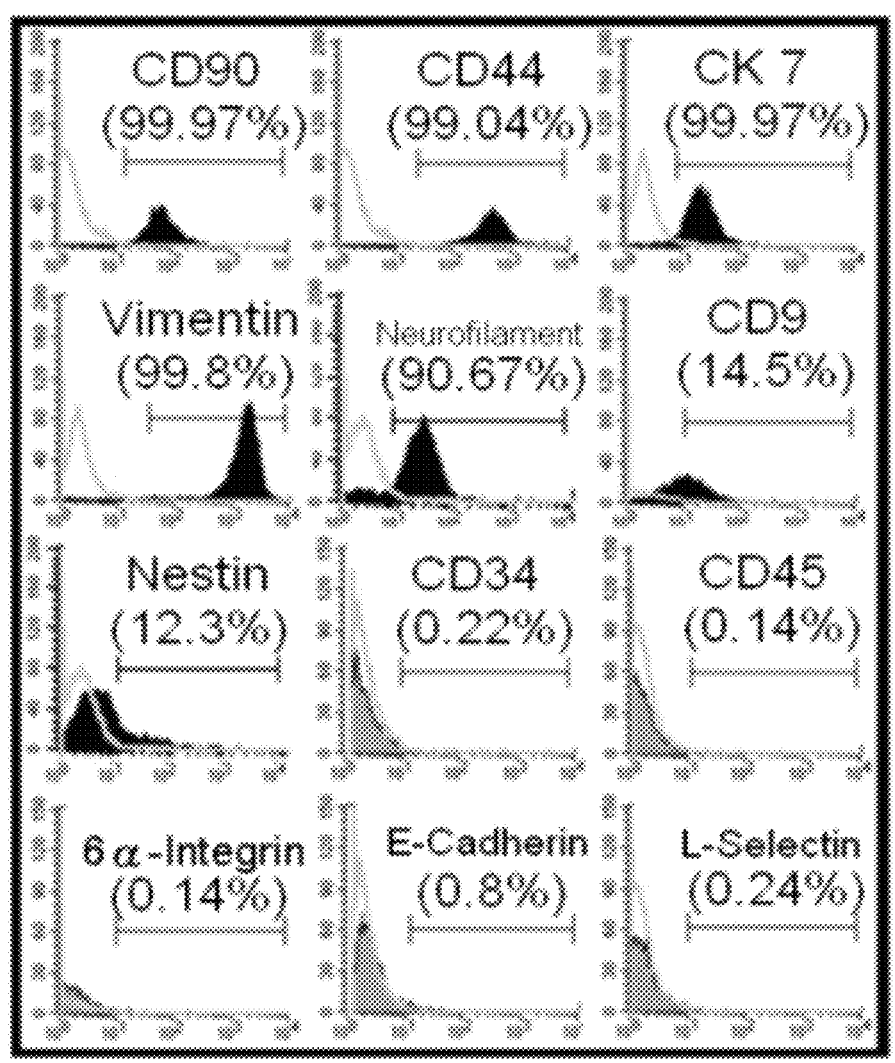
FIG. 8 illustrates flow cytometric analysis results, indicating that hTS cells express mesenchymal stem cell markers (CD90, CD44, CK7, Vimentin and Neurofilament) and are negative for hematopoietic stem cell markers (CD34, CD45, α6-integrin, E-cadherin, and L-selectin).
Figure 9:
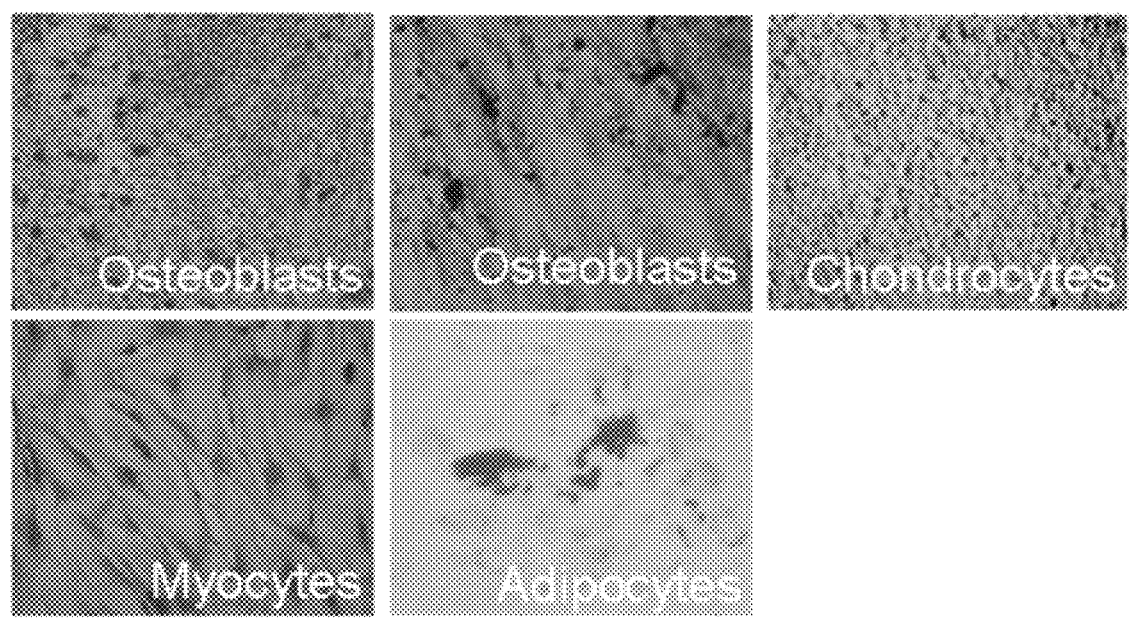
FIG. 9 shows that upon appropriate induction, hTS cells could be differentiated into a variety of specific cell phenotypes.
Figure 11:
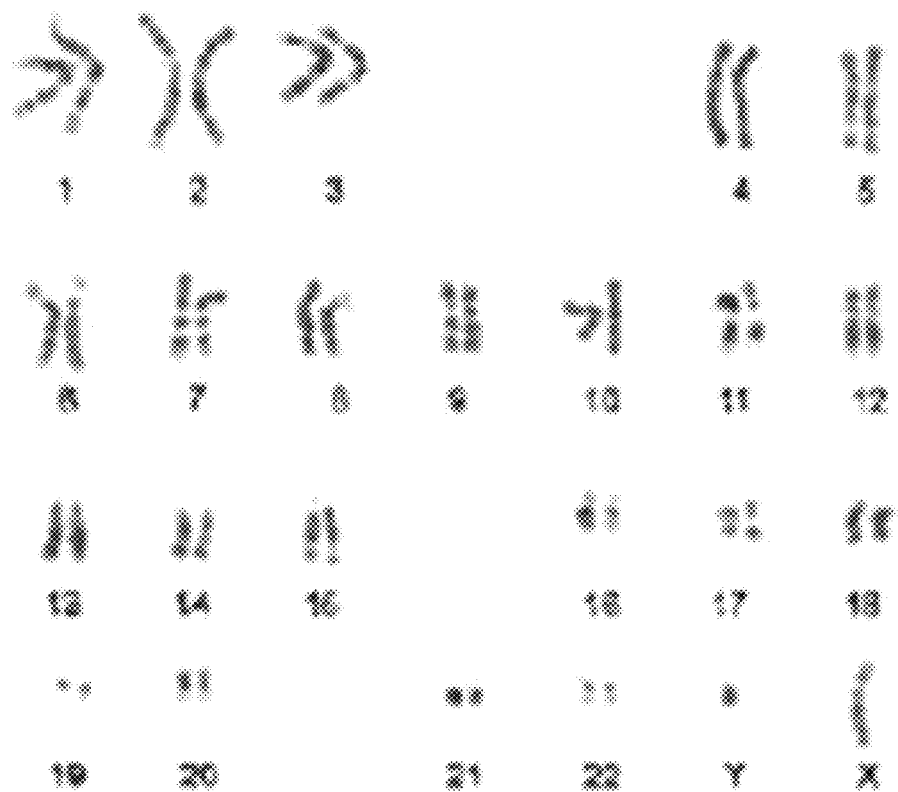
FIG. 11. Chromosome analysis showed that hTS cells did not change the patterns of karyotypes (46, XY). To check the cell lifespan in generations, no significant shortening in telomere length was observed between 3rd and 7th passage in culture (FIG. 1c) by Southern blot analysis.

One aspect described herein are hTS cells and chorionic cytotrophoblasts before uterine implantation. In one embodiment, hTS cells possess both specific genes of inner cell mass (ICM) (Oct4, Nanog, Sox2, FGF4) and trophectoderm (Cdx2, Fgfr-2, Eomes, BMP4) (FIG. 1a) and express components of all three primary germ layers (FIG. 7). In another embodiment, the hTS cells express hES cell-related surface markers such as specific stage embryonic antigen (SSEA)-1, -3 and -4 (FIG. 1b) and mesenchymal stem cell-related markers (CD 44, CD90, CK7 and Vimentin), while hematopoietic stem cell markers (CD34, CD45, α6-integrin, E-cadherin, and L-selectin) were not expressed (FIG. 8). In one embodiment, hTS cells could be differentiated into a variety of specific cell phenotypes of three primary germ layers upon induction (FIG. 9). Transplantation of hTS cells into the male severe combined immune deficiency (SCID) mice subcutaneously caused only minor chimeric reaction at 6-8 weeks postimplantation histologically (FIG. 10). In one embodiment, chromosome analysis showed that hTS cells did not change the patterns of karyotypes (46, XY) (FIG. 11). In another embodiment, the cell lifespan was not significantly shortened in telomere length between 3rd and 7th passage in culture (FIG. 1c).

One aspect provided herein describes the distinction between hTS cells and placenta derived mesenchymal stem (PDMS) cells, using the Affymetrix™ platform to interrogate the GeneChip Human Genome U133 plus 2.0 GeneChip for a global gene comparison between hTS cells and PDMS cells. In one embodiment, the hTS cells exhibited about 10%, about 15%, about 20%, about 25%, about 30%, about 35%, about 40%, about 45%, about 50%, about 55%, about 60%, about 65% about 70%, or about 75% less gene expression than that in PDMS cells. In another embodiment, the hTS cells exhibited total 2,140 genes (fold change >2-fold) which is about 40% less than that in PDMS cells (3,730 genes) (FIG. 1d). In one embodiment, the gene intensity distribution of hTS cells displayed a homogenous pattern distinct from that in PDMS cells. In another embodiment, the hTS cells represent a distinct group of cytotrophoblasts at a stage of pre-implantation, whereby they possess molecular portraits of inner cell mass (ICM) and/or trophectoderm. In another embodiment, the hTS cells exhibit characteristics of pluripotency and self-renewal similar to that of hES cells.

Withdrawal of LIF Mediates Overexpression of Nanog in hTS Cells

Cytotrophoblasts are the precursors of syncytiotrophoblasts in humans (Benirschke, K., Kaufmann, P. in Pathology of the human placenta, 39-51 Spring-Verlag New York Inc., 1990). A zone of trophoblast specification is established when the embryo is a morula, reflecting a distinct combination of transcription factors in that zone of cells and the influence of various environmental cues and growth factors on them.

Much evidence indicates that naive pluripotency of early epiblast and authentic ES cells are dependent on the action of three transcriptional organizers, Oct4, sex determining region Y-box 2 (Sox2), and Nanog (Chambers I., et al., *Oncogene*, 23:7150-7160 (2004); Niwa H. *Development*, 134:635-646 (2007)). ES cells maintain pluripotency through a complex interplay of different signaling pathways and transcription factors, including leukemia inhibitory factor (LIF), Nanog, Sox2, and octamer-binding transcription factor 3 and 4 (Oct3/4). The transcription factor Nanog plays a key role in maintaining the pluripotency of mouse and human ES cells, while LIF works in concert with Oct4 and Nanog to support pluripotency and self-renewal (Cavaleri, F. et al. *Cell* 113, 551-552 (2003)).

LIF, an interleukin-6 class cytokine, affects cell growth and differentiation. LIF binds to leukemia inhibitory factor receptor alpha (LIFR-alpha), which forms a heterodimeric receptor complex with membrane glycoprotein 130 (GP130) common receptor. The binding of LIF leads to the activation of janus kinase (JAK)/signal transducer and activator of transcription (STAT) signaling pathways as well as mitogen-activated protein kinase (MAPK) pathways. LIF is normally expressed in the trophectoderm of developing embryo. LIF is thought to play a role in maintaining undifferentiated state. Removal of LIF from a stem cell culture usually leads to differentiation of the cultured stem cell. LIF also affects the expression of Nanog, a gene known to play a crucial role in stem cell maintenance.

Normally, a pleiotropic cytokine leukemia inhibitory factor (LIF) is expressed at a higher concentration in the fallopian tubes than in the endometrium, showing a gradient reduction from the ampulla to the isthmic segment (FIG. 1g). While in ectopic pregnancy, LIF levels can increase 2 to 4-fold in the fallopian tube (Wånggren, K., et al., *Mol. Hum. Reprod.* 2007, 13, 391-397). Functionally, LIF can integrate other signals to activate pluripotent transcription factors, for example, Oct4 and Nanog, to maintain pluripotency and self-renewal in mouse embryonic stem (mES) cells. On withdrawal of LIF, cell proliferation continues but a caudal-related homeobox transcription factor Cdx2 is activated, triggering for trophectoderm differentiation in embryonic stem (ES) cells.

In one embodiment, a method is described to determine how hTS cells maintain characteristics of pluripotency and self-renewal. In one embodiment, the association of LIF with pluripotent transcription factors (e.g., factors described in Smith, A. G., et al., *Nature* 336, 688-690 (1998), Williams, R. L., et al., *Nature* 336, 684-687, (1998), Cavaleri, F. et al., *Cell* 113, 551-552 (2003); Chambers I., et al., *Cell*, 2003; 113:643-655, Boiani, L. A. et al., *Nature Rev. Mol. Cell Biol.* 6, 872-884 (2005)) was examined in hTS cells.

hTS cells were obtained from women who had suffered tubal ectopic pregnancies at 5-8 weeks of gestation and characterized as a distinct population of cytotrophoblasts, possessing specific genetic markers (e.g., markers described in Adjaye, J., et al., *Stem Cells*, 2005, 23, 1514-1525) of ICM-derived human embryonic stem (hES) cells and trophectoderm (FIG. 1a).

Provided herein, in one embodiment, is a method to affect hTS cell differentiation by modulating the exposure of said cell to LIF. For example, hTS cells are divided into three groups and exposed to different concentrations of LIF. In one embodiment, the concentration of LIF is about 1000, about 750, about 600, about 550, about 525, about 500, about 450, about 400, about 350, about 300, about 250, about 200, about 150, about 125, about 100, about 75, about 50, or about 25 Units/mL. In another embodiment, the concentrations of LIF are 500, 250, and 125 Units/mL. In one embodiment, the concentration of LIF is 500 Units/mL. In another embodiment, the concentration of LIF is 250 Units/mL. In another embodiment, the concentration of LIF is 125 Units/mL.

In one embodiment, the hTS cells are exposed to different concentrations of LIF for 1, 2, 3, 4, 5, 6, 7, 8, 9, 10, 11, 12, 13, 14, 15, 16, 17, 18, 19, 20, 21, 22, 23, 24, 25, 26, 27, 28, 29, or days. In another embodiment, the hTS cells are exposed to different concentrations of LIF for 3, 6, 12, 18, 24, 30, 36, 48, 60, 72, 84, 96, 108, 120, 132, 144, 156, 168, 180, 192, 204, 216, 228, 240, or 252 hours. In another embodiment, the hTS cells are exposed to different concentrations of LIF for about 1 to 30, about 1 to 28, about 1 to 26, about 1 to 24, about 1 to 22, about 1 to 20, about 1 to 18, about 1 to 15, about 1 to 13, about 1 to 10, about 1 to 9, about 1 to 8, about 1 to 7, about 1 to 6, about 1 to 5, about 1 to 4, or about 1 to 2 days. In another embodiment, the hTS cells are exposed to different concentrations of LIF for 3 days.

One aspect described herein is that lower concentrations of LIF changing the expression of certain genes, which include but are not limited to Oct4, Sox2, Cdx2, and Nanog. Another embodiment demonstrates that withdrawal of LIF and/or lower concentrations of LIF suppresses Oct4 and Sox2 expressions, and in contrast, promotes Cdx2 and Nanog by RT-PCR (FIG. 1e). In one embodiment, these phenomena were further confirmed by flow cytometric analysis, showing suppression of Oct4 and Sox2, in a dose-dependent manner (FIG. 1f).

In another embodiment, the relative expression of Oct4/Cdx2 ratio indicates cell fate in early embryonic differentiation. In another embodiment, the withdrawal and/or decrease of LIF exposure leads to a decrease in Oct4 expression. In another embodiment, the withdrawal and/or decrease of LIF exposure promotes the expressions of transcription factors Cdx2, Nanog, and Sox2 in a dose-dependent manner, which is consistent with quantitative PCR (qPCR) analyses.

Another aspect is described herein is a high Oct4/Cdx2 ratio at the ampulla with a gradient reduction toward the isthmic segment in hTS cells (FIG. 1g) compatible with the trend of LIF levels in the fallopian tubes, thereby implying a cell fate choice toward hES cells. In one embodiment, upregulation of relative Nanog/Cdx2 ratio (2-fold) further enforces pluripotency in the cell. In one embodiment, upregulation of relative Nanog/Cdx2 ratio (2-fold) maintains pluripotency in the hTS cell. In another embodiment, the Sox2/Cdx2 expression ratio does not change for the hTS cells to maintain pluripotency. In another embodiment, Cdx2 overexpression is favorable for the hTS cells to maintain a trophoblastic phenotype.

One embodiment described herein is a method to examine the relationship between Nanog and Cdx2 in hTS cells. In another embodiment, knockout studies of both Nanog and Cdx2 by using siRNA promotes Cdx2 and Nanog expressions, respectively (FIG. 1h), supporting the reciprocal relationship between Nanog and Cdx2 in hTS cells similar to that of Oct4 and Cdx2 in ES cells for cell fate choice (Niwa, H., et al., *Cell* 123, 917-929). In another embodiment, overexpression of Nanog in combination with elevated Nanog/Cdx2 ratio compensates for the decreased Oct4/Cdx2 ratio and is sufficient for the maintenance of pluripotency and/or renewal which determines cell differentiation fate in hTS cells.

One aspect described herein shows that overexpression of Nanog upon withdrawal of LIF is at least one factor that plays a role in maintaining the pluripotency of hTS cells.

Retinoic Acid (RA) and Related Pathways

Retinoic acid (RA), a derivative of vitamin A, plays a role in ES cell differentiation and embryogenesis. In ES cells, RA acts by binding to its nuclear receptors and inducing transcription of specific target genes to generate a number of different cell types. In one embodiment, induction with RA enables an hTS cell-derived tNSCs to sustain a stably undifferentiated state with specific patterning.

In one embodiment, treating hTS cells with all trans-retinoic acid (RA) produces neural stem cells suitable for implantation into a rat disease model (e.g., Parkinson's disease model). In another embodiment, withdrawal and/or a decrease of LIF exposure in hTS cells mediates overexpression of Nanog, which is responsible for the pluripotency and maintenance of self-renewal of hTS cells. Also described herein are certain molecular pathways that allow RA induced hTS cells to differentiate into neural stem cells including pathways that play a role in reversible epithelial-mesenchymal transition (EMT), bone morphogenetic protein (BMP) and Wnt signaling pathway cross-talk, and triggering the target gene Pitx2 for neural stem cells formation. Accordingly, one embodiment describes the use of modulators of RA-related pathways for generation of neural stem cells from hTS cells.

RA Induces a Uniform Complex of NSC Subtypes

In one embodiment, hTS cells are induced to produce neural stem cells. In one embodiment, the hTS cells are exposed to or treated with an inducing agent. In one embodiment, an inducing agent includes but is not limited to retinoic acid, nerve growth factor, basic fibroblast growth factor, neurotropins (e.g., neurotropin 3) and/or combinations thereof. Additional exemplary inducing agents include, but are not limited to: erythropoietin (EPO), brain derived neurotrophic factor (BDNF), wingless-type MMTV integration site (Wnt) proteins (e.g., Wnt3a), transforming growth factor alpha (TGFα), transforming growth factor beta (TGFβ), bone morphogenetic proteins (BMPs), thyroid hormone (TH, including both the T3 and T4 forms), thyroid stimulating hormone (TSH), thyroid releasing hormone (TRH), hedgehog proteins (e.g., sonic hedgehog), platelet derived growth factor (PDGF), cyclic AMP, pituitary adenylate cyclase activating polypeptide (PACAP), follicle-stimulating hormone (FSH), growth hormone (GH), insulin-like growth factors (IGFs, e.g., IGF-1), growth hormone releasing hormone (GHRH), prolactin (PRL), prolactin releasing peptide (PRP), fibroblast growth factor (FGF), estrogen, serotonin, epidermal growth factor (EGF), gonadotropin releasing hormone (GnRH), ciliary neurotrophic factor (CNTF), leukemia inhibitory factor (LIF), granulocyte colony stimulating factor (G-CSF), granulocyte-macrophage colony stimulating factor (GM-CSF), vascular endothelial growth factor (VEGF), luteinizing hormone (LH), human chorionic gonadotropin (hCG), pheromones (e.g., 2-sec-butyl-4,5-dihydrothiazole, 2,3-dehydro-exo-brevicomin, alpha and beta farnesenes, 6-hydroxy-6-methyl-3-heptanone, 2-heptanone, trans-5-hepten-2-one, trans-4-hepten-2-one, n-pentyl acetate, cis-2-penten-1-yl-acetate, 2,5-dimethylpyrazine, dodecyl propionate, and (Z)-7-dodecen-1-yl acetate), and/or combinations thereof. In another embodiment, the inducing agent is an analog or variant that has the activity of the native inducing agent.

By way of non-limiting example, retinoic acid is used to chemically induce hTS cells. The pleiotropic factor all-trans retinoic acid (RA) plays in vivo functions in neural differentiation, patterning and motor axon outgrowth via multiple pathways, including but not limited to RA/RARs/RXRs signaling, Wnt signaling and ERK pathway in ES cells (Maden, M. *Nat. Rev. Neuroscience* 8, 755-765 (2007), Lu J, et al., *BMC Cell Biol.* 2009, 10: 57, Wichterle H, et al., *Cell.* 2002; 110:385-397). RA induces the expression of tyrosine hydroxylase (TH), the hallmark enzyme of dopaminergic neurons, and the neurite formation in mES cells (Wichterle H, et al., *Cell.* 2002; 110:385-397), hES cells (Li, L. et al. *Stem Cells* 22, 448-456 (2004)) and adult neurogenesis (Jacobs S, et al., *Proc Natl Acad Sci* 2006, 103(10): 3902-7).

In one embodiment, a method is described to determine the fate of hTS cells treated with RA. In another embodiment, the hTS cells are treated with 1, 2, 3, 4, 5, 6, 7, 8, 9, 10, 11, 12, 13, 14, 15, 16, 17, 18, 20, 25, 30, 35, 40, 45, 50, 55, 60, or 65 µM of RA. In another embodiment, the hTS cells are treated with about 0.5-75, about 1-65, about 1-60, about 1-50, about 1-55, about 1-50, about 1-40, about 1-35, about 1-30, about 1-25, about 1-20, about 1-15, about 1-13, about 1-10, about 2-10, about 5-10, or about 8-10 µM of RA. In another embodiment, the hTS cells are treated with 10 µM of RA.

In one embodiment, the hTS cells are exposed to RA for 1, 2, 3, 4, 5, 6, 7, 8, 9, 10, 11, 12, 13, 14, 15, 16, 17, 18, 19, 20, 25, 30, 35, or 40 days. In another embodiment, the hTS cells are exposed to RA for 3, 6, 12, 18, 24, 30, 36, 48, 60, 72, 84, 96, 108, 120, 132, 144, 156, 168, 180, 192, 204, 216, 228, 240, or 252 hours. In another embodiment, the hTS cells are exposed to RA for about 1 to 20, about 1 to 18, about 1 to 15, about 1 to 13, about 1 to 10, about 1 to 9, about 1 to 8, about 1 to 7, about 1 to 6, about 1 to 5, about 1 to 4, or about 1 to 2 days. In another embodiment, the hTS cells are exposed to RA for different durations: 1, 2, 3, 4, 5, 6, 7, or 8 days each. In another embodiment, the hTS cells are exposed to RA for 1 day. In another embodiment, the hTS cells are exposed to RA for 2 days. In another embodiment, the hTS cells are exposed to RA for 3 days. In another embodiment, the hTS cells are exposed to RA for 4 day. In another embodiment, the hTS cells are exposed to RA for 5 days. In another embodiment, the hTS cells are exposed to RA for 6 day. In another embodiment, the hTS cells are exposed to RA for 7 days. In another embodiment, the hTS cells are exposed to RA for 8 day.

In one embodiment, RA induces hTS cells differentiation into a variety of phenotypical neural cells, which include but are not limited to glial restricted precursors (GRP), neuronal restricted precursors (NRP), multipotent neural stem (MNS)

cells, astrocytes (AST) and undefined trophoblast giant cells (TGC), expressing neural stem cell marker nestin immunocytochemically (FIG. 2a). In another embodiment, a similar ratio in distribution of mixed RA-induced neural progenitors results over 1 to 5-day RA-induction periods. In another embodiment, the cell differentiation becomes undefined trophoblast giant cells over a 7-day RA treatment.

Accordingly, provided herein, in one embodiment, are RA-induced neural stem cells derived from hTS cells. In another embodiment, the RA induction period is 1, 2, 3, 4, 5, 6, 7, 8, 9, 10, 11, 12, 13, 14, 15, 16, 17, 18, 19, 20, 25, 30, 35, or 40 days. In another embodiment, the RA induction period is 3, 6, 12, 18, 24, 30, 36, 48, 60, 72, 84, 96, 108, 120, 132, 144, 156, 168, 180, 192, 204, 216, 228, 240, or 252 hours. In another embodiment, the RA induction period is about 1 to 20, about 1 to 18, about 1 to 15, about 1 to 13, about 1 to 10, about 1 to 9, about 1 to 8, about 1 to 7, about 1 to 6, about 1 to 5, about 1 to 4, or about 1 to 2 days. In one embodiment, the RA induction period is from about one day to about 7 days. In another embodiment, the RA induction period is one day. In another embodiment, the RA induction period is 2 days. In another embodiment, the RA induction period is 3 days. In another embodiment, the RA induction period is 4 days. In one embodiment, the RA induction period is 5 days. In another embodiment, the RA induction period is 6 days. In another embodiment, the RA induction period is 7 days. In another embodiment, the RA induction period is 24 hours. In one embodiment, the RA induction period is 12 hours. In another embodiment, the RA induction period is 1 hour to 24 hours.

Described herein, in one embodiment, is a tNSC that expresses at least one neural stem cell gene and marker. In another embodiment, the tNSC expresses at least two, at least three, at least four or at least five neural stem cell genes. In another embodiment, the tNSC expresses at least two, at least three, at least four or at least five neural stem cell markers. Non-limiting examples of neural stem cell genes and markers include nestin, neurofilament, Ngn-3, MAP-2, Neo-D, CD133 and Oct4 (FIG. 2b). In one embodiment, the tNSCs also express RA receptor genes, which include but are not limited to RARβ, RXRα, and RXRβ, cellular retinoic acid binding protein (CRABP)-2, cellular retinol binding protein (CRBP)-1 and specifically, RA-synthesizing enzymes RALDH-2 and -3 which were found to be absent in ES cells.

Accordingly, one embodiment describes the use of expressed neural stem cell genes and markers, including nestin, neurofilament, Ngn-3, MAP-2, Neo-D, CD133 and Oct4, RA receptor genes such as RARβ, RXRα and RXRβ, CRABP-2, CRBP-1, RA-synthesizing enzymes RALDH-2 and -3 or the like, and/or modulators thereof, to facilitate the differentiation capacity of tNSCs. In one embodiment, both 3- and 5-day RA-induced hTS cells sustain neural stem cells markers in a similar ratio, including nestin, GFAP and neurofilament protein (FIG. 2c). In another embodiment, these tNSCs expressed tyrosine hydroxylase (TH) and 5-hydroxytryptamine (5-HT) immunocytochemically (FIG. 2d), implying their capacity to be differentiated into dopaminergic as well as serotonergic neurons. Another embodiment described herein is the differentiation of tNSCs to dopaminergic neurons and serotonergic neurons.

Further provided herein are tNSCs that consist of uniformly mixed neuroepithelial progenitor cells sustainable in a steady-state, genetically and phenotypically, in cell culture. This consistency in product is a desirable characteristic for any treatment regimen comprising stem cell-based therapy.

Association Between LIF and RA in Respect of Nanog Expression

In early embryonic development, tNSCs typically express RALDH-2. One embodiment described herein is a method to evaluate how LIF affects the RA-induced neurogenesis in hTS cells. The ability of LIF to inhibit RA-induced neuronal differentiation in mouse ES (mES) cells, renders transplantation more difficult (Martín-Ibáñez R, et al., *J. Neuron. Res.* 85, 2686-2710 (2007), Bain G, et al., *Dev Biol* 168: 342-357). Other reports claim a positive role of LIF in the differentiation of ES cells into neurons (Tropepe V, *Neuron* 2001, 30: 65-78).

In one embodiment, a method is described to evaluate the association between LIF and RA in respect of Nanog expression in hTS cells. In another embodiment, tNSCs are treated with LIF and subjected for measurement of Nanog expression by flow cytometry (FIG. 18a). In one embodiment, the tNSCs are treated with about 1000, about 750, about 600, about 550, about 525, about 500, about 450, about 400, about 350, about 300, about 250, about 200, about 150, about 125, about 100, about 75, about 50, or about 25 Units/mL of LIF. In another embodiment, the tNSCs are treated with 1-1000, 1-500, 1-450, 1-400, 1-350, 1-300, 1-250, 1-200, 1-150, 1-125, 1-100, 1-75, or 1-50 Units/mL of LIF. In another embodiment, the tNSCs are treated with 500, 250, and/or 125 Units/mL of LIF.

In one embodiment, the hTS cells are exposed to LIF for 1, 2, 3, 4, 5, 6, 7, 8, 9, or 10 days. In another embodiment, the hTS cells are exposed to LIF overnight. In another embodiment, the hTS cells are exposed to LIF for 3, 6, 12, 15, 18, 22, 24, 30, 36, 48, 60, 72, 84, 96, 108, 120, 132, 144, 156, 168, 180, 192, 204, 216, 228, 240, or 252 hours. In another embodiment, the hTS cells are exposed to LIF for about 1 to 20, about 1 to 18, about 1 to 15, about 1 to 13, about 1 to 10, about 1 to 9, about 1 to 8, about 1 to 7, about 1 to 6, about 1 to 5, about 1 to 4, or about 1 to 2 days.

In one embodiment, treatment of hTS cells with RA induces Nanog overexpression. In another embodiment, LIF suppresses the RA-induced Nanog in a dose-dependent manner. In another embodiment, LIF exerts an inhibitory action on tNSC development.

One aspect described herein is that LIF interplays with RA on neural differentiation of ES cells. In one embodiment, LIF influences the effect of RA on the pluripotency in hTS cells. Results showed that RA induced overexpression of Nanog and Oct4 but not Cdx2 and Sox2 in hTS cells (FIG. 18b). In the isthmus region of the brain, Nanog expression was observed in 62.5% in LIF-induced cells (FIG. 1F, left and right panel) but only 26.9% in RA-induced cells (FIG. 18b). It was also observed that a higher level of LIF generally repressed the RA-induced Nanog and withdrawal of LIF significantly enhanced the RA-induced Nanog expression (FIG. 18a). These results indicated that as hTS cells move towards the isthmus. In one embodiment, RA maintains cellular pluripotency by Nanog expression.

In one embodiment, implantation of tNSCs in an RA-enriched microenvironment facilitates the continuous proliferation of stem cells in vivo. In another embodiment, the tNSCs are implanted into the brain. In another embodiment, the tNSCs are implanted or injected into the hippocampus, cerebral cortex, striatum, septum, diencephalon, mesencephalon, hindbrain, or spinal cord basal ganglia. In another embodiment, the tNSCs are implanted into the striatum of brain. In another embodiment, the tNSCs are implanted or injected into any part of the central nervous system. In another embodiment, the tNSCs are implanted or injected into the nerve terminal area of the cells that degenerate in the particular neurodegenerative disorder. In another embodiment, the tNSCs are implanted or injected into midbrain in substantia nigra pars compact. In another embodiment, the tNSCs are implanted or injected into the nerve terminal area in the forebrain. In another embodiment, the tNSCs are implanted or injected into the ventricular system. In another embodiment, the tNSCs are implanted or injected into the lateral ventricle.

G Protein Signaling in the Maintenance of Multipotency in tNSCs

Figure 3:
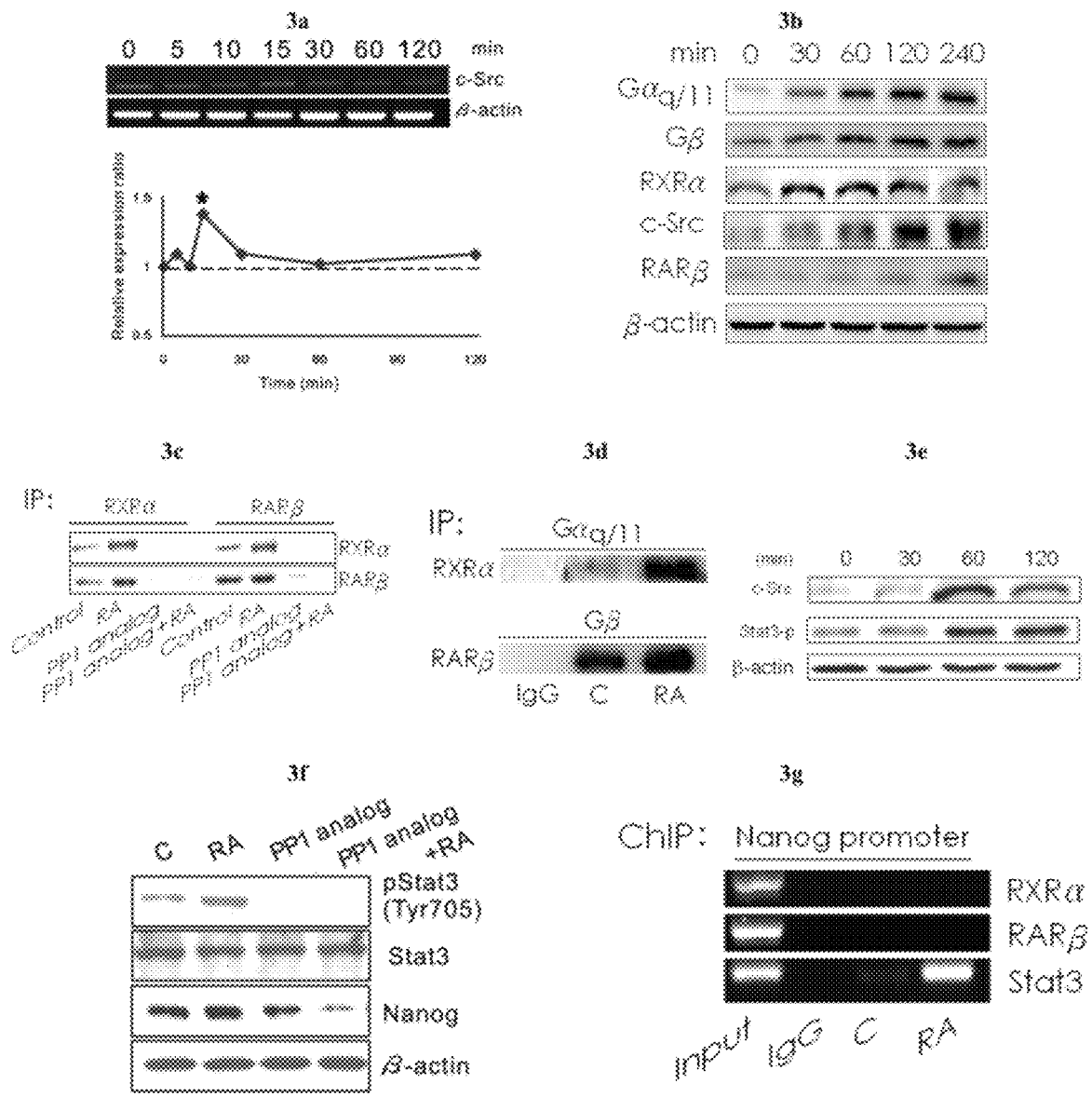
FIG. 3 illustrates RA-induced gene expression. (3a) Illustrates the effect of RA (10 μM) in the activation c-Src/Stat3/Nanog pathway in the tNSCs. RA induced apparent expression of c-Src, peaking at 15 min and then sustaining at a lower levels determined by RT-PCR analysis (n=3). (3b) Shows RA stimulated RXRα, c-Src and RARβ expression at 30 min, 1 h, 2 h, and 4 h, respectively, by western blot analysis. RA induction promotes both Gαq/11 and Gβ expressions in 30 min, suggesting the involvement of G proteins signaling. (3c) Immunoprecipitation (IP) assays demonstrate RA induced direct binding between RXRα and RARβ; however, this interaction is blocked by c-Src inhibitor PP1 analog, indicating that c-Src is involved in RXRα and RARβ binding to form a scaffolding protein complex. (3d) IP assay analysis shows that RXRα has an independent binding interaction with Gαq/11 while RARβ has an independent binding interaction with Gβ. (3e) Illustrates a Western blot analysis of RA induced early production of c-Src, apparent phosphorylation of Stat3 at Tyr705 site and activation of Nanog at 1 h in hTS; β-actin utilized for control sample. (3f) This rapid production of c-Src protein then induced phosphorylation of Stat3 at Tyr705 site as well as overexpression of Nanog by Western blotting assay. The c-Src inhibitor PP1 analog (4 μM) inhibited the RA-induced phosphorylation of Stat3 at Tyr 705 and expression of Nanog by Western blot analysis. This inhibitory action could not be rescued by adding RA. (3g) Illustrates the chromatin immunoprecipitation assay (ChIP) assay analysis of RA stimulated binding interaction of Stat3 and Nanog promoter. Input: lysate, C: control.

Another aspect described herein is a method to investigate how tNSCs sustain their multipotency status. In one embodiment, RA induces c-Src mRNA expression peaks at about 15 min (FIG. 3a). Another embodiment described herein evaluates the GPCR signaling pathway based on RA stimulated expression of RXRα, c-Src and RARβ by Western blot analysis (FIG. 3b). In one embodiment, RA promotes both $G\alpha_{q/11}$ and Gβ expressions in 30 min. In another embodiment, analysis of immunoprecipitation (IP) assays demonstrate that RA induces direct binding between RXRα and RARβ; however, this interaction is blocked by c-Src inhibitor PP1 analog, indicating that c-Src is involved in between RXRα and RARβ to form a scaffolding protein complex (FIG. 3c).

By immunoprecipitation (IP) analysis (FIG. 3d), we observed that RXRα displays binding interactions with $G\alpha_{q/11}$ while RARβ shows binding interactions with Gβ independently. These results are compatible with the 'pull and push' model of GPCR-G protein signaling (Tsai et al., "The ubiquitin ligase gp78 promotes sarcoma metastasis by targeting KAI1 for degradation. Nat. Med. 13, 1504-1509, (2007)).

In one embodiment, the heterodimeric pair of RARs and RXRs plays the role of ligand-activated transcription factors in the nucleus and endogenous cell surface signal molecules. The constitutively activated RXRα breaks up the receptor conformations and recruits c-Src to interact with and/or activate the associated $G\alpha_{q/11}$. In one instance, this non-genomic RA signal transduction assists in the interpretation of non-retinoic acid-response element (RARE)-mediated gene expression (Maden, M., *Nat. Rev. Neuroscience* 8, 755-765 (2007)).

Accordingly, provided herein are strategies for preventing cellular overgrowth before and after transplantation of neural stem cells provided herein. One embodiment describes the use of agents that modulate RA-related pathways thereby preventing, and/or reducing and/or alleviating overgrowth and/or graft rejection.

Proto-Oncogene Tyrosine-Protein Kinase (Src) and Nanog c-Src maintain ES cells at an undifferentiated state (Anneren C. et al., *J Biol Chem.* 279, 590-598 (2004)). Nanog and Stat3 bind synergistically to activate Stat3-dependent promoters (Tones J., et al., *Nat Cell Biol.* 10, 194-201 (2008)). In one embodiment, c-Src induces signal transducer and activator of transcription 3 (Stat3) phosphorylation at Tyr705 site and this action is blocked by c-Src inhibitor protein phosphatase 1 (PP-1) analog, thereby linking the association between c-Src and Stat3 molecules (FIG. 3f). In another embodiment, Stat3 acts directly on the Nanog promoter (FIG. 3g). In another embodiment, Stat3 does not act directly on the Nanog promoter. In another embodiment, RXRα acts directly on the Nanog promoter. In another embodiment, RXRα does not act directly on the Nanog promoter. In another embodiment, RARβ acts directly on the Nanog promoter. In another embodiment, RARβ does not act directly on the Nanog promoter. In another embodiment, RA induces overexpression of c-Src, pStat3 (FIG. 3e) and Nanog (FIG. 1e) in hTS cells. In another embodiment, both RXRα and RARβ play a transductional role in response to RA via GPCR-G protein signaling.

Figure 4:
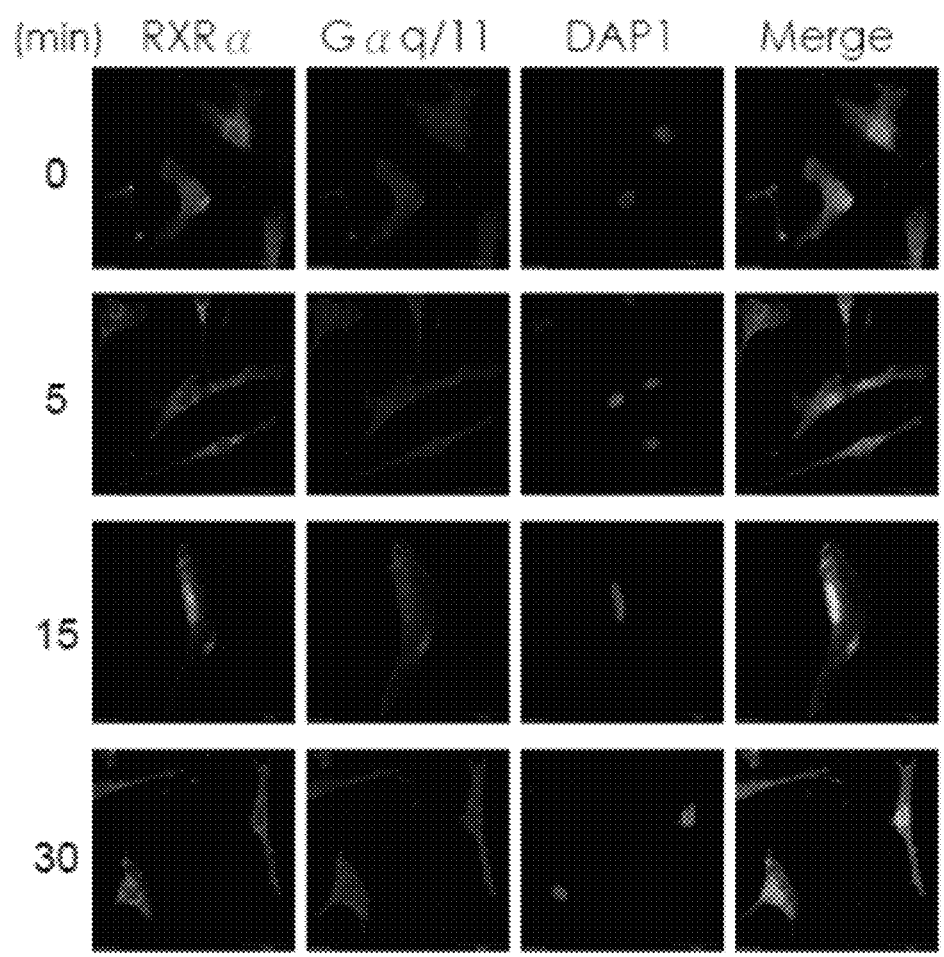
FIG. 4 illustrates the double immunogold fluorescence transmission electron microscopy (IEM) assay results. RA-induced binding interaction between the small gold particle-labeled RXRα (6 μm) and the large gold particle-labeled Gαq/11 (20 μm) at the plasma membrane is shown. By dynamic confocal immunofluorescence microscopy, immunostained RXRα and Gαq/11 appeared primarily in a homogenous feature in either cytoplasm or nucleus (FIG. 4, upper panel). By treatment with RA for 5 min, the cytosolic RXRα intensity increased at the peri-nuclear regions while the nuclear intensity decreased (first column), indicating a cytosolic translocation after stimulation. The nuclear RXRα intensity became prominent at 15 min, while the cytosolic intensity decreased. These phenomena suggest that an increase of activity in nucleus maintains a steady-status in the cell. An apparent cytosolic translocation was observed again in 30 min. The compartmental changes of Gαq/11 expression, on the other hand, were similar to that of RXRα (second column).

Described herein, in one embodiment, is a method to maintain multipotency in tNSCs, the method comprising activating the c-Src/Stat3/Nanog transcription pathway. In another embodiment, interaction of c-Src and $G\alpha_{q/11}$ activates of c-Src/Stat3/Nanog pathway. To further verify the direct interaction between RXRα and $G\alpha_{q/11}$ by imaging study, double immunogold fluorescence transmission electron microscopy (IEM) was utilized. RA induced binding interaction between the small gold particle-labeled RXRα (6 μm) and the large gold particle-labeled $G_{\alpha q/11}$ (20 μm) at the plasma membrane (FIG. 4). By dynamic confocal immunofluorescence microscopy, both immunostained RXRα and $G_{\alpha q/11}$ appeared primarily in a homogenous feature in either cytoplasm or nucleus (FIG. 4, upper panel). By treatment with RA for 5 min, the cytosolic RXRα intensity increased at the peri-nuclear regions while the nuclear one decreased (FIG. 4, first column), indicating a cytosolic translocation after stimulation. The nuclear RXRα intensity became prominent at 15 min, while the cytosolic one decreased (FIG. 3a).

In one embodiment, an increase of activity in a cell nucleus maintains a steady-status in the cell. An apparent cytosolic translocation was observed again in 30 min. The compartmental changes of $G_{\alpha q/11}$ expression, on the other hand, were similar to that RXRα (FIG. 4, second column). In one embodiment, there was an apparent accumulation of $G_{\alpha q/11}$ observed at the cell membrane at 30 min after stimulation. In another embodiment, RA enables promotion of both RXRα and $G_{\alpha q/11}$ synthesis and translocalization constitutively in hTS cells.

Accordingly, provided herein is the use of RA acting on hTS cells via G protein-coupled receptor (GPCR)-G proteins signaling at the plasma membrane, which is distinguishable from genomic RA/RXRs/RARs pathways, for generation of tNSCs. As shown here, RA acts through Nanog and Oct4, but not Cdx2 and Sox2 pathways, in differentiating hTS cells into tNSCs. Also provided herein is the use of RA-induced Nanog activation for the maintenance of multipotency and self-renewal in tNSCs. Provided herein is the use of RA activation of G protein-coupled receptor (GPCR)-G protein signaling, and concomitant activation of the RXRα/Gαq/11/c-Src/Stat3/Nanog pathway, for the maintenance of multipotency in tNSCs. Provided herein is the use of the heterodimers of RXRα and RARβ functioning as signaling molecules at the plasma membrane for the maintenance of multipotency in tNSCs. Also provided herein is the use of RA induced differentiation of hTS cells into neural stem cells (NSCs) by overexpression of Nanog for the maintenance of pluripotency and renewal.

The tNSCs described herein express retinaldehyde dehydrogenase (RALDH)-2 and -3 which aids neurogenesis. The presence of RALDHs and absence of CD33 in the tNSCs described herein indicates that the tNSCs are superior to hES cells in the differentiation into sensorimotor neurons. Accordingly provided herein is the use of tNSCs described herein for neurogenesis and/or regenerative medicine.

Figure 20:
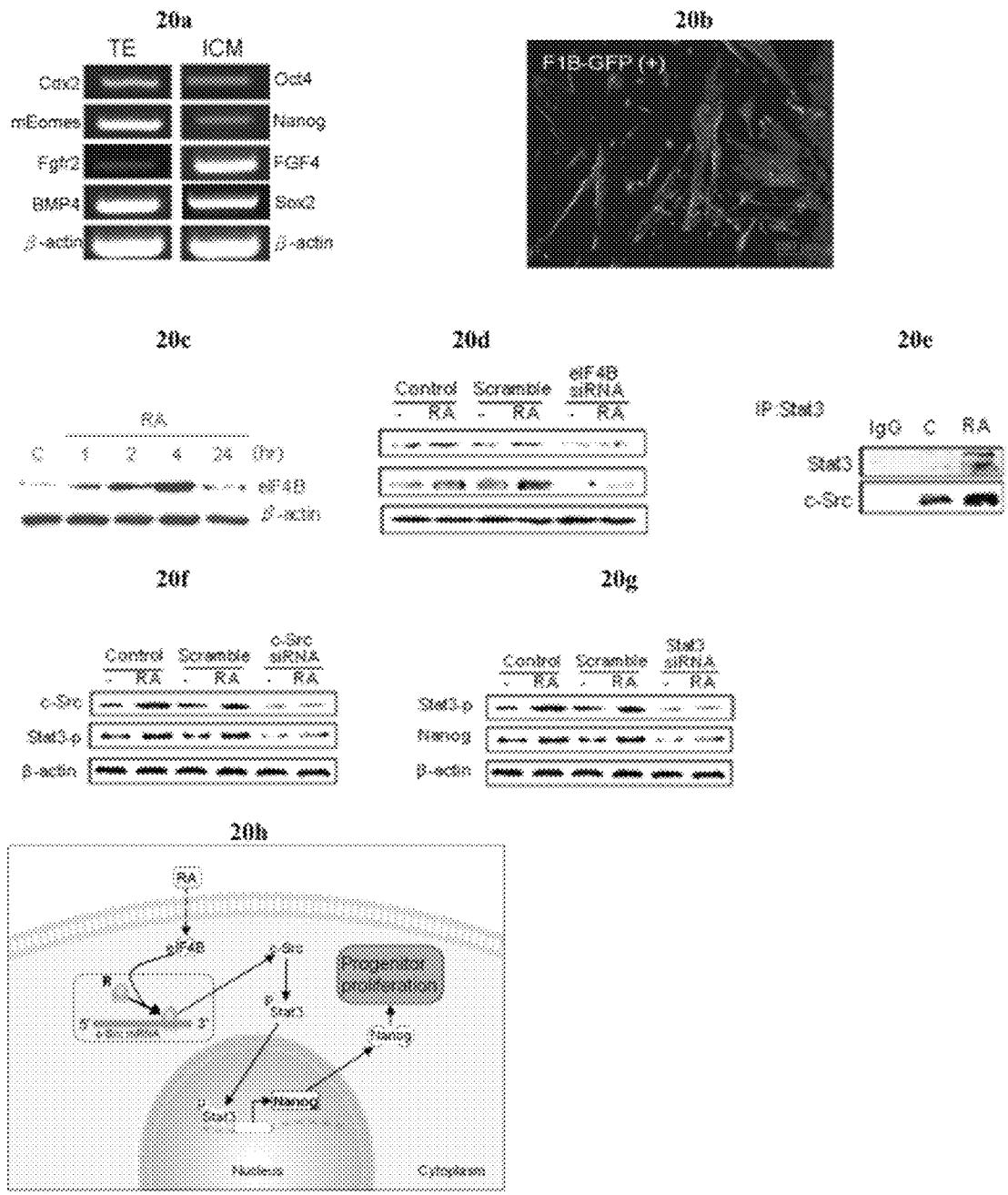
FIG. 20: (20a) illustrates the expression of specific genes of both ICM and trophectoderm (TE) by RT-PCR; (20b)

In the developing striatum and hippocampus, an increased Src kinase activity coincides with the peak period of neuronal differentiation and growth. However, RA can suppress phosphorylation of ribosomal S6 kinase and its downstream eukaryotic Initiation factor 4B (eIF4B) by 24 hr incubation to cause growth arrest of many cell types. RA induces a rapidly transient expression of c-Src mRNA peaking at 15 min (FIG. 3a), followed by production of c-Src protein at 1 hr in hTS cells (FIG. 3e). In one embodiment, c-Src mRNA contains an internal ribosome entry site. In another embodiment, RA transiently produces eIF4B peaking at 4 hr, but fading away at 24 hr (FIG. 20c). This action was inhibited by using eIF4B siRNA (FIG. 20d). The involvement of mTOR/eIF4EBP1 signaling (mechanistic target of rapamycin/eukaryotic Initiation factor 4E binding protein 1) was excluded (FIG. 20b). In another embodiment, RA activates eIF4B for subcellular mRNA localization to produce c-Src.

Active c-Src binds directly to Stat3 (signal transducer and activator of transcription) (FIG. 20e) by phosphorylation at site Tyr705 to produce protein (FIG. 3e). In one embodiment, this action is inhibited by using c-Src siRNA (FIG. 20f). In another embodiment, this action is inhibited by a selective c-Src inhibitor PP-1 analog (FIG. 3f). In another embodiment, a direct action of Stat3 on the Nanog gene promoter is observed by chromatin immunoprecipitation (ChIP) assay (FIG. 3g). In another embodiment, Nanog is produced in 4 hr (FIGS. 3f and 20f), which was able to be blocked by using PP1 analog (FIG. 3f) and Stat3 siRNA (FIG. 20g).

Described herein, in one embodiment, is a method to maintain pluripotency of tNSCs comprising exposure of the cell an inducing agent to modulate the nongenomic eIF4B/c-Src/Stat3/Nanog signaling pathway mediated c-Src subcellular mRNA localization (FIG. 20h). In another embodiment, the inducing agent is RA.

RA and Wnt Signaling

Also provided herein is a method to induce hTS cells into neural stem cells. In one embodiment, the method comprises modulating the Wnt2B/beta-catenin signaling pathway. In another embodiment, the method comprises modulating the RARs-Akt signaling pathway. In another embodiment, the method comprises modulating the Wnt2B/beta-catenin and RARs-Akt signaling pathways. In another embodiment, the hTS cells are induced by treatment with retinoic acid (RA). In another embodiment, the method to induce hTS cells into neural stem cells further comprises activating transcription factor Pitx2. In another embodiment, the method to induce hTS cells into neural stem cells further comprises activating transcription factor netrin (NTN). In another embodiment, the method to induce hTS cells into neural stem cells further comprises activating transcription factors Pitx2 and NTN. In another embodiment, the RAR and RXR exist as a heterodimer bound through its DNA-binding domain (DBD) to the retinoic acid responsive element (RARE) DR-5. In another embodiment, corepressors bind to RAR and recruit histone deacetylase (HDAC) causing transcriptional repression. In another embodiment, the method to induce hTS cells into neural stem cells further comprises activating transcription factors Pitx2 and NTN. In another embodiment, RA is added to hTS cells and transcription is activated by RA binding to the RAR. In another embodiment, RAR binds to RA then recruits coactivators and HAT.

RA-mediated Wnt signaling pathway is a crucial contributor during adult neurogenesis and survival in vivo. Wnt proteins, present in the neural stem cell microenvironment, are key regulators of cellular behavior in early embryogenesis and can maintain neural stem cell potency. In adult neurogenesis, Wnt proteins bind to their receptor Frizzled (e.g., Fzd6) to transduce numerous signaling cascades, for example, by activating the beta-catenin/LEF signaling for specific target genes.

Wnt signals are involved in cell cycle control and morphogenesis during neurodevelopment. Among them, Wnt2B can inhibit differentiation of retinal neurons and has been suggested to be a stem cells factor for NSCs using comparative integromics analysis. In one embodiment, Wnt2B modulates the expression of frizzled family receptor 6 (Fzd6). In another embodiment, Wnt2B induces the expression of Fzd6. In another embodiment, Fzd6 is overexpressed in the presence of Wnt2B. In one embodiment, RA modulates a canonical Wnt2B/Fzd6/β-catenin signaling pathway for the dopaminergic differentiation in hTS cells. In one embodiment, RA induces a canonical Wnt2B/Fzd6/β-catenin signaling pathway for the dopaminergic differentiation in hTS cells.

One embodiment provided herein describes the canonical Wnt pathway as inducing an inhibitory GSK3β, which results in the stabilization of β-catenin for nuclear translocation in cells. In another embodiment, RA rapidly induces phosphorylation of GSK3β at Tyr216 site, downstream effector of Akt2. In another embodiment, RA rapidly induces phosphorylation of GSK3β at Tyr216 site, leading to the phosphorylation of β-catenin at the initial few hours that plays a 'priming' effect for the later canonical Wnt pathway. In another embodiment, these activated Fzd6 and Dvl3 are able to facilitate the interaction of c-Jun N-terminal kinases (JNK) with the cytoskeleton or increase the intracellular $Ca^{2+}$ level, which in turn activates CaMKII for synaptic function in a non-canonical Wnt/$Ca^{2+}$ signaling pathway. As time proceeds, a switch from non-canonical to canonical Wnt pathway occurs, attributing to the phosphorylation of GSK3β at Ser9/21 site. In one embodiment, G protein regulates the transduction of non-canonical Wnt2B signaling at an initial stage. In another embodiment, a canonical Wnt2B signaling occurs at later stage in early developing neuronal differentiation.

HDAC6

Also provided herein is a method to induce hTS cells into neural stem cells, the method comprising modulating histone deacetylase 6 (HDAC6). Histone deacetylase 6 (HDAC6), an enzyme mainly located in the cytoplasm, regulates many biological processes, including cell migration, immune synapse formation, viral infection, and the degradation of misfolded proteins. For example, HDAC6 deacetylates tubulin, Hsp90 and cortactin, and forms complexes with other partner proteins.

HDAC6 is capable of shuttling β-catenin for nuclear localization. In one embodiment, HDAC6 interacts with β-catenin, leading to the nuclear translocation of β-catenin by cellular fractionation assay. In another embodiment, RA induces a novel canonical Wnt2B/Fzd6/β-catenin signaling pathway, allowing nuclear translocation of β-catenin in hTS cells. In the nucleus, β-catenin involves in mediating key gene expression programs or as a docking platform for various transcriptional co-activators to stimulate transcription.

HDAC4

Histone deacetylase 4 (HDAC4) is an important epigenetic regulator of functional hTS cell-induced neural stem cells. HDAC4 inhibits cell-cycle progression and protects neurons from cell death. Transcriptional regulation by RARs involves modifications of chromatin by HDACs, which are recruited to RA-target genes by nuclear co-repressors, determining the differential response to RA.

LEF/TCF/Pitx2

Lef-1 and PITX2 function in the Wnt signaling pathway by recruiting and interacting with beta-catenin to activate target genes. PITX2 interacts with two sites within the Lef-1 protein. Furthermore, beta-catenin interacts with the PITX2 homeodomain and Lef-1 interacts with the PITX2 C-terminal tail. Lef-1 and beta-catenin interact simultaneously and independently with PITX2 through two different sites to regulate PITX2 transcriptional activity. These data support a role for PITX2 in cell proliferation, migration, and cell division through differential Lef-1 isoform expression and interactions with Lef-1 and beta-catenin.

Netrin 1 (NTN1)

The molecular mechanism of NTN1 is considered as primarily involved in axonal guidance and control of neuronal cell migration.

Activation of Wnt/PS1/PI3K/Akt Pathway and Inhibition of GSK3-Beta by RA

Increased Wnt signaling expands the stem cell pool and forces expression of a stabilized β-catenin resulting in a large brain owing to increased numbers of proliferative progenitors and a corresponding decrease in differentiated neurons (Chem, A. et al., Science 297, 365-369, (2002)). β-catenin has a dual role, as a junctional protein and in canonical Wnt signaling, the phenotype could be due to increased Wnt signaling (which is linked to NSC self-renewal) or to increased junctional stability.

PI3K/Akt Signaling

Described herein, in one embodiment, is a method of maintaining pluripotency of tNSCs, the method comprising modulating the PI3K/Akt signaling pathway. The G-protein beta/gammaheterodimers also activate Phosphoinositide-3-kinase, regulatory subunit 5 (PI3K regclass IB (p101)) that leads to Phosphoinositide-3-kinase, catalytic, gammapolypeptide (PI3K cat class IB (p110-gamma))-mediated conversion of phosphatidylinositol 4,5-biphosphate (PtdIns(4,5)P2) to phosphatidylinositol3,4,5-triphosphate (PtdIns(3,4,5)P3) [3]. PtdIns(3,4,5)P3 is a second messenger that directly binds to 3-phosphoinositide dependent protein kinase-1 (PDK(PDPK1)) and V-akt murine thymoma viral oncogene homolog 1 (AKT(PKB)). PDK(PDPK1) phosphorylates AKT(PKB) and activates AKT signaling[4].

PI3K/Akt signaling regulates self-renewal and differentiation capacity in the following stem cell systems. The derivation of pluripotent embryonic germ (EG) cells from primordial germ cells (PGC) is enhanced in PGC-specific Pten-deficient mice (Kimura T, et al., Development 130: 1691-1700, (2003)).

Using conditional activation of Akt signaling, it is shown that in one embodiment, PI3K/Akt signaling plays a role in the activation of resting stem cells. In another embodiment, PI3K/Akt signaling plays a role in the proliferation of progenitors in adult epidermis.

In one embodiment, PI3K/Akt signaling promotes the self-renewal of stem cells, rather than the generation of committed progenitors in these culture-adapted stem cells. In one embodiment, RA modulates activation of Akt3/mTOR signaling that elicits the subcellular mRNAs translation encoding proteins RXRα and RARβ in hTS cells. In one embodiment, RA induces activation of Akt3/mTOR signaling that elicits the subcellular mRNAs translation encoding proteins RXRα and RARβ in hTS cells. In another embodiment, an inducing agent inhibits activation of Akt3/mTOR signaling. In another embodiment, the selective movement and interactions of the RXRα/Gα$_{q/11}$ and RARβ/Gβ signaling pathways are initiated independently.

In another embodiment, RA regulates genetic program transcriptional activities for cell functions depending on a pleiotropic and cellular context-dependent manner; i.e., the output phenotype is a combination of the effects of AP-1 and/or beta-catenin-LEF/TCF inhibition and RARE activation.

GSK3/3 Regulates Microtubule Assembly hTS cells embrace the major GSK3β functions that initial activation of GSK3β promotes neuronal differentiation and later inactivation promotes progenitor proliferation in neurodevelopment. In resting cells, the basal activity of GSK3 is generally relative high while exposure of the cells to guidance cues can reduce its specific activity by between 30-70% in 10 min. GSK3β has a strong preference for its substrates that are already phosphorylated; therefore, the precedent primed β-catenin becomes a favorable one for the later inhibitory GSK3β in the canonical Wnt2B signaling.

In one embodiment, the rapidly spatiotemporal active GSK3β phosphorylates MAPT localizes in axonal growth core, leading to the activation of tubulin heterodimer (FIGS. 21a and 21b) that promote microtubule assembly, neuronal polarity, and axon outgrowth consistent with the notion that activation of GSK3β is involved in the axonal microtubule assembly. Moreover, GSK3β is also able to regulate phosphorylation of CRMP-2, contributing to microtubule assembly, whereby CRMP-2 preferentially binds to tubulin heterodimer which is apparently distinct from that of MAPT. A mutant of CRMP-2 inhibits axonal growth and branching in a dominant-negative manner.

Provided herein in one embodiment is a mechanistic basis to assist in the explanation in vivo that GSK-3 signaling is an important mediator of homeostatic controls that regulate neural progenitors in developmental brain. In another embodiment, the initial local activation of PI3K/Akt pathway induces activation of GSK3β at Tyr216 in hTS cells. In one embodiment, initial local activation of PI3K/Akt pathway is distinct from the inactivation of GSK3β induced by Ser9/21 phosphorylation in hippocampal neurons isolated from E18 rat embryo. In one embodiment, phosphorylation at different sites in GSK3β results in different cellular fate, depending on the time factor. Phosphorylated GSK3β prevents the DNA binding of calcineurin-induced NFAT1 by promoting nuclear export. NFAT plays a central role in promoting gene transcription, including cytokine genes in T-cells during the immune responses. These facts explain, at least partly, why both hTS cells and tNSCs possess immune advantages that facilitate intracranial transplantation in PD rats.

G Protein and Neuronal Plasticity

The high degree of autonomy in NSCs permits rapidly local responses to guidance cues by the selective localization and translation of subsets of mRNAs during neurogenesis. Wherein mTOR typically upregulates protein synthesis via phosphorylating key regulators of mRNA translation and ribosome synthesis in NSCs. In hTS cells, active Akt3/mTOR signaling triggers mRNA translation to independently synthesize RXRα and RARβ proteins that activate Gα$_{q/1}$ and Gβ signaling pathways, respectively. Wherein, local CREB1 is activated and plays a role of inducible gene expression that transiently targets TH gene for transcription to produce neurotransmitter dopamine. It has been shown that RA promotes RARα expression in the dendritic RNA granules and activates local glutamate receptor 1 (GluR1) synthesis, implicating a homeostatic synaptic plasticity. Therefore, an activation of dopamine D1/D5 receptor, the upstream enhancer of CREB, can induce GluR1 insertion at synaptic site in neurons.

Provided herein, in one embodiment, is a molecular model for the study of RA signal-related plasticity.

Transcription Factors for Dopaminergic Neurogenesis

In one embodiment, interaction of β-catenin and CREB1 in the nucleus represents a mainstream in TH transcription.

In one embodiment, the active β-catenin binds to lymphoid enhancer factor 1/T cell factor 1 (LEF1), leading to the switch of LEF1 from repressor to activator of transcription. LEF1 then recruited and interacted with Pitx2, member of a superfamily of bicoid-related factor. In one embodiment, LEF1 promotes Pitx2 gene transcription. In another embodiment, LEF1 promotes Pitx3 gene. In another embodiment, LEF1 promotes both Pitx3 and Pitx2 gene transcription. In one embodiment, β-catenin, Pitx2, and LEF1 synergistically interact to regulate the LEF-1 promoter.

Furthermore, the transient nuclear active NFAT1 plays as transcription factor to produce cytokines and TNF-α for immune responses. However, this action was unlikely to occur in the present case because the phosphorylated GSK3β enables to inhibit the DNA binding of calcineurin-induced NFAT1 in the nucleus and to promote nuclear export. Therefore, active cytoplasmic NFAT1 would interact and activate cytoplasmic transcription factor myocyte enhancer factor 2A (MEF2A) (FIGS. 22c and 22d) because this action was able to be inhibited by NFAT1 siRNA (FIG. 22e). Notably, the rapid inducible CREB1 entered the nucleus and transcribed MEF2A gene that produced MEF2A protein (FIG. 22f). MEF2A might function in multiple ways at gene transcription (FIG. 22g), including transcription itself via auto-regulation to produce more MEF2A, transcription TH gene for dopaminergic specification, transcription SNCA gene for SNCA/MAPT/parkin complex formation, and interaction with EP300 and Pitx2, which was inhibited by MEF2A siRNA (FIG. 22h).

In one embodiment, active ER300 targets the HDAC6 gene and the TH gene. In one embodiment, active ER300 targets the HDAC6 gene. In another embodiment, active ER300 targets the TH gene. In one embodiment, active ER300 promotes the transcription of the HDAC6 gene and the TH gene. In another embodiment, active ER300 inhibits the transcription of the HDAC6 gene and the TH gene. In another embodiment, the HDAC6 transports β-catenin for nuclear translocalization.

Provided herein, in one embodiment, is the characterization of an executive transcription complex that is formed and destined for TH gene transcription. For example, CREB1, EP300, and MEF2A are able to target the promoter of the TH gene while β-catenin, LEF1, and Pitx2 perform as co-activators of the enhancer during transcription processes. Provided herein, in one embodiment, are methods to understand how these genes manipulate the balance between differentiation and proliferation in dopaminergic NSCs that have implications for the evaluation of disease mechanisms (e.g., PD).

Multifarious Faces of CaMKII

In developing NSCs, local calcium influx through either voltage-gated calcium channels or neurotransmitter receptors results in the activation of CaMKII, delivering several messages forwards. In one embodiment, the spatiotemporal CaMKII triggers the c-Src mRNA localization via activated eIF4B to synthesize c-Src protein, resulting in the activation of Nanog for self-renewal and proliferation in hTS cells for excitation-transcription coupling. In another embodiment, CAMKII triggers activation of local CREB1, leading to a retrograde trafficking to the nucleus to target gene MEF2A for transcription. MEF2A mediates cellular functions not only in neuronal differentiation and proliferation, but also in skeletal and cardiac muscle development. In one embodiment, CaMKII activates MAPT mediating parkin protein and in turn, MAPT activates tubulin heterodimer for microtubule assembly (FIGS. 22a and 22j). These results suggest that early spatiotemporal CaMKII signal is sufficient for the activation of tubulin to promote microtubule assembly, neuronal migration, and neuronal polarization in early developing NSCs that ensure proper connectivity with striatal targets in the brain.

L-type calcium channels regulate intracellular calcium for homeostasis in another way, are involved in excitation-neurogenesis in adult NSCs. An elevated potassium chloride (KCl) level leads to membrane depolarization, resulting in an influx of calcium through L-type voltage-sensitive calcium channels which is sufficient to induce mitochondrial dysfunction via the crosstalk between ER and mitochondria in neurons. In one embodiment, RA modulates intracellular ER calcium associated with L-type calcium channels.

CaMKII (calmodulin (CaM)-dependent protein kinase II), a downstream effector of L-type $Ca^{2+}$ channels, exhibits a lower affinity for $Ca^{2+}$/calmodulin in response to transient low-amplitude calcium spikes. In one embodiment, RA modulates a spatiotemporal activation of CaMKII. In another embodiment, RA induces a spatiotemporal activation of CaMKII. In another embodiment, RA inhibits a spatiotemporal activation of CaMKII.

CaMKII directly phosphorylated and activated CREB1 by IP assay (FIG. 21c) compatible with the previous study that CaMKII encodes L-type calcium channel activity locally to signal to nuclear CREB in excitation-transcription coupling. Since axons contains a variety of mRNA encoding specific protein synthesis locally, including CaMKII, calcineurin, and CREB1 in developing neurons, suggesting the extrinsic RA-triggered mRNA translational machinery happens to them because they were able to be inhibited by eukaryotic initiation factor 4B (EIF4B) siRNA (FIG. 21d). Therefore, this local CREB1 enables the retrograde trafficking for specific transcriptional processes in the nucleus responsible for the signal of distal axons. These results suggested a rapidly inducible gene transcription upon the extracellular cues.

These results first explored that the $G\alpha_{q/11}$ signal-derived CaMKII excitation was involved in the maintenance of self-renewal of tNSCs. Together, these results suggested the importance of axonal behaviors in early neurogenesis. SNCA interacts with the phospholipid membranes and plays crucial roles in the pathogenesis of neurodegenerative disorders including PD and Alzheimer's disease.

Calcineurin/NFAT1 Signaling

In one embodiment, RA modulates the production of calcineurin. In one embodiment, RA induces production of calcineurin. In another embodiment, ER calcium is linked to calcineurin/NFAT1 signaling, consistent with previous studies. In another embodiment, RA induces a transient interaction of NFAT1 and importin, a nucleocytoplasmic transporter, leading to the NFAT1 nuclear translocation by cell fractionation assay. This temporal effect of NFAT1 is thought to be one mechanism by which cells distinguish between sustained and transient calcium signals. In one embodiment, RA-induced calcineurin/NFAT1 signaling is involved in the early neurogenesis.

Cellular Remodeling at Initial Neurogenesis

Provided herein, in one embodiment, is a method for inducing molecular processes during the transition of hTS cells towards tNSCs. In one embodiment, the molecular processes are induced by RA. In one embodiment, the molecular cascades are examined at two time points: 4 hr (early) and 24 hr (later). In one embodiment, the molecular events occur in two phases. In a specific embodiment, one phase includes the spatiotemporal responses in morphogenesis (e.g., FIG. 23; early phase; grey line). In another specific embodiment, one phase includes the gene transcription in cell differentiation and proliferation (e.g., FIG. 23; later phase; black line).

In one embodiment, the mechanisms in early neuronal morphogenesis are characterized. Once the stem cells sense the external guidance signal, a variety of specific subcellular mRNA localizations initiate rapidly in responsiveness to make up specific proteins locally beyond the far transcription processes in the nucleus. Through the protein-protein interaction and 'sensory experience' these local proteins accumulate at the subcellular regions to initiate growth cone formation in early developing NSCs. In accompany with the gene transcription the asymmetric division begins. For instance, the presence of β-catenin is visible at the synaptic membrane after RA treatment for 5 min (FIG. 23g) and the local activated CREB1 travels back to the nucleus to target gene MEF2A for transcription.

In one embodiment, a series of molecular processes synergistically occur to regulate mitochondrial function, lipid metabolism of membrane, axonal growth, neuronal migration and plasticity, and microtubule assembly, including but not limited to RXRα, RARβ, β-catenin, Akt, CREB1, mTOR, CaMKII, calcineurin, c-Src, GSK3β, SNCA, and MAPT. In another embodiment, the transcription at TH gene by MEF2A, EP300, and CREB1 represent an inducible gene expression, which induces chromatin looping from chromosome territories, facilitating the later gene transcription. In another embodiment, components of RA-induced G protein signaling play a key role in neuronal morphogenesis and also an integral part in activating transcription at TH gene.

Described herein is a balance between the differentiation and the proliferation to maintain in a steady-state of tNSCs in vitro. In one embodiment, neural differentiation is controlled by modulating RA-signal transduction. Manipulation of hTS cells is enabled more efficiently in vitro before further applications in regenerative medicine or drug discovery through the understanding of these regulatory mechanisms.

tNSCs Possess Immune Privilege

One embodiment provided herein describes a method of treating a neurological disorder using at least one tNSC wherein the cell is immune privileged. In another embodiment the tNSC does not elicit an immune response. In another embodiment the tNSC does not elicit an immune response from a T cell, B cell, macrophage, microglia, NK cell, or mast cell. In another embodiment the tNSC inhibits an immune response. In another embodiment the tNSC has reduced immunogenicity. In another embodiment, the tNSC does not lead to tumor formation. In another embodiment, the tNSC is designed to be immune privileged. In another embodiment provided herein describes a method of treating a neurological disorder using a population of tNSC cells wherein the cells are immune privileged. In another embodiment, the application of stem cells or their derivatives as cell therapies benefits from the understanding of their immunogenicity to assist in the determination of application of immunosuppression agents postimplantation.

Another aspect described herein is a method to examine and compare the expression of immune-associated genes and markers among hTS cells, tNSCs and hES cells. In one embodiment, expression is examined by flow cytometric analysis.

Examples of immune-associated genes and markers among hTS cells, tNSCs and hES cells include but are not limited to HLA-ABC, HLA-DR, CD14, CD44, CD73, CD33, CD34, CD45, CD105, and CD133. In another embodiment, the expression of HLA-ABC in hTS cells and tNSCs is higher in tNSCs compared to that in hES cells. In one embodiment, negative expression of HLA-DR is observed in all three stem cells (FIG. 2e). In another embodiment, the expression of HLA-ABC in hTS cells (99.4%) and tNSCs (99.7%) was much higher in tNSCs compared to that in hES cells (12.9%) (FIG. 2e). In another embodiment, no difference in CD14 and CD44 expressions was seen among hTS cells, tNSCs and hES cells. In another embodiment, high levels of CD73 were expressed in hTS cells and tNSCs compared to the negative expression levels in hES cells (FIG. 2f). In one embodiment, the tNSCs possess characteristics of mesenchymal stem cells, which are favorable for the proliferation of glial cells.

In another embodiment, CD33, which contains immunoglobulin structure at extracellular portion and is a transmembrane receptor, is expressed in hTS and hES cells but not tNSCs (FIG. 2f). In another embodiment, the absence of CD33 in tNSCs is in favor of cell therapy because of its association with immune defense. Accordingly, provided herein are tNSCs having low levels of expression of CD33 and thereby having low immunogenicity.

In one embodiment, no differences in intensities are found among them in the expression of mesenchymal stem cell marker CD105. In another embodiment, low levels of expression of the cancer stem cell marker CD133 are found in tNSCs compared to hTS cells and hES cells. In another embodiment, low levels of expression of the cancer stem cell marker CD133 (11.8%) are found in tNSCs compared to hTS cells (93.6%) and hES cells (98.8%) (FIG. 2h). Accordingly, provided herein are tNSCs having low levels of expression of CD133 and thereby having low tumorigenicity.

Further provided herein are selective populations of CD133+ tNSCs that are useful for transplantation and tissue regeneration for stem cell therapy. Also provided herein are tNSCs with immune-privileged status, which are viable candidates for cell-based therapy.

In one embodiment, RA induces the changes in expression of immune-related markers, for example, cells with CD34(+) increased but with CD133(+) decreased. In another embodiment, RA induces the differentiation of CD34(+) hES cells into smooth muscle progenitor cells. In another embodiment, autologous transplantation of tNSCs with CD34(+) immunoselected grafts is feasible in children with high-risk neuroblastoma.

Post-Implantation Differentiation and Proliferation

The association between RA and the retinoic acid-response element (RARE) in neurogenesis (Maden, M. et al., *Nat. Rev. Neuroscience.* 8, 755-765, (2007)) is known, however the existence of non-RARE action is poorly understood. In one embodiment, RA induces activation of RXRα/RARβ/c-Src complex via "pull and push" mechanism of G protein-coupled receptors (GPCRs) signaling. In another embodiment, RXRα is first activated by interaction with $G\alpha_{q/11}$ followed by activation of c-Src and later RARβ in 2 h to form a complex (FIGS. 3a and 3b). Among them, c-Src subsequently induces Nanog overexpression through Stat3 for the maintenance of multipotency and self-renewal of those hTS cell-derived NSCs.

This signaling pathway implies that it is not necessary for RA to enter the cell to trigger the classical RA/RXR/RAR/RARE pathway, instead, RA activates G protein $G\alpha_{q/11}$ via GPCR signaling compatible with the notion of signal transduction. Accordingly, provided herein, in one embodiment, are methods for control of RA-mediated regulation of multipotency and self-renewal of NSCs, and manipulation of hTS cells and/or neural stem cells before and after transplantation. In another embodiment, Wnt and RA impact caudal type homeobox 1 (Cdx1) through an atypical RARE and Lef/transcription factor (Tcf)-response elements (LRE), respectively, in the proximal promoter.

In one embodiment, RA induces hTS cells differentiation into dopaminergic NSCs via a classical RA/RARE signaling pathway to maintain the stem cell properties. In another embodiment, is a non-RARE signaling pathway via activation of Wnt/β-catenin signaling cascade that generates the functional dopaminergic NSCs. In another embodiment, impairment of the non-RARE signaling causes dysfunction or loss of dopamine production, resulting in the progressive degenerative change of dopaminergic neurons. Accordingly, provided herein, in another embodiment, is a neural stem cell that differentiates to dopaminergic neurons via activation of non-RARE signaling pathways.

RA activates the protein kinase C (PKC) pathway prior to induction of RAR-β expression at 6 h. RA causes a transient 1.3-fold increase in intracellular diacylglycerol (DG) at 2 min and a translocation of the gamma isozyme of PKC (PKC-γ) within 5 min. Kurie J. M. et al., *Biochim Biophys Acta.* 1993, 1179(2):203-7. These findings reveal that PKC pathway activation is an early step in RA-mediated human TC differentiation and that PKC-γ can potentiate the effects of RA on RAR transcriptional activation. Accordingly, provided herein are methods to control hTS cell differentiation. In one embodiment, modulation of the PKC signaling pathway controls hTS cell differentiation.

Bone morphogenetic protein 4 (BMP4) together with LIF supports expansion of undifferentiated mES cells. BMP4 induces trophoblastic differentiation of hES cells Qi X, et al., *Proc Natl Acad Sci USA.* 2004; 101:6027-6032. BMP induction of Id proteins suppresses differentiation and sustains embryonic stem cell self-renewal in collaboration with STAT3. Ying, Q. L., et al., *Cell.* 2003; 115:281-292. Bone morphogenetic proteins (BMPs) act in combination with LIF to sustain self-renewal and preserve multilineage differentiation, chimera colonization, and germline transmission properties. Xu R H, et al., *Nat Biotechnol.* 2002; 20: 1261-1264. Accordingly, provided herein, in one embodiment, is a method for inducing dopaminergic differentiation of tNSCs described herein by modulation of PKC and/or Bone morphogenetic protein (BMP).

Treatment of Disease

Provided herein is a method to treat a disorder, wherein the method comprises transplanting a pure population of neurons or a complex of specific neural stem cell populations to a patient, wherein the patient is in need thereof. In one embodiment, the patient is diagnosed with a neurological disease. In another embodiment, the patient is diagnosed with a neuropsychiatric disorder. In another embodiment, the patient is diagnosed with a neurodegenerative disorder. In another embodiment, the pure population of neurons comprises dopaminergic neurons.

Any method described herein can be used to treat a disease or disorder. In one embodiment, the disease is a neurological disease. In another embodiment, the disease is a neurodegenerative disease or disorder. Non-limiting examples of neurological disorders include Parkinson's disease, Alzheimer's disease, Huntington's disease, Amyotrophic lateral sclerosis, Friedreich's ataxia, Lewy body disease, spinal muscular atrophy, multiple system atrophy, dementia, schizophrenia, paralysis, multiple sclerosis, spinal cord injuries, brain injuries (e.g., stroke), cranial nerve disorders, peripheral sensory neuropathies, epilepsy, prion disorders, Creutzfeldt-Jakob disease, Alper's disease, cerebellar/spinocerebellar degeneration, Batten disease, corticobasal degeneration, Bell's palsy, Guillain-Barre Syndrome, Pick's disease, and autism.

Accordingly the tNSCs described herein are suitable for treatment of neurodegenerative disorders including, and not limited to, Parkinson's disease, Alzheimer's disease, Huntington's disease, spinal cord injury, glaucoma, or the like.

In addition, the tNSCs also express neurotransmitter serotonin. Accordingly, one embodiment describes the use of tNSCs in treatment of neuropsychiatric disorders. Non-limiting examples of neuropsychiatric disorders include depression, schizophrenia, dementia, autism, attention deficit hyperactivity disorder, and dipolar disorder.

Any method described herein can be used to ameliorate or improve a symptom of a neurological disease or disorder. Non-limiting examples of symptoms associated with neurological disease or disorder include tremor, gait disorder, maldispositional gait, dementia, excessive swelling (edema), muscle weakness, atrophy in the lower extremity, movement disorder (chorea), muscle rigidity, a slowing of physical movement (bradykinesia), loss of physical movement (akinesia), forgetfulness, cognitive (intellectual) impairment, loss of recognition (agnosia), impaired functions such as decision-making and planning, hemifacial paralysis, sensory deficits, numbness, tingling, painful paresthesias in the extremities, weakness, cranial nerve palsies, difficulty with speech, eye movements, visual field defects, blindness, hemorrhage, exudates, proximal muscle wasting, dyskinesia, abnormality of tonus in limb muscles, decrease in myotony, incoordination, wrong indication in finger-finger test or finger-nose test, dysmetria, Holmes-Stewart phenomenon, incomplete or complete systemic paralysis, optic neuritis, multiple vision, ocular motor disturbance such as nystagmus, spastic paralysis, painful tonic seizure, Lhermitte syndrome, ataxia, mogilalia, vesicorectal disturbance, orthostatic hypotension, decrease in motor function, bed wetting, poor verbalization, poor sleep patterns, sleep disturbance, appetite disturbance, change in weight, psychomotor agitation or retardation, decreased energy, feelings of worthlessness or excessive or inappropriate guilt, difficulty thinking or concentrating, recurrent thoughts of death or suicidal ideation or attempts, fearfulness, anxiety, irritability, brooding or obsessive rumination, excessive concern with physical health, panic attacks, and phobias.

Described herein are tNSCs having certain desirable characteristics; first, the tNSCs are mixed cell populations composed of heterogeneous subtypes with uniformity in phenotypes, stable gene expression and pluripotent characteristics; second, they contain glia progenitor cells and astrocytes which substantially potentiate dopaminergic neurogenesis; third, they possess an intrinsic capacity to 'rescue' dysfunctional dopaminergic neurons and the immune-privileged property; and finally, the neurotrophic effects secreted from different neural precursors on the host tissue would facilitate structural repair.

Provided herein, in some embodiments, are tNSCs having certain desirable characteristics that allow for appropriate manipulation in transplantation therapy: 1) the unique tNSCs are simply and efficiently induced by RA in respect to consistency in quality and abundant cell sources; 2) the grafted tNSCs generate newly dopaminergic neurons in the lesioned nigrostriatal pathway functionally, which can survive for at least 18 weeks postimplantation, 3) the sensorimotor impairments are significantly improved as early as from 3 weeks postimplantation; 4) the tNSCs possess immune privilege, facilitating stem cell therapy; 5) manipulations of the molecular mechanisms in cell proliferation as described herein allows for development of strategies to prevent tumorigenesis after transplantation; 6) the tNSCs are capable of being grown in culture through several cell passages; and 7) the tNSCs are capable of being cultured in media that are free of mouse embryonic feeder cells.

Provided herein, in one embodiment, is a method to treat acute and chronic disease, wherein the method comprises implantation of hTS cell-derived tNSCs. In one embodiment, the tNSCs are implanted into the brain of a patient suffering from a neurological disorder. In another embodiment, the tNSCs are implanted into the striatum of a patient suffering from a neurological disorder.

One aspect described herein a method of treating a neurological disease, wherein the method comprises site-specific integration of tNSCs. In one embodiment, the tNSCs are derived from hTS cells. In another embodiment, the chance of tumor formation is lower as compared to hES cell therapy.

Treatment of Neurodegenerative Diseases by Regeneration of Dopaminergic Neurons

Provided herein are methods for inducing dopaminergic neurons in a mammal wherein neuronal progenitor cells described herein are transplanted as a cell suspension thereby producing a more homogenous reinnervation compared to transplants of tissue chunks. In one embodiment, the induction of dopaminergic neurons as described herein reduces the risk of dyskinesias and increases the chances of clinically beneficial effects. In one embodiment, the mammal is a human. In another embodiment, the mammal is a rat, mouse, pig, dog, monkey, orangutan or ape.

Transplantation of tNSCs induces newly generated dopaminergic neurons in the nigrostriatal pathway and substantially improved the behavioral impairments in parkinsonian rats. These results provide evidence that hTS cells are human pluripotent stem cells that are suitable for use in clinical applications to treat neurodegenerative diseases.

A first experiment was conducted to examine: 1) whether the tNSCs treated with different duration of RA would affect the efficacy in improvement of the behavioral deficits in PD rats and; 2) how long such implanted tNSCs can survive in the brain. Transplantation of the GFP-tagged tNSCs ($1.5 \times 10^6$) into two sites of the lesioned striatum significantly improved the behavioral defects from third week unto 12 weeks by apomorphin-induced rotation assays (FIG. 5a). PD rats received 5-day RA-induced tNSCs improved significantly at the beginning of 6-week postimplantation, however, this effect lost henceforth similar to that control at 12 weeks. The reason can be explained by that most of the neurogenetically fate-restricted GRP (Götz) after induction over 5 days are placed at a ridge in differentiating into undefined trophoblast giant cells. Given the behavioral improvement, the rats were sacrificed at 18th week in order to examine the viability of those GFP-tagged tNSCs. Brain sections revealed abundant newly generated dopaminergic neurons in the nigrostriatal pathway with multiple outgrowths projecting from the cell body, reinnervating the surrounding brain areas immunohistochemically (FIG. 5b). However, no such phenomenon was observed in rats which received 5-day RA-induced tNSCs (FIG. 5c) and the control PD group (FIG. 5d). Immunofluorescence microscopy, at 18th week, demonstrated that the GFP-tagged tNSCs still existed in the lesioned areas, distributing in scattered or patchy patterns at the injection site. Neither teratoma formation was found nor immunosuppression agent used.

Figure 6:
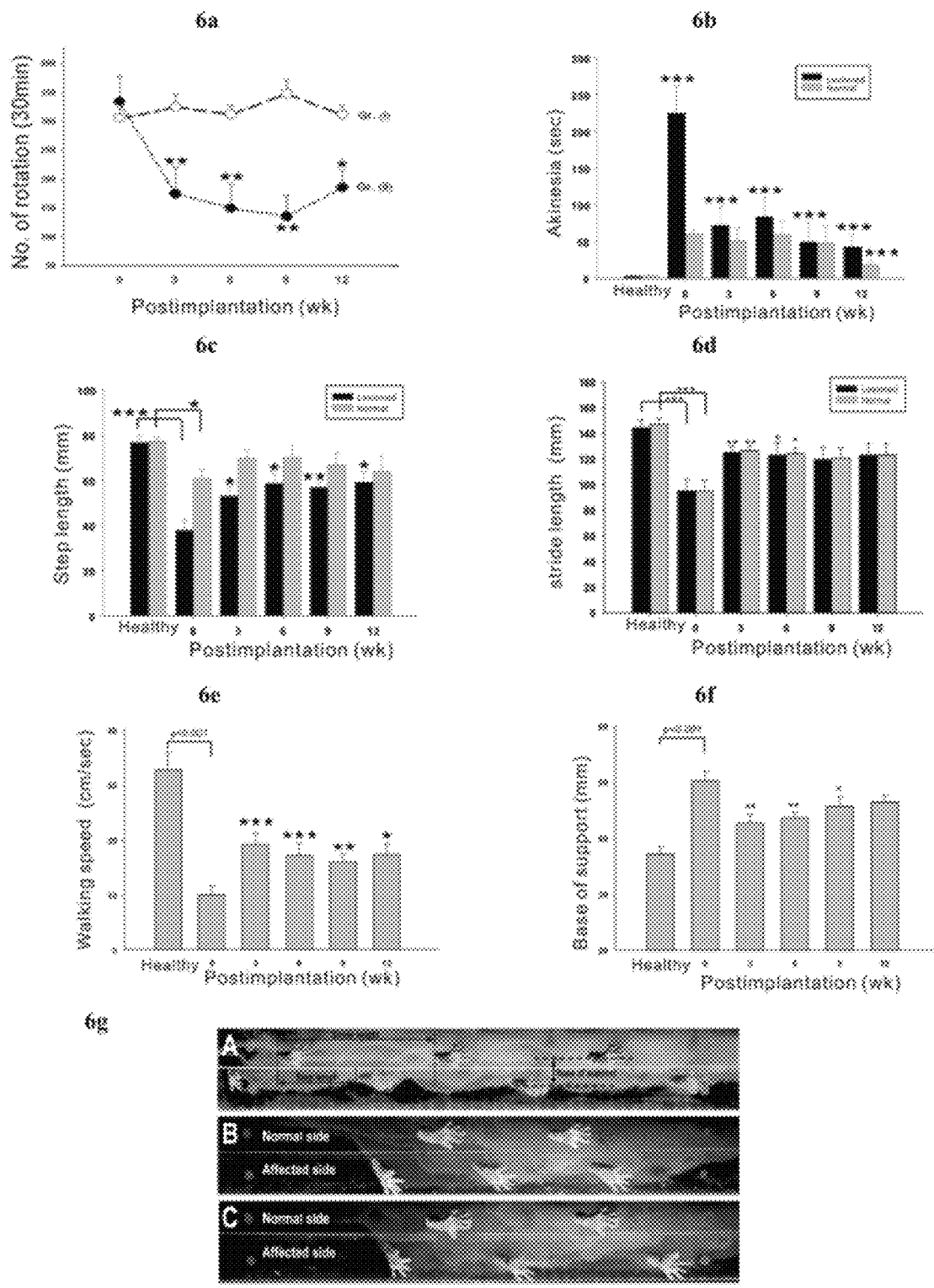
FIG. 6 illustrates the results from transplantation of tNSCs ($1.5\times10^6$) at one injection site into the lesioned striatum of "aged" PD rats (n=16; body weight, 630-490 gm). Behavioral assessments were analyzed every 3 weeks postimplantation. Results showed that there was a significant improvement of behavioral impairments assessed from 3 weeks to 12 weeks postimplanation. Student t test: *p<0.05 as statistic significance. p<0.01 and *p<0.001. (6a) Analysis of apomorphine-induced rotation tests demonstrate aged PD rats that received tNSCs implantation significantly improved the rotation turns from 3 weeks to 12 weeks (group ii, n=8, filled circles) compared to the untreated "aged" PD rats as the control group (group i, n=8, unfilled circles). (6b) Illustrates behavioral assessment results for akinesia (sec). (6c) Illustrates behavioral assessment results for step length (mm). (6d) Illustrates behavioral assessment results for stride length (mm). (6e) Illustrates behavioral assessment results for walking speed (cm/sec). (6f) Illustrates behavioral assessment results for base of support (mm). (6g) Illustrates the gaits analyzed for behavioral assessments: A correlates with normal rats, B correlates with hemiparkinsonian rats prior to cell transplantation, and C correlates with hemiparkinsonian rats after cell transplantation.

To avoid the adverse effects from the dopaminergic overgrowth and uneven and patchy reinnervation, a second experiment was attempted to transplant less tNSCs ($1 \times 10^6$) by injection at one site into the lesioned striatum in "aged" PD rats (n=16; body weight, 630-490 gm). Behavioral assessments were analyzed every 3 weeks postimplantation. Results showed that there was a significant improvement of contralateral rotations from 3-week toward 12-week postimplantation in the apomorphine-induced rotation test (FIG. 6a). To assess the effects of cell therapies in the postural imbalance and gait disorder (PIGD), characterized by akinesia, rigidity and gait and balance impairments, several tests were performed such as walking speed, step length, stride length and base of support. The grasping time of the affected forelimb on the bar was significantly shortened by 3 weeks and continued to improve at the end of 12 weeks in the "bar test" (FIG. 6b), indicating a very quick improvement in the power of seizure in forelimb. Measurements of step length (FIG. 6c), stride length (FIG. 6d), walking speed (FIG. 6e) and base of support (FIG. 6f) showed that transplantation of the tNSCs significantly improved the sensorimotor impairments from early 3-week towards 12-week functionally. In one embodiment, the tNSCs are suitable candidates for stem cell-based therapy in patients with neurodegenerative diseases (e.g., Parkinson's disease) in regenerative medicine. At the end of 12 weeks, rats were sacrificed and brain sections were subjected for tyrosine hydroxylase (TH) immunostaining. The experiments showed regeneration of new dopaminergic neurons appeared in the nigrostriatal pathway (FIG. 19). The newly generated dopamine neurons were assessed by using densitometry, which revealed a 28.2% in recovery. In one embodiment, the tNSCs are an alternative substitute of both hES cells and fetal mesencephalic tissue in the treatment of patients with neurodegenerative diseases.

Provided herein, in one embodiment, is a hTS cell that is a human pluripotent stem cell other than a hES cell but with similar characteristics of pluripotency and self-renewal in early embryogenesis. In vivo, the grafted tNSCs generate newly dopaminergic neurons in the lesioned nigrostriatal pathway functionally, which can survive for at least 18 weeks postimplantation in PD rats. Sensorimotor impairments are significantly improved as early as from 3 weeks postimplantation by a set of behavioral assessments in both young and aged PD rats. Transplantation of the hTS cell-derived NSCs into the neurotoxin-denervated striatum of brain enables regeneration of the lost dopaminergic neurons and improves the major behavioral deficits in rats with PD.

In one embodiment, DA neurons in the nigrostriatal pathway are regenerated. In another embodiment, the implanted tNSCs increase glial cells in the striatum. In another embodiment, RA induces the expression of GRAD and GFAP-positive progenitor cells, giving rise to neurons and oligodendrocytes throughout the CNS.

Treatment of Alzheimer's Disease

Provided herein are methods for treating Alzheimer's Disease, wherein the method comprises transplanting neuronal progenitor cells into the brain of a mammal. In one embodiment, the mammal is a human. In another embodiment, the human is a patient diagnosed with Alzheimer's Disease or at risk of developing Alzheimer's Disease, e.g., a person with a family history of the disease or who has been identified as having a risk factor for the disease. In another embodiment, the mammal is a pig, dog, monkey, orangutan or ape. In another embodiment, the mammal is a mouse. In another embodiment, the mammal is a rat. In another embodiment, the rat or mouse displays symptoms of Alzheimer's Disease. In one embodiment, the neuronal progenitor cells are transplanted into a non-human animal model for the disease (e.g., a mouse model in which AD7c-

NTP is overexpressed, an Alzheimer's Disease rat model, a transgenic mouse model, etc.)

In one embodiment, hTS cells are treated with an inducing agent to provide a neuronal cell population with a biomarker signature. In a specific embodiment, the inducing agent is RA. In one embodiment, the molecular mechanisms or signaling pathways are modulated to maintain pluripotency. In another embodiment, the molecular mechanisms or signaling pathways are modulated to prevent tumorigenesis after transplantation.

In another embodiment, the tNSCs are grafted or inserted into the brain of the mammal. In one embodiment, the neuronal progenitor cells are transplanted as a cell suspension thereby producing a more homogenous reinnervation. In another embodiment, the neuronal progenitor cells are injected into the brain of said mammal. In another embodiment, the tNSCs derived from hTS cells are inserted into the subventricular zone of the brain. In one embodiment the mammal is a human.

In one embodiment, the induction of neurons as described herein reduces the risk of tumorigenesis and increases the chances of clinically beneficial effects. In another embodiment, the recipient of the tNSCs shows an improvement in symptoms associated with Alzheimer's disease. In another embodiment, the connections between neurons in the brain are increased and strengthened.

Treatment of Schizophrenia

Provided herein are methods for treating schizophrenia, wherein the method comprises transplanting neuronal progenitor cells into the brain of a mammal. In one embodiment, the mammal is a human. In another embodiment, the human is a patient diagnosed with schizophrenia or at risk of developing schizophrenia, e.g., a person with a family history of the disease or who has been identified as having a risk factor for the disease. In another embodiment, the mammal is a mouse. In another embodiment, the mammal is a rat. In another embodiment, the mammal is a pig, dog, monkey, orangutan or ape. In another embodiment, the rat or mouse displays symptoms of schizophrenia.

In one embodiment, the neuronal progenitor cells are transplanted into a non-human animal model for the disease (e.g., a schizophrenia rat model, a transgenic mouse model, etc.) In one embodiment, model mouse has an altered normal physiological regulation of the neuronal system. In another embodiment, the model animal or tissues can be utilized for screening of potential therapeutic agents and/or therapeutic regimens that act at the intracellular level.

In one embodiment, hTS cells are treated with an inducing agent to provide a neuronal cell population with a biomarker signature. In a specific embodiment, the inducing agent is RA. In one embodiment, the molecular mechanisms or signaling pathways are modulated to maintain pluripotency. In another embodiment, the molecular mechanisms or signaling pathways are modulated to prevent tumorigenesis after transplantation.

In another embodiment, the tNSCs are grafted or inserted into the brain of the mammal. In one embodiment, the neuronal progenitor cells are transplanted as a cell suspension thereby producing a more homogenous reinnervation. In another embodiment, the neuronal progenitor cells are injected into the brain of said mammal.

In one embodiment, the induction of neurons as described herein reduces the risk of tumorigenesis and increases the chances of clinically beneficial effects. In another embodiment, the recipient of the tNSCs shows an improvement in symptoms associated with schizophrenia.

Dosing and Administration

Modes of administration of an isolated neural stem cell preparation described herein include, but are not limited to, systemic intravenous injection and injection directly to the intended site of activity. The preparation can be administered by any convenient route, for example, by infusion or bolus injection, and can be administered together with other biologically active agents. In one embodiment, administration is systemic localized administration.

In one embodiment, a neural stem cell preparation or composition is formulated as a pharmaceutical composition adapted for intravenous administration to mammal, including human beings. In some embodiments, compositions for intravenous administration are solutions in sterile isotonic aqueous buffer. Where necessary, the composition also includes a local anesthetic to ameliorate any pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients are mixed prior to administration.

In one embodiment, suitable pharmaceutical compositions comprise a therapeutically effective amount of the progenitor stem cells and a pharmaceutically acceptable carrier or excipient. Such a carrier includes, but is not limited to, saline, buffered saline, dextrose, water, and combinations thereof.

In one embodiment, the isolated tNSCs described herein are delivered to a targeted site (e.g., the brain, the spinal cord or any other site of nerve injury and/or degeneration) by a delivery system suitable for targeting cells to a particular tissue. For example, the cells are encapsulated in a delivery vehicle that allows for the slow release of the cell(s) at the targeted site. The delivery vehicle is modified such that it is specifically targeted to a particular tissue. The surface of the targeted delivery system is modified in a variety of ways. In the case of a liposomal-targeted delivery system, lipid groups are incorporated into the lipid bilayer of the liposome in order to maintain the targeting ligand in stable association with the liposomal bilayer.

In another example, a colloidal dispersion system is used. Colloidal dispersion systems include macromolecule complexes, nanocapsules, microspheres, beads, and lipid-based systems, including oil-in-water emulsions, micelles, mixed micelles, and liposomes.

The administration of tNSCs described herein is optionally tailored to an individual, by: (1) increasing or decreasing the amount cells injected; (2) varying the number of injections; (3) varying the method of delivery of the cells; or (4) varying the source of cells, e.g., by genetically engineering cells, or from in vitro cell culture.

The tNSC preparation is used in an amount effective to promote engraftment of cells in the recipient. At the physician's discretion, the administration is adjusted to meet optimal efficacy and pharmacological dosing.

Methods of Screening

Provided herein are methods of screening a compound for use in treatment or prevention of a disease. In one embodiment, the method comprises contacting an isolated human trophoblastic stem cell with said compound. In another embodiment, the method comprises contacting an isolated neural stem cell with said compound. In another embodiment, the method further comprises detecting a change in the activity of at least one gene, transcript or protein in said human trophoblastic stem cell. In another embodiment, the method further comprises detecting a change in the level of at least one transcript or protein in said human trophoblastic stem cell. In another embodiment, the method comprises detecting a change in the activity of at least one gene, transcript or protein in said neural stem cell.

One embodiment provided herein describes a method of screening a compound for ability to induce changes in a cell comprising. In one embodiment, the method comprises contacting an isolated human trophoblastic stem cell with said compound. In another embodiment, the method comprises contacting an isolated neural progenitor stem cell with said compound. In another embodiment, the method further comprises detecting an induction of differentiation of said human trophoblastic stem cell. In another embodiment, the method further comprises detecting an induction of differentiation of said neural stem cell.

Also provided herein a method of screening a compound for cellular toxicity or modulation of the cell, the method comprising contacting a differentiated cell of this invention with the compound. In another embodiment, the method further comprises determining any phenotypic or metabolic changes in the cell that result from contact with the compound, and correlating the change with cellular toxicity or any other change in cell function or biochemistry. In another embodiment, screening of pharmaceuticals, toxins, or potential modulators of differentiation is facilitated. These substances (e.g., pharmaceuticals, toxins, or potential modulators) can be added to the culture medium.

One embodiment provided herein described a method of screening proliferation factors, differentiation factors, and pharmaceuticals. In one embodiment, human trophoblast stem cell or neural stem cell are used to screen for factors (such as small molecule drugs, peptides, polynucleotides, and the like) or conditions (such as culture conditions or manipulation) that affect the characteristics of human trophoblast stem cell or neural stem cell in culture. In one embodiment, this system has the advantage of not being complicated by a secondary effect caused by perturbation of the feeder cells by the test compound. In another embodiment, growth affecting substances are tested. In another embodiment, the conditioned medium is withdrawn from the culture and a simpler medium is substituted. In another embodiment, different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cell according to the test protocol, and then determining whether the treated cell develops functional or phenotypic characteristics of a differentiated cell of a particular lineage.

In one embodiment, the human trophoblast stem cell or neural stem cell are used to screen potential modulators of cellular differentiation. In one embodiment, the cellular differentiation is neural differentiation. For example, in one assay for screening modulators of cellular differentiation, the human trophoblast stem cell or neural stem cell can be cultured under serum free, low density conditions in the presence or absence of LIF, in the present of the modulator, and in the present or absence of RA, as the situation requires, and the effect on differentiation can be detected. In another embodiment, the screening methods described herein can be used to study conditions associated with cellular development and screen for potential therapeutic or corrective drugs or modulators of the condition. For example, in one embodiment, the development of the normal human trophoblast stem cell or neural stem cell is compared with the development with cells having the condition.

In one embodiment, gene and protein expression can be compared between different cell populations obtained from human trophoblast stem cell or neural stem cell, and used to identify and characterize factors upregulated or downregulated in the course of differentiation, and produce nucleotide copies of the affected genes.

In one embodiment, feeder-free human trophoblast stem cell or neural stem cell cultures can also be used for the testing of pharmaceutical compounds in drug research. Assessment of the activity of candidate pharmaceutical compounds generally involves combining the differentiated cells of this invention with the candidate compound, determining any resulting change, and then correlating the effect of the compound with the observed change. In another embodiment, the screening is done, for example, either because the compound is designed to have a pharmacological effect on certain cell types, or because a compound designed to have effects elsewhere have unintended side effects. In another embodiment, two or more drugs are be tested in combination (by combining with the cells either simultaneously or sequentially), to detect possible drug-drug interaction effects. In another embodiment, compounds are screened initially for potential toxicity. In another embodiment, cytotoxicity is be determined by the effect on cell viability, survival, morphology, on the expression or release of certain markers, receptors or enzymes, on DNA synthesis or repair.

The terms "treating," "treatment," and the like are used herein to mean obtaining a desired pharmacologic and/or physiologic effect. In some embodiments, an individual (e.g., an individual suspected to be suffering from and/or genetically pre-disposed to a neurodegenerative disorder is treated prophylactically with a preparation of tNSCs described herein and such prophylactic treatment completely or partially prevents a neurodegenerative disorder or sign or symptom thereof. In some embodiments, an individual is treated therapeutically (e.g., when an is suffering from a neurodegenerative disorder), such therapeutic treatment causes a partial or complete cure for a disorder and/or reverses an adverse effect attributable to the disorder and/or stabilizes the disorder and/or delays progression of the disorder and/or causes regression of the disorder.

Administration (e.g., transplantation) of tNSCs to the area in need of treatment is achieved by, for example and not by way of limitation, local infusion during surgery, by injection, by means of a catheter, or by means of an implant, said implant being of a porous, non-porous, or gelatinous material, including membranes, such as sialastic membranes, or fibers.

"Transplanting" a composition into a mammal refers to introducing the composition into the body of the mammal by any method established in the art. The composition being introduced is the "transplant", and the mammal is the "recipient". The transplant and the recipient can be syngeneic, allogeneic or xenogeneic. Further, the transplantation can be an autologous transplantation.

An "effective amount" is an amount of a therapeutic agent sufficient to achieve the intended purpose. For example, an effective amount of a factor to increase the number of hTS cells or tNSCs is an amount sufficient, in vivo or in vitro, as the case can be, to result in an increase in neural stem cell number. An effective amount of a composition to treat or ameliorate a neurodegenerative disease or condition is an amount of the composition sufficient to reduce or remove the symptoms of the neurodegenerative disease or condition.

The effective amount of a given therapeutic agent will vary with factors such as the nature of the agent, the route of administration, the size and species of the animal to receive the therapeutic agent, and the purpose of the administration.

Further provided herein in one embodiment are genetically modified tNSCs. Manipulations modify various properties of the cell, e.g., render it more adapted or resistant to certain environmental conditions, and/or induce a production of one or more certain substances therefrom, which substances can, e.g., improve the viability of the cell. Such genetic alterations can be performed in order to make the cell more suitable for use in transplantation, for example, in order to avoid rejection thereof from the recipient (for reviews of gene therapy procedures, see Anderson, Science, 256:808; Mulligan, Science, 926; Miller, Nature, 357:455; Van Brunt, Biotechnology, 6(10):1149; and Yu et al., Gene Therapy, 1:13).

A "vector" refers to a recombinant DNA or RNA construct, such as a plasmid, a phage, recombinant virus, or other vector that, upon introduction into an appropriate host cell, results in a modification of a progenitor cell described herein. Appropriate expression vectors are well known to those with ordinary skill in the art and include those that are replicable in eukaryotic and/or prokaryotic cells and those that remain episomal or those that integrate into the host cell genome.

Construction of vectors is achieved using techniques described in, for example, as described in Sambrook et al., 1989. In one embodiment isolated plasmids or DNA fragments are cleaved, tailored, and religated in the form desired to generate the plasmids. If desired, analysis to confirm correct sequences in the constructed plasmids is performed using any suitable method. Suitable methods for constructing expression vectors, preparing in vitro transcripts, introducing DNA into host cells, and performing analyses for assessing gene expression and function are known. Gene presence, amplification, and/or expression are measured in a sample directly, for example, by conventional Southern blotting, Northern blotting to quantitate the transcription of mRNA, dot blotting (DNA or RNA analysis), or in situ hybridization, using an appropriately labeled probe which can be based on a sequence provided herein.

As used herein, terms such as "transfection", "transformation", and the like are intended to indicate the transfer of nucleic acid to a cell or organism in functional form. Such terms include various means of transferring nucleic acids to cells, including transfection with CaP04, electroporation, viral transduction, lipofection, delivery using liposomes, and/or other delivery vehicles.

Cells are sorted by affinity techniques or by cell sorting (such as fluorescence-activated cell sorting) where they are labeled with a suitable label, such as a fluorophore conjugated to or part of, for example, an antisense nucleic acid molecule or an immunoglobulin, or an intrinsically fluorescent protein, such as green fluorescent protein (GFP) or variants thereof. As used herein, "sorting" refers to the at least partial physical separation of a first cell type from a second.

As used herein, the term "about" means±15%. For example, the term "about 10" includes 8.5 to 11.5.

EXAMPLES

Materials

Antibodies.

For immunoblot and immunocytochemistry: primary antibodies: SSEA-1, -2, -3, CD90 and nestin (Chemicon). Neurofilament, and GFAP (BioGenex). Nanog, Oct4, Cdx2 and Sox2 (BD Biosciences, San Jose, Calif., USA). $G_{\alpha q/11}$ (C-19, sc-392), Gβ (T-20, sc-378), RXRα, RARβ, c-Src, pStat3, Stat3, PP1 analog and β-actin (Santa Cruz Biotechnology, Santa Cruz, Calif., USA), TH (Sigma-Aldrich St. Louis, Mo. and Temcoula, Calif.) and serotonin (Sigma-Aldrich St. Louis, Mo.).

Secondary Antibodies:

siRNAs: Nanog siRNA and Cdx2 siRNA (Sigma-Aldrich St. Louis, Mo.).

For flow cytometry Primary antibodies: HLA-ABC, CD9, CD14, CD34, CD45, CD73, CD90, CK7, vimentin, 6-integrin, E-cadherin, L-selectin, Nanog, Oct4, Cdx2 and Sox2 were purchased from BD Biosciences, San Jose, Calif., USA; HLA-DR, CD33, CD44 and CD105 from eBioscience, San Diego, Calif., USA; CD133 from Miltenyi Biotec, Germany.

For TH-2 and serotonin immunostainings, cells were incubated in 0.1M PBS at 4° C. overnight after washing with PBS. After incubation with blocking solution (50 ml 0.1 M PBS, 0.05 g sodium azide, 1% horse serum and 10% Triton X-100) for 1 h at room temperature, the cells were washed again. Cells were incubated with primary antibody, i.e., TH-2 (1:200, Sigma-Aldrich, St. Louis, Mo.) and serotonin (1:100, Sigma-Aldrich, St. Louis, Mo.) for 2 h and washed with PBS. By incubation with anti-mouse IgG with FITC or PE (Sigma-Aldrich, St. Louis, Mo.) for 1 h, cells were thoroughly washed with PBS and subjected to immunofluorescence assays.

Example 1

Isolation, Differentiation and Cell Culture

Embryonic chorionic villious were obtained from the fallopian tubes of early ectopic pregnancy (gestational age: 6-8 weeks) in women via laparoscopic surgery, approved by the Institutional Review Board on Human Subjects Research and Ethics Committees. Tissues were minced in serum-free α-MEM (Sigma-Aldrich, St. Louis, Mo.) and trypsinized with 0.025% trypsin/EDTA (Sigma-Aldrich, St. Louis, Mo.) for 15 min and this digestion was halted by adding α-MEM containing 10% FBS. This procedure was repeated several times. After centrifugation, cells were collected and cultured with α-MEM containing 20% FBS (JRH, Biosciences, San Jose, Calif.) and 1% penicillin-streptomycin in 5% $CO_2$ at 37° C. The hCG expression in the medium became undetectable after two passages of culture measured by a commercial kit (Dako, Carpinteria, Calif.).

Cell Differentiation.

hTS cells were cultured in conditioned α-MEM containing 20% FBS, 1% penicillin-streptomycin, and 10 μg/ml bFGF (CytoLab Ltd, Rehovot, Israel) at 37° C. in 5% $CO_2$. The medium was replaced every 3 days. After five passages, differentiation into various specialized phenotypes was initiated by using published protocols with modifications. For cell culture in Transwell plate (Corning, New York, N.Y.), the upper chamber was coated with 500 μl of collagen gel containing PureCol (Inamed Biomaterials, Fremont, Calif.) and conditioned L-DMEM (Gibco, Grand Island, N.Y.) at a 4:1 ratio (adjusted to pH 7.4 using 1 M NaHCO$_3$). Cells ($4\times10^5$) were cultured in conditioned L-DMEM (1 ml) on the upper chamber. The lower chamber contained conditioned H-DMEM (3 ml). Preliminary experiments showed that the glucose levels in both chambers could reach an equilibrium status in 4 hr.

Cell Differentiation of Subphenotypes.

Cells were cultured in conditioned α-MEM containing 20% FBS, 1% penicillin-streptomycin, and 10 µg/ml bFGF (CytoLab Ltd, Rehovot, Israel) at 37° C. in 5% CO$_2$. The medium was refreshed every 3 days in general. After 5 passages of culture, cell differentiations into a variety of specific cell phenotypes were performed by various strategies as shown in the Table in FIG. 12. For osteogenic differentiation, cytochemical mineral matrix was analyzed using an Alizarin red S assay (Sigma-Aldrich, St. Louis, Mo.) to detect the calcium mineral content. To identify the calcium deposits, cells were fixed and incubated with 2% silver nitrate solution (w/v) for 10 min in dark followed by thorough wash with de-ionized water and exposed under bright light for 15 min. Cells were treated with von Kossa staining to detect alkaline phosphatase activity using a commercial kit (Sigma-Aldrich, St. Louis, Mo.). Chondrogenic differentiation was confirmed using Alcian blue staining (Sigma-Aldrich, St. Louis, Mo.) at an acidic pH level. For myogenic differentiation, cells were incubated with 3% hydrogen peroxide in phosphate buffer saline (PBS) for 10 min to quench the endogenous peroxidase enzyme activity. The non-specific sites were blocked by PBS containing 10% human serum and 0.1% Triton X-100 for 60 min and washed by blocking buffer for 5 min. Cells were incubated in blocking buffer containing skeletal muscle myosin heavy chain-specific monoclonal antibody (Vector Laboratories, Burlingame, Calif.) for 1 h, and stained using VectaStain ABC kit (Vector Laboratories). For adipogenic differentiation, cells were induced by conditioned media and fixed for 60 min in 4% paraformaldehyde containing 1% calcium and washed with 70% ethanol. After exposure to 2% Oil red 0 reagent (Sigma-Aldrich, St. Louis, Mo.) for 5 min, the excessive staining was removed by 70% ethanol followed by water rinses. Oil red O stain was applied as an indicator of intracellular lipid accumulation. Neural stem cells were induced by 10 µM all-trans retinoic acid (Sigma-Aldrich, St. Louis, Mo.) in ethanol.

Example 2

Plasmid Transfection

For plasmid transfection, hTS cells were induced by all-trans retinoic acid (10 µM) (Sigma-Aldrich, St. Louis, Mo.) overnight followed by co-transfection in a DNA mixture of F1B-GFP as described previously (Myers). Briefly, the DNA mixture was added slowly into DOTAP (100 µl) solution containing DOTAP (30 µl) liposomal transfection reagent (Roche Applied Science, Indianapolis, Ind.) and 70 µl HBSS buffer containing NaCl (867 g in 80 ml H$_2$O) plus 2 ml HEPES solution (1 M, pH 7.4, Gibco) at 4° C. for 15 min. After wash by PBS, cells were mixed well with the DNA mixture. After incubation overnight, stable cells lines were obtained by G418 selection (400 µg/ml, Roche Applied Science) through culture for 2-3 weeks until the formation of colonies. The G418-resistant cells were pooled and lysed and analyzed by Western blotting using monoclonal anti-GFP antibody (Stratagene, La Jolla, Calif.) to quantify the percentage of transfectants that expressed GFP. By subcultures, the transfected hTS cells were fixed with methanol (10 min) to detect the expression of GFP by immunofluorescence. The transfection rate yielded over 95% of efficacy.

Example 3

RT-PCR and Quantitative PCR (qPCR)

For RT-PCR, total RNA from $10^5$-$10^6$ cells was extracted by using TRIZOL reagent (Invitrogen) and mRNA expression by using a Ready-To-Go RT-PCR Beads kit (Amersham Biosciences, Buckinghamshire, UK). Briefly, the reaction products were resolved on 1.5% agarose gel and visualized with ethidium bromide. β-actin or β-2 microglobulin was used as a positive control. All experiments were performed in triplicate. For qPCR, gene expression was measured with the iQ5 Real-Time PCR Detection System (Bio-Rad Laboratories) and analyzed with Bio-Rad iQ5 Optical System Software, version 2.0 (Bio-Rad Laboratories). Relative mRNA levels were calculated using the comparative Ct method (Bio-Rad, instruction manual) and presented as a ratio to biological controls. All primer pairs were confirmed to approximately double the amount of product within one cycle and to yield a single product of the predicted size.

Example 4

Western Blots

Cells were seeded into 10 cm dish with the serum-free medium for overnight and treated with or without RA (10 µM) for various time intervals as indicated. After stimulation, cells were washed twice with ice-cold PBS and lysed by RIPA lysis buffer (Minipore). Protein concentration was determined by BCA protein assay kit (Thermo). Equal amounts of protein (30 µg) were resolved by 8% SDS-PAGE, transferred onto PVDF membrane and blocked with 5% non-fat dry milk for 1 h at room temperature. After blocking, the membrane was incubated with primary antibodies for 4 h at 4° C. Cells were washed three times with PBST and then incubated with HRP conjugated secondary antibodies for 1 h at room temperature. After washing six times with PBST buffer, the membrane was incubated with a chemiluminescent substrate (GE Healthcare) for 1 min. Specific bands were visualized using an enhanced chemiluminescence kit (ECL) (Amersham).

Example 5

Southern Blots

The telomere length of hTS cell was measured at passages 3 and 7 by southern immunoblot analysis as described previously (Tsai). Briefly, the fragments were transferred to Hybond N+ nylon membranes (Amersham Biosciences) and hybridized at 65° C. to a probe of TTAGGG repeats labeled with α-$^{32}$P-dCTP using Ready-To-Go labeling beads (Amersham Biosciences). Terminal restriction fragments were visualized by hybridization with labeled oligonucleotides complementary to the telomeric repeat sequence. The size distribution of the TRFs was compared with a DNA length standard.

Example 6

Terminal Restriction Fragment (TRF) Southern Blot

Since a cell initiates its cancerous change, its telomeres would become very short. The tolomere length was measured at 3rd and 7th passages in culture of hTS cells. Briefly, the fragments were transferred to Hybond-N+ nylon membranes (Amersham Biosciences) and hybridized at 65° C. to a probe of TTAGGG repeats labeled with α-[$^{32}$P]-dCTP by using Ready-To-Go DNA Labeling Beads (Amersham Biosciences). Terminal restriction fragments were visualized by hybridization with labeled oligonucleotides complementary to the telomeric repeat sequence. The size distribution of the terminal restriction fragments was compared with a DNA length standard. For electron microscopy, the hTS cell-derived grape-like cell mass was examined by transmission electron microscopy (JEM-2000 EXII, JEOL, Tokyo, Japan) to identify the infrastructure of the cell.

The differential gene expressions of Oct4, Sox2, NANOG, fgfr2, FGF4, BMP4, Cdx2, and endogenous control β-actin (ACTB) were measured in the hTS and the hTS cells treated by 500 units LIF (Chemicon, Temecula, Calif.) by IQ5 Real-time PCR detection system (Bio-Rad Laboratories) that using fluorescein as an internal passive reference dye for normalization of well-to-well optical variation. PCR amplifications were carried out in a total volume of 25 µl, containing 12.5 µl of 2×SYBR Green supermix (Bio-Rad), 0.5 µl of 10 µM of each primer and 0.5 µl of cDNA samples and mixed with sterile water. The reaction was initiated at 95° C., 3 minutes, followed by 60 three-step amplification cycles consisting of 30 s denaturation at 95° C., 30 s annealing at 60° C., 15 s extension at 72° C. At final dissociation stage, it was run to generate a melting curve for verification of amplification product specificity. Real-time qPCR was monitored and analyzed by the Bio-Rad IQ5 optical system software version 2.0 (Bio-Rad). Relative mRNA levels were calculated using the comparative Ct method (Bio-Rad instruction manual) and presented with ratio to biological controls. ACTB transcript levels were confirmed to correlate well with total RNA amounts and therefore used for normalization throughout. All primer pairs used were confirmed to approximately double the amount of product within one cycle and to yield a single product of the predicted size. Primer sequences of Oct4, Sox2, NANOG, fgfr2, FGF4, BMP4, Cdx2, and endogenous control β-actin (ACTB) are shown in Supplemental Data Table 3.

```
                                        (SEQ ID NO: 1)
OCT4-F:  CCATCTGCCGCTTTGAGG;

(SEQ ID NO: 2)
OCT4-R:  ACGAGGGTTTCTGCTTTGC;

(SEQ ID NO: 3)
ACTB-F:  GATCGGCGGCTCCATCCTG;

(SEQ ID NO: 4)
ACTB-R:  GACTCGTCATACTCCTGCTTGC;

(SEQ ID NO: 5)
CDX2-F;  GTGTACACGGACCACCAGCG (SEQ ID NO: 6)
CDX2-R;  GGTGGCTGCTGCTGCTGTTG (SEQ ID NO: 7)
MIG7-F;  TCCACTACCAAGAGACAGGCTT (SEQ ID NO: 8)
MIG7-R;  TCAAGCTGTGTTGCACCCAA (SEQ ID NO: 9)
IPF-1-F; GGAGGAGAACAAGCGGACGC (SEQ ID NO: 10)
IPF-1-R; CGCGCTTCTTGTCCTCCTCC
```

TABLE 1

Various PCR primers (SEQ ID NOS 11-48, respectively, in order of appearance) used for gene expression

| Gene | Sequence (5'→3') | Product size (bp) | Anneal temp ° C. |
|---|---|---|---|
| Osteopontin | Forward:: CTAGGCATCACCTGTGCCATACC<br>Reverse: CAGTGACCAGTTCATCAGATTCATC | 330 | 55.7 |
| Osteocalcin | Forward: CGCAGCCACCGAGACACCAT<br>Reverse: GGGCAAGGGCAAGGGGAAGA | 405 | 66 |
| Perlecan (PRLN) | Forward: CATAGAGACCGTCACAGCAAG<br>Reverse: ATGAACACCACACTGACAACC | 300 | 50 |
| Collagen typeII | Forward: ACGGCGAGAAGGGAGAAGTTG<br>Reverse: GGGGGTCCAGGGTTGCCATTG | 352 | 60.1 |
| Myogenin | Forward: AGCGCCCCCTCGTGTATG<br>Reverse: TGTCCCCGGCAACTTCAGC | 365 | 61 |
| MyoD1 | Forward: CGGCGGCGGAACTGCTACGAA<br>Reverse: GGGGCGGGGCGGAAACTT | 452 | 65.8 |
| PPARγ-2 | Forward: GCTGTTATGGGTGAAACTCTG<br>Reverse: ATAAGGTGGAGATGCAGGCTC | 352 | 50.7 |
| Adipsin | Forward: GGTCACCCAAGCAACAAAGT<br>Reverse: CCTCCTGCGTTCAAGTCATC | 269 | 61 |
| β2-microglobulin | Forward: CTCGCGCTACTCTCTCTCTTTCTGG<br>Reverse: GCTTACATGTCTCGATCCCACTTAA | 335 | 57.3 |

TABLE 1-continued

Various PCR primers (SEQ ID NOS 11-48, respectively, in order of appearance) used for gene expression

| Gene | Sequence (5'→3') | Product size (bp) | Anneal temp ° C. |
|---|---|---|---|
| β-actin | Forward: GTGGGGCGCCCCAGGCACCA<br>Reverse: CTCCTTAATGTCACGCACGATTTC | 539 | 55.5 |
| Oct4 | Forward: GGAAAGGCTTCCCCCTCAGGGAAAGG<br>Reverse: AAGAACATGTGTAAGCTGCGGCCC | 454 | 64 |
| Cdx2-exon 2 | Forward: GTGTACACGGACCACCAGCG<br>Reverse: GGTGGCTGCTGCTGCTGTTG | 199 | 60 |
| Cdx2-exon 1 | Forward: AGCCAAGTGAAAACCAGGAC<br>Reverse: TTTCCTCTCCTTTGCTCTGC | 563 | 60 |
| Nanog | Forward: CTCAGCCTCCAGCAGATGC<br>Reverse: AGGCATCCCTGGTGGTAGG | 200 | 60 |
| Eomeso | Forward: GGCCACTGCGCGCTACTCC<br>Reverse: GGCTCCTGGGCCGAACTGC | 251 | 65 |
| FGF4 | Forward: CCTGGTGGCGCTCTCGTTG<br>Reverse: GCAGGCTGTCGCGGGTGTC | 199 | 60 |
| fgfr-2 | Forward: CACCGTGGCCGTGAAGATG<br>Reverse: GGGCTCGGAGGTATTCTCG | 199 | 61 |
| BMP4 | Forward: CGCTGGACCCGGGAGAAGC<br>Reverse: CTCCGGCGTCGGGTCAAGG | 200 | 63 |
| LIF | Forward: CGTGTACCTTGGCACCTCC<br>Reverse: CCTTACCCGAGGTGTCAGG | 199 | 60 |

| | CT | Std | ΔCT | qPCR ratio |
|---|---|---|---|---|
| T3ES ACTB | 22.85 | 0.26 | | |
| hTS ACTB | 27.18 | 0.10 | | |
| PL ACTB | 23.82 | 0.09 | | |
| hTS-2 ACTB | 19.44 | 0.24 | | |
| T3ES OCT4 | 29.22 | 1.16 | −6.37 | 1.00 |
| hTS OCT4 | 38.16 | 0.90 | −10.98 | 0.04 |
| PL OCT4 | 42.67 | 0.48 | −18.85 | 0.01 |
| hTS-2 OCT4 | 41.08 | 0.20 | −21.64 | 0.01 |
| T3ES CDX2 | 35.36 | 0.59 | −12.51 | 1.00 |
| hTS CDX2 | 32.53 | 0.41 | −5.35 | 143.01 |
| PL CDX2 | 39.32 | 0.52 | −15.50 | 0.13 |
| hTS-2 CDX2 | 40.64 | 0.86 | −21.20 | 0.01 |
| T3ES MIG7 | 38.35 | 0.33 | −15.50 | 1.00 |
| hTS MIG7 | 39.87 | 0.40 | −12.69 | 7.01 |
| PL MIG7 | 35.98 | 0.16 | −12.16 | 10.13 |
| hTS-2 MIG7 | 41.22 | 0.20 | −21.78 | 0.01 |
| T3ES IPF-1 | 30.74 | 0.39 | −7.89 | 1.00 |
| hTS IPF-1 | 30.55 | 0.48 | −3.37 | 22.94 |
| PL IPF-1 | 30.88 | 0.19 | −7.06 | 1.78 |
| hTS-2 IPF-1 | 30.78 | 0.12 | −11.34 | 0.09 |

Example 7

Immunocytochemistry

Cultures were fixed with 4% paraformaldehyde for 30 min at room temperature and then washed three times with PBS. LSAB kit (Dako, Calif.) was used for immunocytochemical staining as manufacturer's recommendations. For SSEA-1 and -4 stainings, cells were rinsed with tris-phosphate buffered saline (TBS) and washed with $H_2O_2$ for 10 min. After blocking the reaction with goat serum (1:200, Dako) for 30 min. Cells then were incubated with primary antibody overnight. After washing the cells with TBS and treated with streptavidin for 20 min, cells were stained by biotin (20 min), washed again, and treated with 3,3' diaminobenzidine tetrachloride (Boehringer-Mannheim, Mannheim, Germany) for 10 min. Finally, the cells were counterstained with hematoxylin stain. For SSEA-3 staining, similar procedures were followed except that the retrieved antigen added, which was obtained using a high-pressure cooker in citrate buffer for 15 min, before washing with $H_2O_2$. Finally, cells were thoroughly washed with PBS and subjected to immunofluorescence assays.

Example 8

Immunoprecipitation (IP)

Cells were serum-deprived for overnight and treated with RA (10 μM) for 30 min. After pre-clearing with protein G-agarose (Minipore) for 30 min, specific antibodies or IgG were added and incubated overnight. By incubation with protein G-agarose for 2 h, the beads were washed three times with RIPA lysis buffer, boiled in buffer, resolved by 8% SDS-PAGE and immunoblot analysis for various targets as indicated.

Example 9

Flow Cytometry

Cells ($5 \times 10^6$ cells/ml) were incubated with a variety of primary antibodies for 30 min and then incubated with the appropriate fluorescein isothiocyanate (FITC)-, phycoerythrin (PE)- or Rho-conjugated secondary antibody (Jackson ImmunoResearch, West Grove, Pa.) at adjusted dilution for 1 h at 4° C. After thorough washing, cells were re-suspended in PBS (1 ml) and subjected to flow cytometry (FACScan, BD Biosciences, San Jose, Calif.). The data were analyzed with Cell-Quest software (BD Biosciences).

Example 10

Microarrays hTS cells were treated by with or without RA (10 µM) for one- and 5-day each. Total RNAs were extracted using TRIzol reagent and subjected for Affymetrix microarray using Affymetrix Human Genome U133 plus 2.0 GeneChip according to the manufacturer's proticole (Santa Clara, Calif., http://www.affymetrix.com) performed at Genomic Medicine Center of National Taiwan University College of Medicine, Taipei, Taiwan)

Example 11

Double Immunogold Electron Transmission Microscopy (IEM)

Cells, with or without treatment of RA (10 µM), were examined as described previously (Tsai et al). Briefly, the fixed ultrathin sections were pretreated with an aqueous solution of 5% sodium metaperiodate (10 min) and washed with distilled water. Grids incubated with an aliquot of IgG antibody against RXRα (1:50) or Gαq/$_{11}$ (C-19; sc-392; 1:50) and followed by probing with a secondary anti-mouse 6 nm gold particles (1:10; AB Chem, Dorval, Canada) or anti-rabbit IgG 20 nm gold particles (1:10; BB International, UK). Grids were washed with PBS between incubation steps and sections blocked by placing the grids on a drop of PBS with 1% ovalbumin (15 min). After IgG gold, the grids were jet-washed with PBS followed by distilled water. All steps were carried out at room temperature. Sections were then stained with uranyl acetate and lead citrate and characterized on a Hitachi H-700 model transmission electron microscopy (Hitachi Ltd., Japan).

Example 12

Confocal Immunofluorescence Microscopy

Cells were cultured on cover-slips coated with 2% gelatin overnight and treated with or without RA (10 µM) for 5, 15 and 30 min each. Then, cells were rinsed three times with PBS, fixed with 4% paraformaldehyde in PBS for 5 min and permeabilized with 2% FBS containing 0.4% Triton X-100 in PBS for 15 min. This reaction was blocked with 5% FBS at 4° C. overnight followed by incubation with primary antibody RXRα (1:100) or Gαq/11(1:100) in PBS at 4° C. overnight. After washing, cells were incubated with Dye Light 488 or Dye Light 549 conjugated secondary antibody (1:50; Rockland Immunochemicals Inc., Gilbertsville, Pa.) for 1 h. By incubation with DAPI (1:5,000) for 5 min, cover-glass was air dried and sealed for confocal immunofluorescence microscopy (Olympus, Tokyo).

Example 13

Analysis of Unique Population of Human Cytotrophoblasts Defined as hTS Cells

Cells obtained from the ectopic chorionic villi were cultured; colonies formed initially and subsequently proliferated into adherent fibroblast-like cells (FIG. 1a). Immunocytochemically, these cells expressed stage-specific embryonic antigen (SSEA)-1, -3, and -4 (FIG. 1b). These SSEAs-positive cells presented as the same of cytotrophoblasts histologically in the ectopic chorionic villi. However, in the term placental villi, they appeared mainly at the compartments of villous core.

To estimate the characteristics of stem cell, the flow cytometric analyses revealed that these cells expressed high levels of mesenchymal stem cell markers: CD90, CD44, vimentin, and neurofilament, and of trophoblast marker cytokeratin (CK)-7. They did not express hematopoietic stem cell markers: CD34 and CD45 and epithelial cell markers: E-cadherin, α6-integrin, and L-selectin. They also expressed weakly nestin and CD9 (FIG. 1c). These facts indicated that these cytotrophoblasts are distinct from the trophoblastic subpopulations isolated from mature placental tissues (Aboagye-Mathiesen et al., 1996; Baczyk et al., 2006). Moreover, other supportive evidence included: 1) treatment of these cells with all-trans retinoic acid (RA) resulted in a formation of giant cells (FIG. 1d) similar to the previous described (Yan et al., 2001); 2) a series of chromosome analyses showed unchanged karyotypes (see Supplemental FIG. 1a); 3) subsequent measurement of telomere lengths confirmed the chromosome stability (see Supplemental FIG. 1b); and 4) implantation of the cells on the severe combined immunodeficient mice created a positive immune chimeric reaction (see Supplemental FIG. 1c). Taken all together, these isolated cells likely represent a highly homogeneous population of cytotrophoblasts, exhibiting characteristics of mesenchymal stem cells. Therefore these cells are regarded as hTS cells.

Example 14

Similarity in Genetic and Biological Characteristics Between hTS and hES Cells

To investigate the gene profiling of hTS cells, transcriptase-polymerase chain reaction (RT-PCR) was performed with various primers (see Supplemental Table 1). The results showed that hTS cells expressed not only TS cell markers (Cdx2, BMP4, Eomes, and Fgfr-2) but also ES cell markers (Oct4, Nanog, Sox2, and FGF4) (FIG. 2a). The hTS cells were distinct from PDMS cells (a gift of Dr. C.-P. Chen) in gene distribution by comparing the global gene profiles analyzed by using Affymetrix Human Genome U133 plus 2.0 GeneChip (Santa Clara, Calif., http://www.affymetrix.com) (FIG. 2b).

Interestingly, hTS cells exhibited gene expressions of the three germ layers of ES cells, including: osteopontin, osteocalcin, perlecan, collagen type II, myogenin, myo D1, PPAR γ-2, and adipsin of mesoderm; neurofilament, neurogenin (Ngn)-3, CD133, MAP-2, Neo-D, and nestin of ectoderm; and insulin, Pdx-1, CK-19, somatostatin, Is1-1, Nkx-2.2, Nkx-6.1, and Pax-6 of endoderm (FIG. 2c). Functionally, hTS cells were able to differentiate to specialized phenotypes of mesodermal lineage, as seen in hES cells, by using appropriate regimens (In't Anker et al., 2004; Fukuchi et al., 2004; Yen et al., 2005) with modifications (see Supplemental Table 2), which included osteocytes, chondrocytes, myocytes, and adipocytes (FIG. 2d). The hTS cells were selectively induced to differentiate into dopaminergic NSCs and insulin-producing islet progenitor cells (see below), as representative of those derived from ectoderm and endoderm, respectively. These results demonstrated that hTS cells possess both genetic and biological characteristics of hES cells, which are capable of differentiation into specialized phenotypes of three germ layers.

Example 15

Nanog Maintains Pluripotency of Human Trophoblast Stem Cells by LIF Withdrawal

The effects of LIF withdrawal on human trophoblast stem (hTS) cells were examined since hTS cells expresses pluripotent gene markers of both embryonic stem (ES) cells and trophoblastic stem (TS) cells such as Oct4, Nanog, Sox2, and Cdx2 (FIG. 1a). hTS cells were treated with different dosages of LIF, i.e., 500 (mimic at ampulla), 250 (mimic at mid-portion), and 125 units (mimic at isthmus) for 3 days each, showing that LIF promoted Oct4 expression but represses Cdx2, Nanog, and Sox2 expressions in a dose-dependent manner (FIG. 1b). Quantitative PCR analyses supported these findings (FIG. 1c). As the relative expression ratio of Oct4 to Cdx2 enables to determine cell fate in early embryonic differentiation (Niwa et al., 2000), the Oct4/Cdx2 ratio (0.4-fold) appeared to be the highest at the ampulla which decreased to 0.2-fold at mid-portion and became near one at isthmic portion (FIG. 1d). This decreasing trend of Oct4/Cdx2 ratio actually facilitates the differentiation towards trophectoderm fate (Niwa et al., 2005). Remarkably, a higher Nanog/Cdx2 ratio (2-fold) appeared at cells treated with 125 units LIF, while 0.1-fold was noted at 500 units LIF. These results strongly suggested that Nanog as a rescuer of the relative decreased Oct4 expression is an important determinant for hTS cells to maintain the pluripotency. This role of rescuer was further supported by the prominently high Nanog/Oct4 ratio of LIF with 125 units compared to the ratio of LIF with 500 units and the apparent increase of Cdx2/Oct4 ratio at LIF with 125 units (FIG. 1e) No apparent change of Sox2/Cdx2 was found.

Collectively, these results demonstrated that the gradual withdrawal of LIF concentration from the ampulla toward isthmic portion of human fallopian tube induces mainly the elevation of Nanog in hTS cells, by which it maintains the self-renewal and pluripotent characteristics of hTS cells mimicking that in mouse ES (mES) cells and human ES cell growth without feeder cells. The results indicate that Nanog plays a role in maintaining the pluripotency of hTS cells Example 16

RA Enhances Nanog Expression

RA is a potent regulator of neuronal differentiation and normally, by binding to nuclear receptors that interact with retinoic acid response elements (RAREs) in regulatory regions of target genes (Maden). It has been shown that retinol (vitamin A), a supplier of RA production in cell, suppresses cell differentiation mediated by the upregulation of Nanog in ES cells (Chen). Whether or not RA exhibits a similar effect on Nanog in hTS cells was examine. The hTS cells were treated with RA for one day and subjected for flow cytometry. The results showed that RA promoted expressions of Nanog, Oct4 and Sox2 but not Cdx2 (FIG. 2f), which were consistent with the microarray mRNA expression profiling by Affymetrix GeneChip oligonucleotide microarrays (FIG. 2g). Furthermore, knockout of Nanog with siRNA suppressed RA-induced Nanog, but increased expression of Cdx2. In contrast, Cdx2 siRNA promoted Nanog and suppressed Cdx2 in the RA-induced hTS cells by flow cytometry (FIG. 2h). Taken together, these results indicated that the RA induces overexpression of Nanog in hTS cells, by which RA does not change the Nanog/Cdx2 ratio in deciding the cell fate.

Example 17

RA Promotes its Receptor RXRα Activation

RA promoted its receptor RXRα activation first in 5 min by Western blotting assay, however, this action sustained only for 30 min. Instead, an increased RARβ production was observed within 60 min (FIG. 2i). RA was observed to interact directly with RXRα and RARβ by immunoprecipitation assay (FIG. 2j). Furthermore, the activated RXRα translocalized towards the nucleus in a peak at 15 min and henceforth, the nuclear intensity declined by immunofluorescence microscopy (FIG. 2k). The protein G$\alpha_{q/11}$ subunit was also activated in 30 min (FIG. 2l). To this end, it is likely that RA interacts with RARs at the initial responsive stage without the assistance of cellular retinoic-acid-binding protein 2 (CRABP-2, FIG. 1d).

Example 18

RXRα/RARβ Might Belong to the Member of G Protein-Couple Receptors (GPCRs) Superfamily This concept was confirmed by observation of direct interaction between RXRα and G$\alpha_{q/11}$ subunit by double immunogold electron microscopy (FIG. 2m). Next, in order to link the relationship between RXRα/RARβ and Nanog, immunoprecipitation assay analysis suggests that RXRα, not RARβ, acts directly on the promoter of Nanog (FIG. 2n), Further, unlike ES cells, hTS cells contain the major RA generating enzymes: retinaldehyde dehydrogenase type 2 and 3 (RALDH-2 and -3) (FIG. 1d) which enables hTS cells to metabolize retinol into RA. It is demonstrated that RA acts on hTS cells to produce Nanog by the direct interaction with RXRα/RARβ complex in association with GPCRs to bind with the promoter of Nanog.

Example 19

RA-Induced Nanog Expression in hTS Cells is Affected by the Gradient LIF Content in the Fallopian Tube The withdrawal of LIF is able to enhance the RA-induced Nanog expression significantly in hTS cells by flow cytometry (FIG. 2i), suggesting that the hTS cell-derived NSCs stand at a position to be able to behave as progenitor cells by RA induction at the absence of LIF, maintaining the multipotent characteristics for neural subtype specification under an appropriate microenvironmental condition.

Example 20

RA Promotes TH Expression Via a Non-RARE Pathway

These results show that RA induces a nongenomic signaling pathway based on the initial results that RA stimulated RXR-α, RAR-β and c-Src expressions in 5, 120 and 5 min, respectively, in hTS cells measured by western blots (FIG. 3a). To determine whether the RXR-α/RAR-β interaction belongs to the superfamily of G protein-coupled receptors (GPCRs, double immunogold electron microscopy was used to investigate the interaction between G-protein $G\alpha_{q/11}$ and RXR-α. The results showed that RXR-α has a binding interaction with $G\alpha_{q/11}$ at the cell membrane (FIG. 3b) and subsequently, the dissociated $G\alpha_{q/11}$ stimulates membrane-bound phospholipase C beta (PLCβ) to cleave $PIP_2$ (a minor membrane phosphoinositol) into two second messengers, IP3 and diacylglycerol (DAG) (FIG. 3b).

Subsequently, RA induced a scaffold formation of RXRα, RARβ and [c-Src] by immunoprecipitation assay and using a specific c-Src inhibitor PP1 analog (FIG. 3c).

Example 21

RA Activates the Wnt2B/Fzd6/β-Catenin Pathway

Western blots analyses demonstrated that RA significantly upregulated Wnt2B and proto-oncogene FRAT1 after 4 hr and 24 hr incubation by Western blots (FIG. 24a). hTS cells were incubated with RA overnight with or without siRNA against Wnt2B. Flow cytometric analysis showed that RA significantly upregulated Wnt2B and its downstream targets, including the mediator protein Disheveled 3 (Dvl3) and proto-oncogene FRAT1, leading to the inhibitory glycogen synthase kinase-3β (GSK3β), which could be inhibited by knocking down Wnt2B by siRNA (FIGS. 24b and 24c). A similar result was also observed by RT-PCR analysis (FIG. 27). RA also promoted the overexpression of Fzd6 mRNA, member of the Frizzled family of 7-span transmembrane receptor (FIG. 24d). To validate the role of RA in the Wnt2B-mediated expression of Fzd6, we also analyzed the expression levels of Dvl3 and its downstream effector FRAT1 and showed that RA-mediated enhancement of Fzd6 could be abrogated by the presence of siRNA against Wnt2B with a concomitant decrease in GSK3β (FIGS. 24b and 24c). Subsequently, Western blots analysis showed that RA significantly activated β-catenin in between 30 min and 24 hr (FIG. 24e). RA induces a novel canonical Wnt2B/Fzd6/β-catenin signaling pathway, allowing the inhibitory GSK3β to stabilize and activate cytoplasmic β-catenin in hTS cells.

Example 22

RA Modulates Histone Deacetylase 6 (HDAC6)

Western blot analysis showed that RA promoted an elevation of Histone deacetylase 6 (HDAC6), a transcriptional regulation enzyme, in 2 hours, which enabled to directly interact with β-catenin after RA treatment for 24 hr by co-immunoprecipitation (IP) assay (FIG. 24f). Furthermore, we showed that a nuclear translocation of β-catenin occurred by cellular fractionation assay (FIG. 24g), supporting the presence of a canonical Wnt2B/Fzd6/β-catenin signaling pathway after RA treatment for 24 hr in the hTS cells. These observations were further confirmed by the confocal immunofluorescence microscopy. In the presence of siRNA against HDAC6, nuclear localization of β-catenin was blocked (FIG. 25). Interestingly, we found that a very early expression of β-catenin might appear in 5 min after RA treatment at the cell membrane (synapse) in the hTS cell-derived neuron-like cell. In the nucleus, β-catenin involves in transcriptional regulation by association with transcription factors of the TCF/LEF family. Cellular fractionation assay analysis showed that this interaction led to the nuclear translocation of β-catenin (FIG. 24e).

Example 23

Interactions Between RARβ and Gβ and Between RXRα and $G\alpha_{q/11}$

Western blots analysis in hTS cells demonstrated that RA induced rapid productions of both $G\alpha_{q/11}$ and Gβ at 30 min and also, retinoid X receptor α (RXRα) and retinoic acid receptor β (RARβ) at 30 min and 4 hr, respectively, (FIG. 26a). Analysis of real-time confocal fluorescence microscopy revealed that the GFP-tagged RXRα moved quickly from the cytosolic compartment towards the subcellular regions by RA stimulation within minutes (FIGS. 26b and 26c), where it co-expressed with $G\alpha_{q/11}$ immunocytochemically (FIG. 26d). This phenomenon was further supported by the double immunogold transmission electron microscopy wherein RA stimulated the binding of small gold-tagged RXRα and large gold-tagged $G\alpha_{q/11}$ at the cell membrane (FIG. 26e). Biochemically, RXRα physically interacted to $G\alpha_{q/11}$ and the action was inhibited by using RXRα siRNA by IP assay (FIG. 26f). A similar event took place between RARβ and Gβ and this action was also inhibited by using RARβ siRNA by IP assay (FIG. 26g). IP assay showed a selective c-Src inhibitor PP1 analog was able to prevent the formation of RXRα-RARβ heterodimer (FIG. 26h), suggesting the presence of an unknown mechanism that allowed RXRα and RARβ to function separately. This notion was further supported by the anchorage of the RA-induced gold particle-tagged RXRα in the endoplasmic reticulum (ER) observed by double immunogold transmission electron microscopy (FIG. 26i). Taken together, the data suggest that the RA-induced RXRα and RARβ interact independently with $G\alpha_{q/11}$ and Gβ, respectively, at the cell membrane.

Example 24

Akt3/mTOR Signaling and mRNA Translation

Real-time PCR (RT-PCR) analysis and found that RA induced a rapidly transient elevation of both RXRα mRNA and RARβ mRNA for only 15 min (FIG. 28a), and a rapid production of RARβ and RXRα within 1 hr (FIG. 26a). Focus on examining whether subcellular mRNA localization of RXRα was involved in these cellular processes based on the facts that there is enrichment of mRNA in axonal growth core and its association with mRNA localization in neurons and the RA-enhanced RARα levels mediate local GluR1 synthesis in the dendritic RNA granules, contributing to the RARα-modified translation for synaptic formation at neuronal membrane. Subsequently, IP assay showed that RA induced binding between Gβ and phosphatidylinositol 3-kinase (PI3K) (FIG. 26g) and activated PI3K with its downstream effectors all Akt isoforms, including Akt1 and Akt2 in between 30 min and 4 hr as well as a transient Akt3 in 1 hr by Western blots analysis (FIG. 28b). After treatment with RA for 24 hr, all expressions of Akt isoforms were inhibited by pretreating PI3K inhibitor Wortmannin by flow cytometry (FIG. 28c) and RT-PCR analysis (FIG. 29a), indicating the presence of Gβ/PI3K/Akt signaling. Notably, Akt has been recently emerged as a crucial regulator of neurite outgrowth to promote neuronal survival, the RA-induced Akt3 (4 hr) could bind to the mechanistic target of rapamycin (mTOR), which was inhibited by siRNA against Akt3 (FIG. 28d), leading to a temporal phosphorylation of mTOR at site serine 2448 in 4 hr detected by using specific antibody (Cell Signaling Technology). However, this action disappeared after 24 hr incubation (FIG. 28e). This function was inhibited by knockdown of Akt3 using siRNA by Western blots (FIG. 28f) and by flow cytometry (FIG. 29c). Immediately, Western blots analysis showed that by RA treatment for 4 hr, phosphorylated mTOR interacted directly with eukaryotic translation initiation factor-4E binding protein 1 (eIF4EBP1) (FIG. 28g) and activated eIF4EBP1 (FIG. 28h). Knockdown of phosphorylated mTOR by using siRNA, phosphorylation of eIF4EBP1 was inhibited; instead phosphorylation of elongation initiation factor 4E (eIF4E) was activated (FIG. 28h), implicating that a dissociation of eIF4E from the eIF4E/eIF4EBP1 complex occurred. Phosphorylation of eIF4E enables to cause cap-dependent translation of mRNA. Overall, these observations explain how RA enables to induce subcellular mRNA translation through the activation of RXRα mRNA and RARβ mRNA to locally produce RXRα and RARβ, respectively, because knockdown of eIF4E by siRNA both interactions between RXRα and $G\alpha_{q/11}$ and between RARβ and Gβ were inhibited by IP assays (FIG. 28i). These results support that Akt3/mTOR signaling plays as an initiator of local synthesis of RXRα and RARβ. Although RA stimulated elevation of elongation initiation factor 4B (eIF4B), this action was not influenced by siRNAs against either mTOR or 4EBP1, suggesting another mechanism in regulating eIF4B expression (FIG. 28h). The spatiotemporal Akt3 promotes subcellular localization for RXRα and RARβ productions via mTOR signaling.

Example 25

CREB1 on the Mainstream in Dopaminergic Specification

Gβ/PI3K downstream effector Akt1 directly binds and activates cAMP responsive element binding protein 1 (CREB1) through phosphorylation at serine 133 site (FIG. 30a). The interaction of Akt1 and CREB1 was inhibited by Akt1 siRNA (FIG. 30b). The phosphorylated CREB1 targeted and transcribed dopamine precursor tyrosine hydroxylase (TH) gene by chromatin immunoprecipitation (ChIP) assay (FIG. 30c), which was inhibited by CREB1 siRNA (FIG. 30d). To this end, results suggested that the RA-induced RARβ/Gβ/PI3K/Akt1/CREB1 pathway played a role in the TH transcription in dopaminergic neurogenesis. To support this notion in vivo, a model with 6-OHDA-induced PD rats who received intracranial transplantation of the hTS cell-derived trophoblastic NSCs (tNSCs) at the lesioned striatum was used. Examination of the brain sections at 12-week postimplantation revealed that in the substantia nigra compacta, co-expression of CREB1 and TH was observed in the newly dopaminergic (DA) neurons in the newly dopaminergic (DA) neurons in the therapeutic side compatible with that in the normal side by immunofluorescence tissue analysis (FIG. 30e). Both TH and CREB1 activities were higher in the regenerated DA neurons compared to that normal ones (FIG. 30f). Interestingly, an apparent CREB1 expression was observed in the nucleous of DA neurons. These findings may explain why CREB1-deficient mice are susceptible to neurodegeneration.

Example 26

Study of RXRα/$G\alpha_{q/11}$ in ER Calcium Regulation

Western blots analyses in between 30 min and 4 hr showed that RA induced gradual activation of $G\alpha_{q/11}$ that triggered the catalysis of the membrane-bound phospholipase C (PLC-β), leading to the degradation of membrane phosphoinositol PIP2 (FIG. 21a) to produce second messenger inositol (1, 4, 5) triphosphate (IP3) consistent with the conventional Gα signaling described previously. IP3 activated its receptor IP3R (FIG. 21a) located at ER, causing intracellular calcium elevation (FIG. 21b). To ascertain the origin of intracellular calcium, cells were cultured in the calcium-free medium wherein RA induced a transiently intracellular $Ca^{2+}$ release by real-time live cell immunofluorescence microscopy (FIG. 21b-a). The depletion of ER calcium level could be rescued by adding extrinsic $CaCl_2$ for homeostasis and cell protection, exhibiting a pattern of the store-operated calcium entry (SOCE). The process of calcium release in the ER was inhibited by IP3R specific inhibitor 2-APB, in a dose-dependent manner (FIG. 21b-b). These results indicate that the ER-released intracellular calcium elevation is responsible for the RA-induced $G\alpha_{q/11}$ signaling pathway in hTS cells.

KCl could activate L-type calcium channels after the RA-induced depletion of ER calcium in the calcium-free medium in hTS cells (FIG. 21b-c). The L-type calcium channel antagonist nifedipine was able to block this signaling (FIG. 21b-d). RA regulation of intracellular ER calcium was associated with L-type calcium channels.

Example 27

Investigation of CaMKII in Excitation-Neurogenesis Coupling

Western blot analysis indicated that RA induced a spatiotemporal activation of CaMKII in 1-2 hr (FIG. 21a). Immunoprecipitation assay analysis demonstrates that CaMKII directly phosphorylated and activated CREB1 (FIG. 21c) compatible with the previous study that CaMKII encodes L-type calcium channel activity locally to signal to nuclear CREB in excitation-transcription coupling. Western blot analysis indicated that eukaryotic initiation factor 4B eIF4B siRNA inhibited expressions of CaMKII, calcineurin, and eIF4B (FIG. 21d). Axons contain a variety of mRNA encoding specific protein synthesis locally, including CaMKII, calcineurin, and CREB1 in developing neurons. CREB1 enables the retrograde trafficking for specific transcriptional processes in the nucleus responsible for the signal of distal axons. The extrinsic RA-triggered local protein synthesis of CaMKII can be inhibited by eIF4B siRNA in hTS cells. Therefore, this locally activated CaMKII signal behaved similarly to CREB1, suggesting a rapid inducible gene transcription upon extracellular cues.

The transient CaMKII bound and activated eukaryotic initiation factor 4B (eIF4B) (FIG. 21c) to initiate mRNA translation machinery via a cap-independent mechanism. Western blot analysis indicated that this action was inhibited by a selective CaMKII inhibitor KN93 after RA treatment (FIG. 21e). This CaMKII/eIF4B signaling then integrated eIF4B/c-Src/Nanog signaling pathway to accomplish the signaling pathway from RXRα/$G\alpha_{q/11}$ to Nanog for self-renewal and proliferation of tNSCs. These results first explored that the $G\alpha_{q/11}$ signal-derived CaMKII excitation was involved in the maintenance of self-renewal of tNSCs.

Western blot assay and immunoprecipitation assay analyses demonstrated that CaMKII binds to and activates parkinson protein 2 (parkin) (FIGS. 21a and 21f). In turn, parkin directly interacted and activated microtubule-associated protein tau (MAPT) (FIGS. 21a and 21f), which is preferentially located in axons and stimulates microtubule assembly. Consequently, MAPT directly bound to SNCA (FIGS. 21a and 21g) to form a parkin/MAPT/SNCA complex. Where MAPT interact and activate tubulin (FIGS. 21a and 21h), a microtubule element expressed exclusively in neuron that stabilizes and promotes microtubule assembly. Together, these results suggested the importance of axonal behaviors in early neurogenesis.

Example 28

Activation of Calcineurin/NFAT1 Signaling

Western blot assay analysis demonstrated that RA induced production of calcineurin (FIG. 21a). Pretreatment with 2-APB inhibited Calcineurin, NFAT1, and MEF2A expression (FIG. 21i), linking the ER calcium and calcineurin molecules. Calcineurin immediately dephosphorylated NFAT1, a key regulator of T cell activation and anergy, showing a transient fashion in 30 min to 2 hr (FIG. 21a). This action was also inhibited by 2-APB as evidenced by immunoprecipitation assay analysis (FIG. 21h), linking the ER calcium to calcineurin/NFAT1 signaling. Moreover, RA induced a transient interaction of NFAT1 and importin, a nucleocytoplasmic transporter (FIGS. 21a and 21j), leading to the NFAT1 nuclear translocation by cell fractionation assay (FIG. 21k). This temporal effect of NFAT1 is thought to be one mechanism by which cells distinguish between sustained and transient calcium signals.

Example 29

Study of Wnt and G Protein Signaling Pathways

The inhibitory GSK3β (at serine/theronine site) of canonical Wnt signaling maintained stabilization of cytoplasmic β-catenin after treating RA overnight but with a slightly decreased levels in 30-120 min (FIG. 24d). Unexpectedly, among Akt isoforms Akt2 was able to bind GSK3β in 4 hr (FIG. 21l); however, flow cytometric analysis showed that GSK3β was initially activated in 4 hr but transited into inhibitory later by RA treatment overnight (FIG. 21m). This phenomenon was further confirmed by using Akt2 siRNA (FIG. 21n). To explain this functional divergence, it was confirmed that the initial activation of GSK3β was due to the phosphorylation at Tyr216 site by Akt2 followed the inhibition was due to the phosphorylation at serine/theronine site (FIG. 21m). These results demonstrate that site-specific phosphorylation of GSK3β by various protein kinases determines the fate of downstream effector. Moreover, active GSK3β phosphorylated MAPT via direct interaction (FIG. 21h). In turn, MAPT interacted with and activated tubulin (FIGS. 21a and 21h) to promote microtubule assembly. Notably, the conversational bridges among Wnt2B, Gβ, and Gα$_{q/11}$ signaling pathways are constructed during early neurogenesis.

Example 30

Study of Transcription Factors for Dopaminergic Neurogenesis

In the nucleus, interaction of β-catenin and CREB1 represented a mainstream in TH transcription (FIG. 30a). Active β-catenin, in turn, bound to lymphoid enhancer factor 1/T cell factor 1 (LEF1) (FIG. 22a), leading to the switch of LEF1 from repressor to activator of transcription. LEF1 then recruited and interacted with Pitx2, member of a superfamily of bicoid-related factor (FIG. 22a). Whereas LEF1 promoted Pitx2 gene transcription but not Pitx3 gene by chromatin immunoprecipitation (ChIP) assay (FIG. 22b) compatible with that β-catenin, Pitx2, and LEF1 interact to synergistically regulate the LEF-1 promoter.

Furthermore, the transient nuclear active NFAT1 plays as transcription factor to produce cytokines and TNF-α for immune responses. However, this action was unlikely to occur in the present case because the phosphorylated GSK3β enables to inhibit the DNA binding of calcineurin-induced NFAT1 in the nucleus and to promote nuclear export. Therefore, active cytoplasmic NFAT1 would interact and activate cytoplasmic transcription factor myocyte enhancer factor 2A (MEF2A) (FIGS. 22c and 22d) because this action was inhibited by NFAT1 siRNA (FIG. 22e). Notably, the rapid inducible CREB1 entered the nucleus and transcribed MEF2A gene that produced MEF2A protein (FIG. 22f). MEF2A might function in multiple ways at gene transcription (FIG. 22g), including transcription itself via auto-regulation to produce more MEF2A, transcription TH gene for dopaminergic specification, transcription SNCA gene for SNCA/MAPT/parkin complex formation, and interaction with EP300 and Pitx2, which was inhibited by MEF2A siRNA (FIG. 22h).

The active ER300 not only targeted HDAC6 gene but also TH gene by ChIP assays (FIG. 22i). HDAC6 then enabled to carry β-catenin for nuclear translocalization (FIGS. 24e and 24f). Taken together, an executive transcription complex was formed and destined for TH gene transcription. Among them, CREB1, EP300, and MEF2A were able to directly target promoter of TH gene while β-catenin, LEF1, and Pitx2 performed as co-activator of enhancer during transcription processes. Western blots analysis show the various molecular activities at 4 hr and 24 hr (FIG. 22j).

Example 31

Animal Studies

For animal study, reporter cells were prepared by transfecting the F1B(−540)-GFP and pSV2neo plasmids into hTS cells followed by selection with G418. Greater than 95% of hTS cells showed co-expressions of F1B-GFP and TH-2. Second, Parkinson's disease was induced in "young" Spraque-Dawley rats (n=12, body weight, 225-250 gm) by injecting neurotoxin 6-hydroxydopamine (6-OHDA) into rat brain unilaterally as described below.

All experiments were conducted and performed according to the guidelines of the ethical board of the Institutional Review Boards of the Hospital, Kaohsiung Medical University Hospital and Ethical Committee at Medical College of National Chung Kong University, Tainan, Taiwan.

Induction of Parkinsonism

Twelve Sprague-Dawley rats (560+65 g (pre), 548+46 g (post) of body weight) were used as model for 6-OHDA-lesioned hemiparkinsonism (Javoy et al., Brain Research, 102:201-15, 1976). For surgery, after anesthesia by chloral hydrate (4%, 1 cc/100 g of body weight), stereotaxic lesions were carried out by infusion of 6-hydroxydopamine (Sigma) into the right median forebrain bundle (AP 2.8/Lat 2.2/Dep 8.0 mm) at a rate of 1 µg/0.5 µl/min for 8 min (injection pump: CMA 100). After 10 min, the tube was removed. Two weeks later, apomorphine-induced rotation was tested in a plastic bowl (36 cm in diameter) 20 min after receiving apomorphine injection (25 mg/kg) subcutaneously. The contralateral turning rotation was monitored and recorded for 20 min using a video camera. Rats with the number of rotations over 25 per 5 min were eligible for the study. For cell transplantation, cells were transplanted into two sites (each site: $3 \times 10^6/4$ µl) within the right unilateral striatum (1st site: AP+1/Lat+2.7/Dep 6.4 mm; $2^{nd}$ site: AP+0/Lat+2.7/Dep 6.4 mm). The control group was given PBS with the same approach. Apomorphine-induced rotation was measured at 0, 3, 6, 9, and 12 weeks after cells injection. The results were expressed as contralateral turns/5 min (FIG. 5A).

In order to examine the effects of NSCs induced by different time of RA, the eligible rats were randomly divided into three groups: the one- and the 5-day RA-induction groups and the control. Before transplantation, hTS cells were transfected with F1B-(−540)-green fluorescent protein (GFP) and pSV2neo recombinant plasmid DNA followed by G418 selection to achieve a yield over 95%. Each rat received GFP-tagged NSCs with $6 \times 10^6$ cells in total and the control one received phosphate-buffered saline as vehicle. The therapeutic effect was assessed by apomorphine-induced rotation test (Iancu et al., 2005) every 3 weeks after implantation.

Experiment 1

Adult Sprague Dawley rats (BW: 225-250 g) were used as graft recipients and housed on a 12 h light/dark cycle with ad libitum access to food and water. The lesioned rats (n=12) were first divided into three groups: (a) lesioned and transplanted with one-day RA-induced NSCs (n=4), (b) lesioned and transplanted 5-day RA-induced NSCs (n=4) and (c) lesioned and non-transplanted control (n=4). Rats were anesthetized by Zoletil (50 mg/kg, s. c., Virbac Lab. Carros, France) and the lesioned rats were unilaterally injected with 6-OHDA (8 µg/4 µl in 0.1% 1-ascorbic acid-saline; Sigma-Aldrich, Mo.) into the left MFB (AP 2.8, Lat 2.0, Dep 8.0 mm) and SN (AP 5.0, Lat 2.2, Dep 7.5 mm) according to bregma and dura in mm and awaiting for 10 min at the site. Transplantation of the hTS cell-derived NSCs ($1 \times 10^6$ cells/5 µl/5 min) into the DA-depleted striatum at two sites (AP+1.0, Lat+2.7, Dep 6.4 and AP+0, Lat+2.7, Dep 6.4) and the cannula was left in place for 5 min before slowly retracting it. The cell viability remained stable between 96 and 98% during the implantation procedure. Sham rats received vehicle without cells. Lesion was evaluated by means of apomorphine-induced rotation every one week after the 6-OHDA lesion to achieve a stable hemiparkinsonian status (>300 rotations/h). Graft effect was assessed every 3 weeks by apomorphine-induced rotation test until 12 weeks. At 18 weeks postimplanation, rats were sacrificed and brain sections were subjected for TH-DAB immunostaining.

Experiment 2

The PD rats were controlled at pre-test with 560+/−65 g and post-test at 548+/−46 g in body weight. The lesioned rats (n=16) were created as in the experiment 1 and divided into two groups: (a) lesioned and transplanted with cells (n=8) and (b) lesioned and transplanted without cells as control (n=8) by transplantation with one-day RA-induced NSCs. Cells were grafted by injection at AP+1.0, Lat+2.7, Dep 6.4. Behavioral assessments were carried out every 3 weeks until 12 weeks postimplantation as described below. At 13 weeks, all rats were sacrificed and the brain sections were subjected for TH-DAB immunostaining and the TH-positive cells were analyzed by densitometry.

Behavioral Assessments
Locomotor Activity Assays.

For rats, spontaneous locomotor activity was monitored in a circular corridor (10 cm wide and 60 cm in diameter with walls 30 cm high; Med Associates Inc., St Albans, Vt.). Four photoelectric cells located equidistantly around the walls of the circles detected an animal's horizontal ambulatory activity by way of beam interruptions. Data were recorded via a PC equipped with customized software (Med Associates). Separate groups of animals were tested with 10 mg/kg (n=6 per group) and 20 mg/kg (n=12 per group) cocaine. Animals were randomized into treatment groups (HSV-LacZ and HSV-RGS9-2) and habituated to the locomotor apparatus for 2 hr. On the next day, animals received HSV vectors in the nucleus accumbens shell on a stereotaxic frame. Following 2 days of recovery, animals were tested with cocaine on locomotor activity for 2 hr. Data were analyzed by two-way ANOVA (HSV×time) with Bonferroni post hoc test.

For mice, locomotor activity was determined in an automated system in which the activity chambers were plastic cages (12×18×33 cm) with 10 pairs of photocell beams dividing the chamber into 11 rectangular fields (Hiroi et al., 1997). Mice were tested at the same time each day by an experimenter who did not know the genotype of the mice. For acute experiments, animals were habituated to the chambers for 30 min, after which time they received i.p. injections of saline or varying doses of amphetamine, cocaine, or apomorphine, and locomotor activity was assessed for an additional 30 min. For chronic experiments, animals were placed in the chambers immediately after an i.p. saline injection on the first 3 days. Horizontal activity was then measured for 10 min. On days 4-8 (C1-C5), animals were given cocaine (7.5 mg/kg i.p.) and activity was measured for 10 min. The short time periods used for rats and mice have been shown in previous studies to avoid the potentially confounding effects of stereotypy in measures of ambulatory locomotor activity.

Three behavioral tests were performed: (i) drug-induced rotation to assess lesion and graft effects, (ii) footprint analysis to evaluate hind limb gait patterns, and (iii) the ladder rung walking test to assess skilled walking performance (hind limb/forelimb coordination and paw placing accuracy).

Apomorphine-Induced Rotation Test.

Briefly, rat was placed in a large round chamber (16 cm in diameter) for a period of 40 min after apomorphine administration subcutaneously (0.5 mg apomorphine in 0.01% ascorbic acid in 0.9% normal saline/kg body weight, Sigma-Aldrich). All rotations were recorded on the videotape and the net rotation asymmetry was calculated. Data were calculated as numbers of total turn in 30 min. Data were analyzed by using Matlab software.

Figure 2:
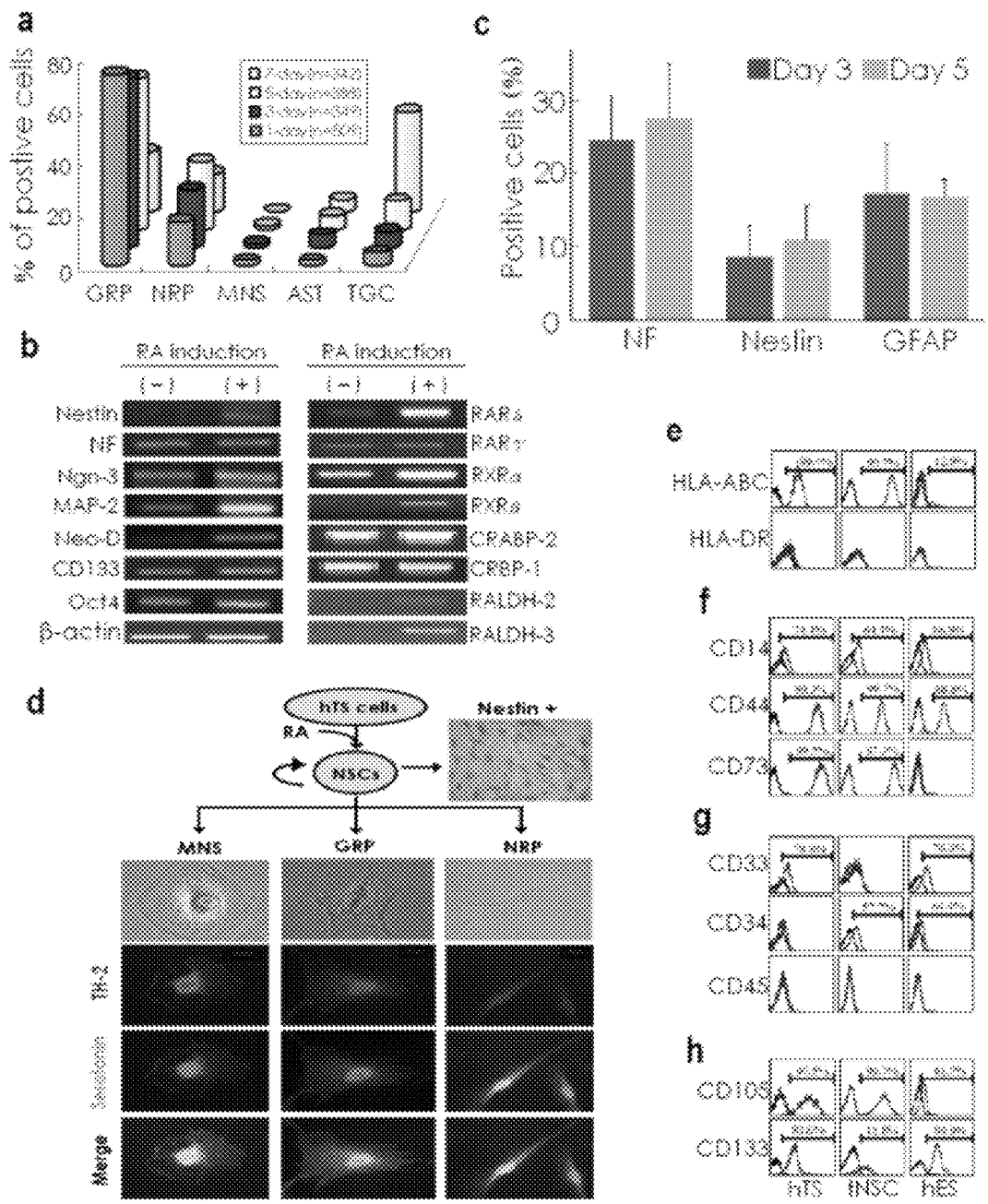
FIG. 2 illustrates retinoic acid (RA) induced hTS cell differentiation into a variety of phenotypical neural stem cells. (2a) Distribution of various neural progenitor subtypes, including glial restricted precursors (GRP), neuronal restricted precursors (NRP), multipotent neural stem (MNS) cells, astrocytes (AST), and undefined trophoblast giant cells (TGC). The frequency of the hTS cell-derived neural progenitor subtypes distributed in consistent ratios during RA induction with time, (e.g. 1, 3, 5 and 7 days), shown from the first to the fourth row, respectively. n: indicating total cell number counted. (2b) RT-PCR analysis of hTS cell expression of neural stem cell-related genes before and after 1-day RA (10 μM) induction, including nestin, Oct4, neurofilament, Ngn3, Neo-D, MAP-2 and CD133, generated from RA (10 μM) induced hTS cells. (2c) Both 3- and 5-day RA-induced hTS cells expressed positive immunoreactive neural stem cell genes, including neurofilament protein, nestin, and GFAP, which sustained a similar ratio in distribution as observed by flow cytometric analysis. (2d) Immunocytochemical analysis of the (neural stem cells) tNSCs expressed immunoreactive nestin, tyrosine hydroxylase-2 (TH-2), and serotonin. (2e) Comparative expression of the immune-related genes among hTS cells, tNSCs and (human embryonic stem) hES cells by flow cytometric analysis: HLA-ABC (MHC class I) expressed highly in hTS cells (99.4%) and tNSCs but lower in hES cells. HLA-DR (MHC class II) did not express in the cells. (2f) Comparative expression of the immune-related genes among hTS cells, tNSCs and hES cells by flow cytometric analysis: No difference observed in CD14 and CD44 expression among the cells. Proliferative factor CD73 expressed highly in hTS cells and tNSCs, but negatively expressed in hES cells. (2g) Comparative expression of the immune-related genes among hTS cells, tNSCs and hES cells by flow cytometric analysis: transmembrane receptor CD33 is expressed in hTS and hES cells but not in tNSCs. CD45 did not express in the cells. (2h) Comparative expression of the immune-related genes among hTS cells, tNSCs and hES cells by flow cytometric analysis: no difference in intensities was found among hTS cells, tNSCs and hES in the expression of mesenchymal stem cell marker CD105, however, less cancer stem cell marker CD133 (11.8%) was expressed in tNSCs compared to hTS cells (93.6%) and hES cells (98.8%).

Apomorphine-induced rotation (apo) was also observed for 60 min after intraperitoneal injection of 0.5 mg/kg apomorphine solution (Sigma-Aldrich, 0.5 mg apomorphine in 0.01% ascorbic acid of 0.9% normal saline). Rotational bias was assessed in rotometer boxes after the lesion (2 and 3 weeks post LX) and after the transplantation (3 and 6 weeks post TX) as described previously ([59]; FIG. 2). Data of the 2 weeks post LX and 3 weeks post TX drug-induced rotations are not shown. Three days later amphetamine-induced rotation (amph) was carried out for 90 min after intraperitoneal injection of 1 ml/kg amphetamine solution (Sigma-Aldrich, Steinheim, Germany: 2.5 mg d-amphetamine per 1.0 ml saline). Five animals were excluded from the study because they showed <4.0 full body turns contralaterally to the lesioned side after apomorphine injection and <6.0 full body turns ipsilaterally to the lesioned side after amphetamine injection. Apomorphine-induced rotation is presented as net rotation in negative values, and amphetamine-induced rotation is presented as net rotation in positive values.

Drug-induced rotation after the injection of apomorphine (A) and the injection of amphetamine (B). The rotational bias is shown as the total amount of full body rotation. The dollar sign ($) indicates a significant difference between the sham and the tx rats. pre TX=6 weeks after the lesion, post TX=6 weeks after the transplantation. Note that there were significant graft effects (reduction of rotational bias after apomorphine injection; overcompensation after amphetamine injection).

Bar Test for Akinesia.

For the bar test, rat was placed gently on a table with a posture that both the contralateral and ipsilateral forepaws were placed alternatively on a horizontal acrylic bar with 0.7×9 cm in size. The time from placing of forepaws to the first complete removal of each of them from the bar was recorded. Total time spent by each paw on the blocks was recorded as described previously (Fantin).

Footprint Analyses (Spatiotemporal Gait Analyses).

Footprint analyses including walking speed, step length, stride length and base of support were performed to evaluate hind limb walking patterns as described previously (Klein). The rats had to walk on a plastic board through a walkway (50 cm long, 8 cm wide). The parameters including stride length, limb rotation (angle between a virtual line through the third digit and the centre of the palm and a virtual line parallel to the walking direction) and distance between feet (distance between feet of the left and right stepping cycle) with five sequential steps were recorded by a video camera (Casio EX-F1, Japan) and analyzed by Matlab software.

Ankle joint rigidity assessment is evaluated using suitable methods. Suitable Electrophysiological assays are used to determine % dopaminergic neuron recovery in the brain.

Immunohistochemistry

For TH immunohistochemistry, the animals received a terminal dose of 60 mg/kg sodium pentobarbitone i.p. (Apoteksbolaget, Sweden) and were trans-cardially perfused with 50 ml saline (0.9% w/v), followed by 200 ml ice-cold paraformaldehyde (4% w/v in 0.1 M phosphate buffered saline). The brains were removed, post-fixed for 2 h in 4% paraformaldehyde and cryo-protected overnight in sucrose (25% w/v in 0.1 M phosphate buffered saline) before being sectioned on a freezing microtome (Leica). Coronal sections were collected in 6 series at a thickness of 20 μm.

Immunohistochemical procedures were performed as follows. Free-floating sections were incubated with primary antibodies overnight at room temperature in an incubation solution of 0.1 M phosphate buffered saline with potassium containing 5% normal serum and 0.25% Triton X-100 (Amresco, USA). Secondary antibodies were diluted in phosphate buffered saline with potassium containing 2% normal serum and 0.25% Triton X-100 and applied to the original solution for 2 h at room temperature. Detection of the primary-secondary antibody complexes was achieved by peroxidase driven precipitation of di-amino-benzidine, or conjugation of a fluorophore (either directly to the secondary antibody or with a streptavidin-biotin amplification step where necessary). For detection of c-Fos, nickel sulphate (2.5 mg/ml) was used to intensify the staining. Slide mounted sections labeled with fluorescent markers were cover-slipped with polyvinyl alcohol-1,4-diazabicyclo[2.2.2]octane and di-amino-benzidine labeled sections were dehydrated in alcohol and xylene and cover-slipped with DePeX mounting media (BDH Chemicals, UK). Primary antibodies and dilution factors were as follows: mouse anti-Calbindin$_{28KD}$ (1:1000: Sigma), rabbit anti-c-Fos (1:5000, Calbiochem), chicken anti-GFP (1:1000; Abcam), rabbit anti-GFP (1:20 000; Abcam), rabbit anti-GIRK2 (1:100; Alomone Labs, Jerusalem, Israel) rabbit anti-PITX3 (1:100; Invitrogen) and mouse anti-tyrosine hydroxylase (TH: 1:4000; Chemicon). Secondary antibodies, used at a dilution of 1:200, were as follows: (i) direct detection-cyanine 3 or cyanine 5 conjugated donkey anti-mouse, cyanine 2 conjugated donkey anti-chicken, cyanine 5 conjugated donkey anti-mouse (Jackson ImmunoResearch); and (ii) indirect with streptavidin-biotin amplification-biotin conjugated goat anti-rabbit or horse anti-mouse (Vector Laboratories) followed by peroxidase conjugated streptavidin (Vectastain ABC kit, Vector laboratories), or cyanine 2/cyanine 5 conjugated streptavidin (Jackson ImmunoResearch).

In Vivo Study on CREB1 Expression in Dopaminergic Specification

To obtain the brain sections, rats were anesthetized by sodium pentobarbitone (60 mg/kg i.p., Apoteksbolaget, Sweden) and trans-cardially perfused with saline (50 ml, 0.9% w/v) followed by ice-cold paraformaldehyde (200 ml, 10% w/v in 0.02 M PBS) were performed at 18- and 12-week in the acute and chronic PD rats, respectively. Brain sections were subjected for immunocytochemistry, immunohistochemistry, and immunofluorescence tissue analysis as indicated.

The 6-OHDA-induced PD rats who received intracranial transplantation of the hTS cell-derived trophoblastic NSCs (tNSCs) at the lesioned striatum were examined to investigate CREB1 expression. Examination of the brain sections at 12-week postimplantation revealed that in the substantia nigra compacta, co-expression of CREB1 and tyrosine hydroxylase (TH) was observed in the newly dopaminergic (DA) neurons in the therapeutic side, compatible with that in the normal side by immunofluorescence tissue analysis (FIG. 30e, insert). Both TH and CREB1 activities were higher in the regenerated DA neurons compared to that normal ones (FIG. 30f). An apparent CREB1 expression was observed in the nucleus of DA neurons. These findings can assist in the explanation of how CREB1-deficient mice are susceptible to neurodegeneration In Vivo Study on Regeneration of the Dopaminergic Nigrostriatal Pathway To further verify the regeneration of the dopaminergic nigrostriatal pathway after cell therapy, immunofluorescence tissue analysis was performed (TissueGnostics Gmbh, Vienna, Austria). Brain sections were investigated, including 14 acute PD rats (i.e., 2 at 1-week and 2 at 6-week post-injury and 2 controls, 6 at 12-weeks after cell transplantation and 2 controls) and 4 chronic PD rats (i.e., 2 at 12-week after cell therapy and 2 controls). In the SNC, 6-OHDA caused progressive neural degeneration, resulting in various sizes of cavity at 6 weeks post-injury (FIG. 31). Intriguingly, after tNSCs therapy, numerous DA neurons appeared at the wall of the cavity with TH-positive nervous terminals projecting into the cavity (FIG. 31, insert). Quantitative analysis showed that the number of DA neurons reduced apparently to 48% and 13% at 1- and 6-week post-injury in the SNC, respectively, compared to the intact side (FIGS. 32a and 33). Remarkably, the loss of DA neurons could be reduced by up to 67% after tNSCs therapy.

While in the striatum, DA neurons reduced to 78% and 4% at 1- and 6-week post-injury, respectively (FIG. 32a). Similarly, the lost DA neurons could be regenerated by up to 73% after tNSCs therapy. Consistent with observations (FIG. 6), DA neuronal circuitries were well-established in the therapeutic side of SNC similar to the intact side immunohistochemically (FIG. 32b). The recovery rate of DA neurons counted for 78.4±8.3% (mean±SEM; n=4) in the SNC (FIG. 32c) compatible with the 67% in the immunofluorescence analysis (FIG. 23a).

Since glial cells play as mediators in guiding the migration of neurons to their destinations or as sources of neural regeneration, 6-OHDA caused not only degeneration of both DA neurons and GFAP(+) cells but also disarrangement of the striato-pallido-nigral axons in the striatum (pencils of Wilson). These phenomena were clearly improved after tNSC therapy, showing numerous GFAP(+) cells embedded in the fine myelinated fibers (FIG. 32d). As noted, the GFAP(+) cells regenerated from 65.5% at 6 weeks post-injury to 93.9% after tNSC therapy in the lesioned striatum (FIG. 32e). This fact might reflect astrocytic activation, attributable to the implanted tNSC subtypes, i.e., GRP and astrocytes. These results indicate that transplantation of tNSCs regenerates the dopaminergic nigrostriatal pathway in chronic PD rats thereby explaining the improvement of behavioral deficits. Optimizing the regeneration of DA neurons would continue for at least 18 weeks postimplantation based on the retention of tNSCs in the lesioned pathway (FIG. 5).

In vivo, hTS cells were implanted into male severe combined immunodeficient (SCID) mice intramuscularly for 6-8 weeks. Histologically, no teratoma was found; but minor chimeric reaction with myxoid-like bizarre cells was observed between the muscle fibers (FIG. 7H). These results reveal the advantage of hTS cells and tNSCs in translational medicine compared to hES cells with respect to teratoma formation.

Statistics

All data are expressed as mean±SEM. Differences were assessed by using repeated measure analysis of variance (ANOVA) tests (SPSS Release 12.0 software) and applied least significant difference test (LSD) post hoc comparisons after repeated measure ANOVA tests between two groups for apomorphine-induced rotation analyses. Student t test, paired t test was used when appropriate. p-value <0.05 was considered significant.

The animal experiments show that tNSCs injected into the lesioned striatum are able to migrate upstream to subnigral nucleus via nigrostriatal pathway evidenced by GFP-tagged immunofluorescence study after 18 weeks implantation. Second, the efficacy in improving behavioral deficits is higher than expected, for example, recovery of dopaminergic neurons 12 weeks post-implantation is 28.2%. Third, there is neither immunosuppression nor tumorigenesis observed. Further, the improvement in 28.2% dopaminergic neurons and behavioral deficits is maintained in a chronic PD rat over one year after 6-OHDA induction. These results indicated that transplantation of tNSCs was able to regenerate the dopaminergic nigrostriatal pathway and functionally improve the behavioral impairments in acute PD rats.

Chronic PD Animal Model

To more closely mimic the pathologically progressive nature of PD patients, a chronic PD rat model was developed by breeding methods over one year (12.3 months in average). The apomorphine-induced rotation test was performed monthly to ascertain the rats' PD state throughout the experiment. Group I (n=6) received tNSCs while group II was the control (n=6). Behavioral assessments were performed every 3 weeks, including the apomorphine-induced rotation test, the bar test for akinesia, the stepping test for rigidity, and the footprint analyses for postural imbalance and gait disorder.

In Group I, a significant improvement of the apomorphine-induced contralateral rotations was achieved from 3 weeks to 12 weeks postimplantation similar to the previous study in acute PD rats (FIG. 6A). The bar test showed that the grasping time of the affected forelimb was significantly shortened at 3 weeks, and continued to improve at 12 weeks (FIG. 6B). All assessments by step length (FIG. 6C), stride length (FIG. 6D), walking speed (FIG. 6E), and base of support (FIG. 6F) revealed significant improvement from 3 weeks to 12 weeks postimplantation. These studies were performed on a well-designed walkway (FIG. 6G). These results indicated that transplantation of tNSCs was able to regenerate the dopaminergic nigrostriatal pathway and functionally improve the behavioral impairments in chronic PD rats.

Example 32

Pull and Push Mechanism

G protein-coupled receptors (GPCRs) communicate between internal and external environments and couple with heterotrimeric G proteins at the cell membrane. However, the mechanisms that explain how the activated GPCRs initiate this process are less clear. A recent report has shown that upon the introduction of ligand, both $G\alpha_{13}$ and $G\alpha_{q/11}$ subunits interact with AhR-interacting protein where $G\alpha_{13}$ leads to the destabilization, translocation and ubiquitination of cytosolic AhR. The role of G protein signaling in the nongenomic AhR pathway was explored. BBP was chosen as an exogenous ligand and COX-2 as an activated target, as COX-2 causes inflammation, metabolism and carcinogenesis in a variety of human cells, including hepatic cancer cells.

Figure 14:
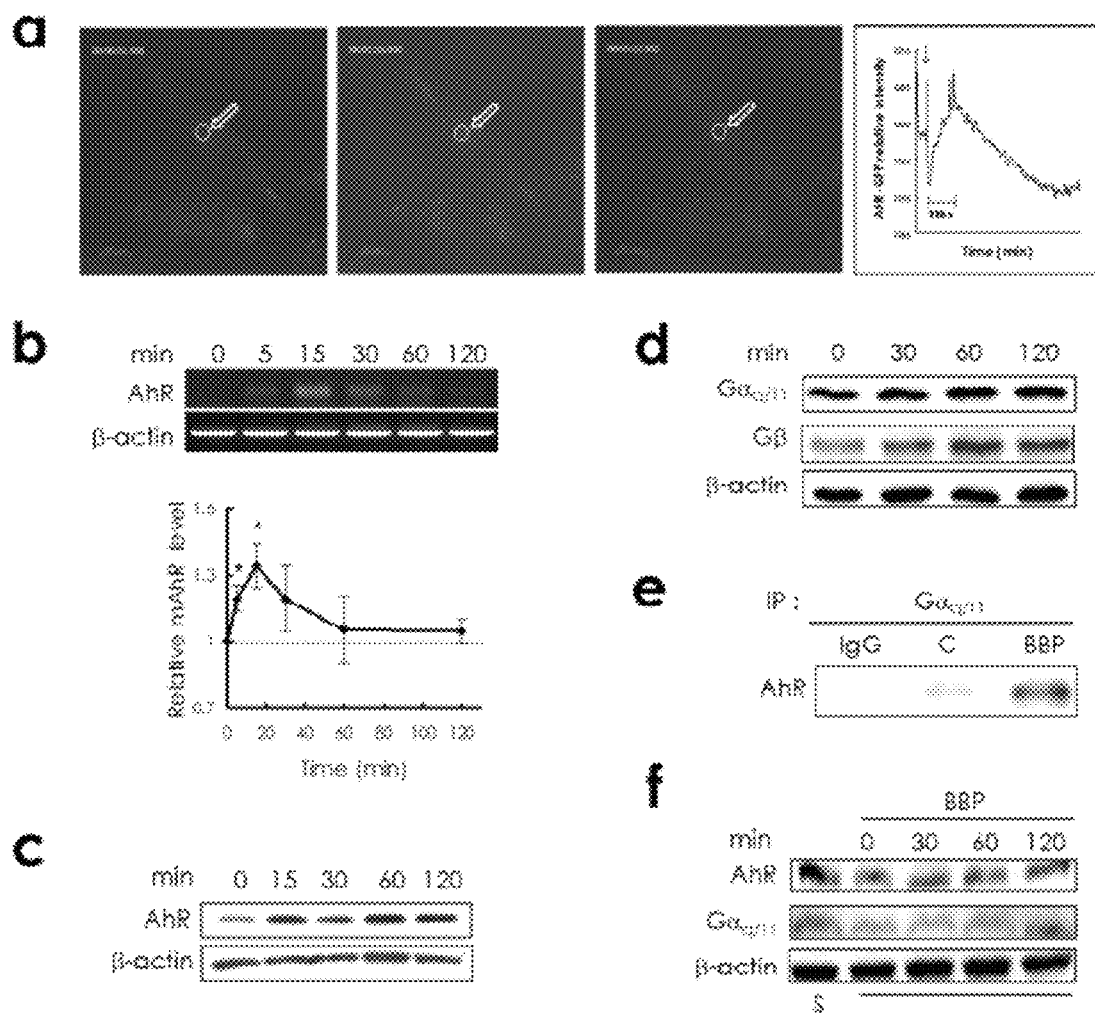
FIG. 14 illustrates the analysis of AhR as a signal molecule at the plasma membrane, including the activities of transfected pGFP-C1-AhR at the plasma membrane by introduction of BBP (1 µM) in Huh-7 cells. (14a) Images shown are the expressions of relative intensity of GFP-tagged AhR measured by TIRF microscopic analysis. The circle and arrow indicate the area measured over time: before stimulation (first panel), at peak (second panel) and at rest (third panel). The graph (fourth panel) shows that a peak value was found at around 2 min, with the arrow indicating time BBP was added. (14b) Quantitative RT-PCR analysis of memAhR in response to BBP shows a rapid elevation at 5 min peaking at 15 min followed by a gradual decline to a lower plateau levels at 2 h. Error bars indicate standard deviation. *, P<0.05, t-test (n=3). (14c) Analysis of Western blot assays reveals that BBP promoted AhR elevation at 15 min followed by a slight decrease at 30 min and a re-elevation at 60 min. (14d) Analysis of Western blot assays reveals that BBP induces the production of both $G\alpha_{q/11}$ and Gβ at 30 min. (14e) Immunoprecipitation (IP) assay indicates the interaction between AhR and $G_{\alpha q/11}$ after BBP stimulation, the letter C representing control. (14f) Knockout of AhR by siRNA demonstrates that BBP suppresses both AhR and $G\alpha_{q/11}$ expressions measured by Western blot analysis in Huh-7 cells, the letter S representing scrambled siRNA as negative control.

Immunofluorescence studies are considered important for the dynamic study of signal transduction through their ability to capture snapshots of molecular changes in the cell. Human hepatic Huh-7 cancer cells were pre-transfected with pGFP-C1-AhR by using LT1 transfection reagent (Mirus Bio LLC, WI) and total internal reflection fluorescence microscopy to selectively observe the molecular events in the cytoplasmic region immediately beneath the plasma membrane. When BBP was introduced, a rapid but transient recruitment and translocation of the GFP-tagged AhR occurred at the subcellular membrane regions, showing a fast elevation and peaking in 115 seconds followed by a gradual decrease in AhR that occurred over a few minutes (FIG. 14a). This fast dynamic movement of the memAhR at the subcellular membrane is reminiscent of the notion of soft-wired signal transduction. AhR has been found to serve an adaptive function through its regulation of biotransformation enzymes and change in localization within the cell, triggering its own activation.

Next, the association between BBP and AhR was examined by reverse transcription polymerase chain reaction (RT-PCR). BBP significantly induced mAhR expression in 5 min, peaking at 15 min and gradually returning to a slightly higher constitutive steady-state (FIG. 14b). Interestingly, Western blot analysis showed the BBP-induced elevation in AhR production at 15 min, slightly decreased production at 30 min, and a re-elevation at 1 h (FIG. 14c). The different patterns of AhR expression at these time-points found in these two assays can be explained by the differences between subcellular mRNAs activation and constitutive synthesis, supporting the notion of "cytoskeleton in mRNA transport". Therefore, it is likely that Huh-7 cells contain the structural machinery of mRNA needed for local protein translation in response to exogenous stimulation[21] and is called memAhR hereafter. The lower mRNA level probably represents the constitutive AhR activity in the maintenance of differential stability of cells. Upon ligand activation, heterotrimeric G proteins can dissociate into Gβγ dimers and Gα subunits, including $G_s$, $G_t$, $G_{q/11}$ and $G_{12/13}$, each performing different functions. BBP induced both of $Gα_{q/11}$ and Gβ production in 30 min (FIG. 14d). The elevation of $Gα_{q/11}$ was due to the direct interaction between memAhR and $Gα_{q/11}$ (FIG. 14e). These results were further confirmed by knockout of AhR using siRNA in cells (FIG. 14f). Clearly, these data indicate that by BBP stimulation, the GPCR was excited and led to the dissociation of heterotrimeric Gαβγ into Gα and Gβγ subunits, enabling $Gα_{q/11}$ to interact with their upstream activator, memAhR. Because AhR has been associated with $Gα_{13}$ and $Gα_{q/11}$ activities and in hepatoma cells, AhR activity can agitate cell fate processes, whereby a persistent expression of AhR can promote tumor cell growth. The experiments were directed toward the molecular events involved in $Gα_{q/11}$ signaling.

In one embodiment modulation of AhR activity can inhibit or decrease cell growth. In another embodiment modulation of AhR activity can kill a cell. In one embodiment modulation comprises down regulation of AhR protein activity in a cell. In another embodiment modulation comprises inhibition of AhR protein activity in a cell. In another embodiment modulation comprises inhibition of AhR protein association with a G protein in a cell. In another embodiment modulation comprises down regulation of AhR gene expression in a cell. In one the cell is a tumor cell. In one embodiment the tumor is a lung, breast, colon, brain, bone liver, prostate, stomach, esophageal, skin or leukemia tumor cell. In one embodiment the tumor is a solid tumor. In another embodiment the tumor is a liquid tumor. In one embodiment AhR activity is modulated with an AhR agonist. In another embodiment AhR activity is modulated with an AhR antagonist. In another embodiment AhR activity is modulated with a compound that has anti-estrogenic activity. In another embodiment AhR activity is modulated with a compound that has anti-androgenic activity.

In one embodiment the tumor cell is in a mammal. In another embodiment the tumor cell is in a human. In another embodiment a method for treating a tumor in human is provided by administering a compound to the human that inhibits or decreases the activity of an AhR protein in the tumor. In another embodiment a method for treating a tumor in human is provided by administering a compound to the human that inhibits or decreases the gene expression of a AhR protein in the tumor.

Figure 15:
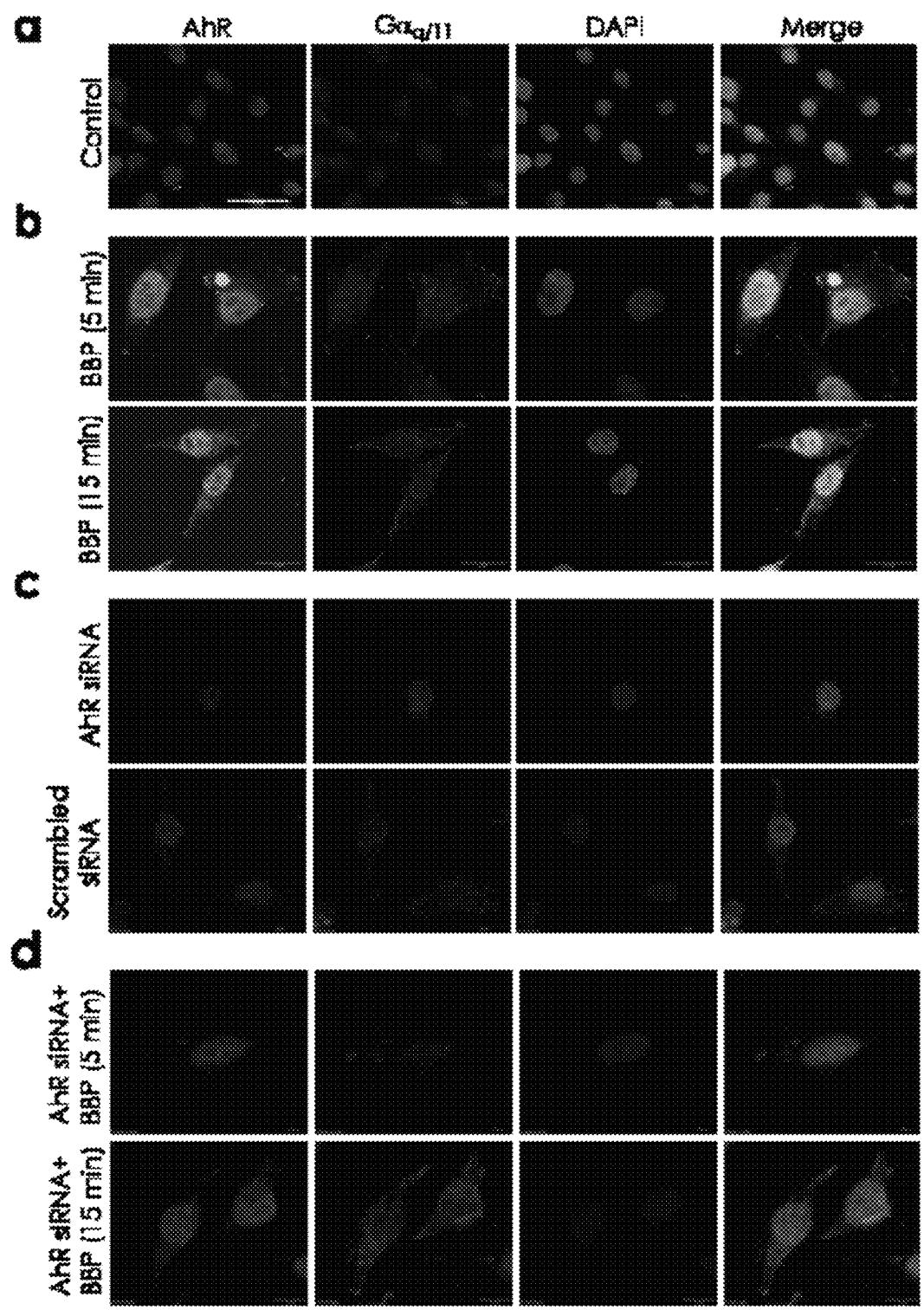
FIG. 15 illustrates results of dynamic immunofluorescence imaging. (15a) illustrates immunostaining of untreated control cells; AhR and $G\alpha_{q/11}$ expression observed mainly in the nucleus and weakly in the cytosol in Huh-7 cells; bar scale: 50 µm. (15b) Cells treated with BBP (1 µM) for 5 and 15 min each reveals a translocation of both AhR and $G\alpha_{q/11}$ from the nucleus to the cytosolic compartment. Immunostained $G\alpha_{q/11}$ accumulates specifically at the cell membrane at 15 min. (15c) Cells transfected with AhR siRNA greatly reduces AhR intensity in both cytosolic and nuclear compartments (upper panel), while transfected with scrambled siRNA does not change the immunostaining intensity (lower panel). (15d) BBP rescued intensities of both AhR and $G\alpha_{q/11}$ in cells with pre-transfected AhR siRNA after 15 min.

For confocal immunofluorescence imaging microscopy, cells were treated with BBP for 5 and 15 min each followed by immunofluorescence staining of both AhR and $Gα_{q/11}$. In the absence of BBP, less expression of both AhR and $Gα_{q/11}$ in the cytoplasm than in the nucleus was observed (FIG. 15a). In cells stimulated by BBP, a clear increase in expression of AhR in the nucleus and peri-nuclear regions at 5 min followed by an outward spreading of AhR was observed at 15 min (FIG. 15b, first column). These results indicate a constitutive AhR activity and cytosolic translocation. With respect to expression of $Gα_{q/11}$, it appeared to be stimulated in a similar way to that of AhR at 5 min (FIG. 15b, second column). However, $Gα_{q/11}$ had translocated from the cytosolic compartment towards the cell membrane at 15 min, supporting a maturation of GPCR-G protein complex capable of making a correct transportation to the cell membrane based on the ontogenetic viewpoint, though the exact mechanism is unclear. Subsequently, siRNA knockout of AhR suppressed the expression of nuclear AhR but not cytosolic AhR, which was confirmed by the knockout of AhR using scrambled siRNA (FIG. 15c). However, when BBP was added, AhR expression was increased in both nucleus and peri-nuclear regions at 5 min, reaching a homeostatic state by 15 min in the cytosol (FIG. 15d, first column). Notably, $Gα_{q/11}$ was repressed by AhR siRNA (FIG. 15d, second column), which was partially recovered by the addition of BBP at 5 min and totally recovered at 15 min, showing an apparent accumulation of $Gα_{q/11}$ at the cell membrane (FIG. 15d, second column). These results indicated that $Gα_{q/11}$ is a downstream effector of memAhR. The dynamic movements and constitutive activities of both AhR and $Gα_{q/11}$ further suggest a compensatory effect, involving their activation, translocation and maturation in the cell.

Figure 16:
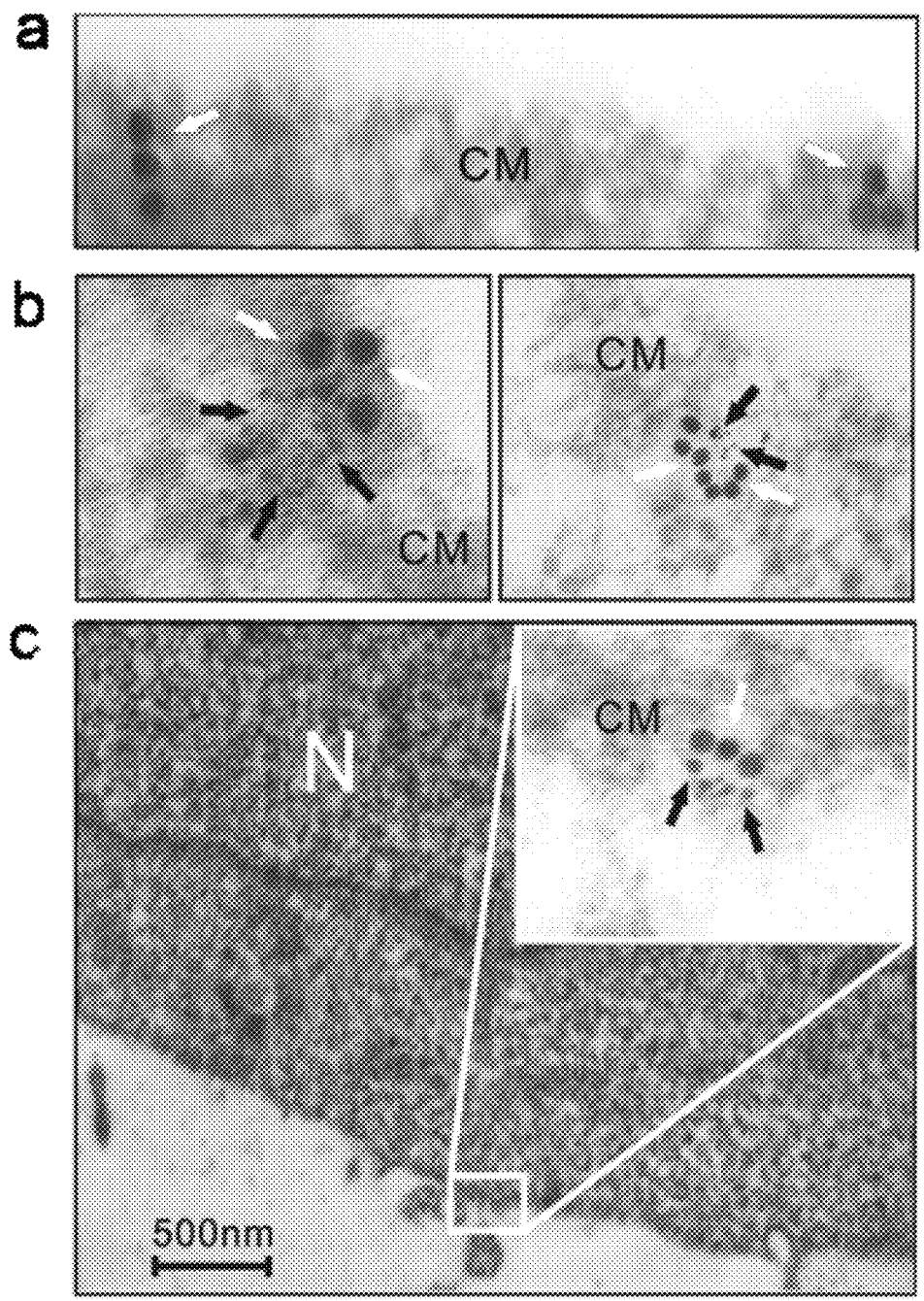
FIG. 16 illustrates the results of double immunogold transmission electron microscopic analysis. (16a) Immunogold-stained $G\alpha_{q/11}$ (white arrow) could exist as either single or double or triple in entity at the cell membrane in Huh-7 cells as control. (16b) At 20 min, BBP(1 µM)-treated cell showed an interaction of immunogold-tagged AhR particles (6 nm in size, black arrow) and immunogold-tagged $G\alpha_{q/11}$ particles (20 nm in size, white arrow), forming a complex, appearing as different entities: monomeric (not shown), dimeric (not shown), trimeric (left) and polymeric entities (right) at the plasma membrane. (16c) A trimeric complex of AhR and $G\alpha_{q/11}$ appeared at the cell membrane. CM: cell membrane, N: nucleus, and bar scale: 500 nm.

Because of the spatio-temporal dynamics, double immunogold transmission electron microscopy (IEM) was used to show interaction of memAhR at the plasma membrane. Cells were treated with BBP for 20 min and subjected to immunocytochemistry using specific primary antibodies and secondary antibodies of large gold particle-tagged $Gα_{q/11}$ (20 nm in size) and small gold particle-tagged AhR (6 nm in size). The samples were immediately embedded in LR White Resin (Ted Pella, Redding, Calif.) and prepared for IEM. In the absence of ligand, three separate immunogold-tagged $Gα_{q/11}$ entities were displayed, including single, double and triple clusters at the cell membrane (FIG. 16a), reflecting the existence of different entities of GPCR-G protein complex. Treating the cells with BBP, a number of small gold-tagged AhR adhered to the large gold-tagged $Gα_{q/11}$ was observed to form an AhR-$Gα_{q/11}$ complex at the cell membrane (FIG. 16b). In addition to the classical monomer and recently accepted dimers, the presence of polymeric GPCR-$Gα_{q/11}$ was observed at the cell membrane. This suggests a variety of conformational changes in GPCRs, including monomer, dimers and polymers (FIG. 16c). The AhR-$Gα_{q/11}$ complex was found mainly at the plasma membrane. There were few in the cytosolic, but none in the nuclear compartment where abundant AhR and $Gα_{q/11}$ existed independently. No such AhR-$Gα_{q/11}$ interaction was seen in the control cells. The data revealed that the clusters of memAhR and GPCRs-$Gα_{g/11}$ complex were not pre-coupled before ligand activation. The polymerization (either homo- or hetero-multimers) of GPCRs is meaningful because it is an effective mode for modulating the function, subcellular localization, and biophysical properties of the interacting molecules. It probably enables the creation of more spatial docking sites for the screening of exogenous ligands such as agonists and antagonists, or synergistic bindings at the cell surface. Alternatively, it provides a clue into one of the most puzzling aspects of biological impact; specifically, how polycyclic aromatic hydrocarbon compounds in the environment are related to toxic, metabolic and carcinogenic responses in cells.

Figure 17:
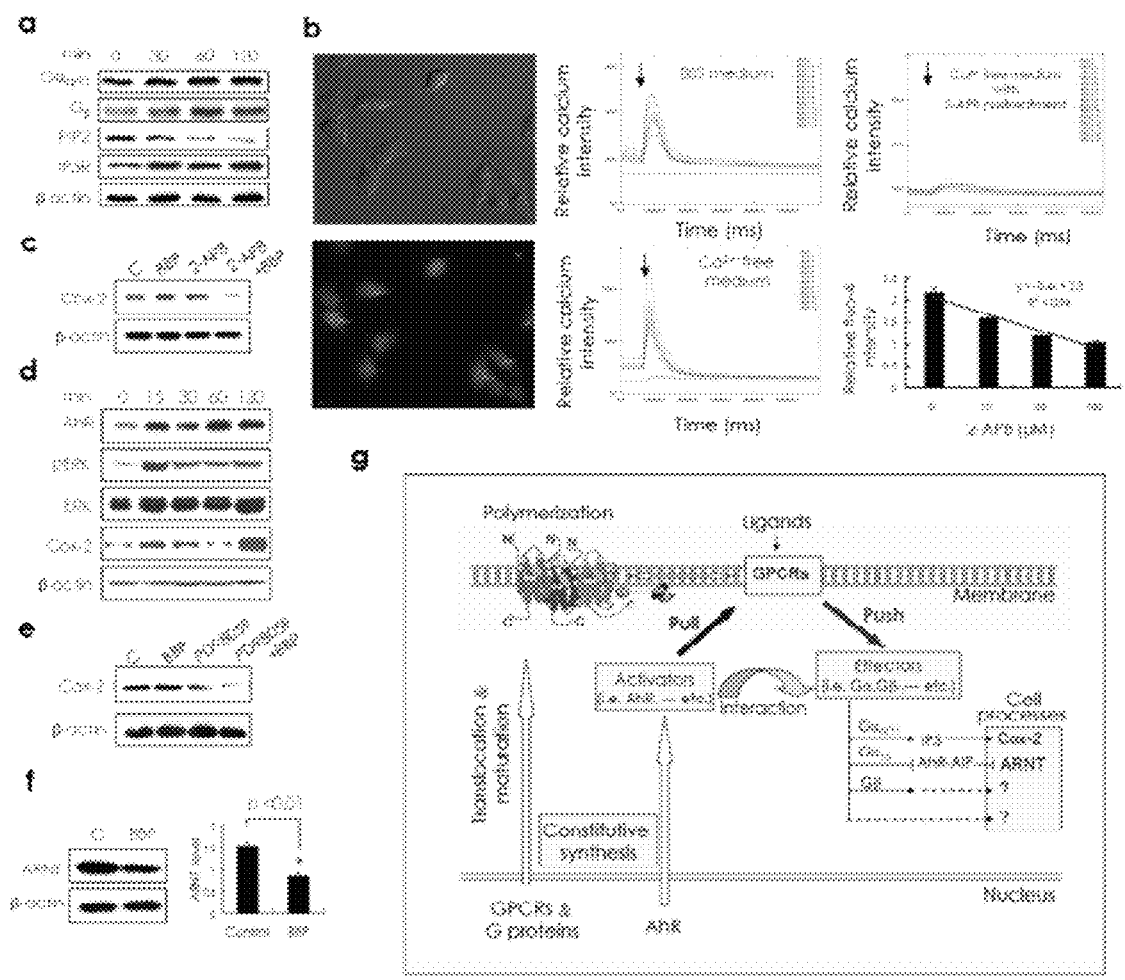
FIG. 17 illustrates the "pull and push" mechanism and biochemical processes. (17a) illustrates measurements of $G\alpha_{q/11}$ signaling cascades in response to BBP treatment in Huh-7 cells. Western blot analysis revealed that BBP (1 µM) triggered production of both $G\alpha_{q/11}$ and Gβ at 30 min. Activated $G\alpha q_{/11}$ led to decreases in PIP2, causing increased IP3R levels. (17b) illustrates the analysis of the responsiveness of immunofluorescent Fluo-4-labeled calcium in the Huh-7 cells. Shown are the unlabelled cells (left upper panel) and Fluo-4-labeled calcium (green, left lower panel). Also shown are the changes of relative calcium levels after BBP (1 µM) stimulation (arrow) in BSS medium (middle upper panel) and calcium free medium (middle lower panel). Cells cultured in the calcium free medium with pre-treated IP3R inhibitor 2-APB (100 µM, 1 h) (right upper panel) showed a reduction in calcium intensive (right upper panel), which occurred in a dose-response manner (y=−0.4x+2.5, $R^2$=0.94) (right lower panel). Error bars indicate the standard deviation of the mean (n=5). (17c) Results of Western blot analysis indicate that the BBP-induced COX-2 expression was inhibited by pretreatment with 2-APB (30 µM, 1 h), the letter C indicating control. (17d) illustrates results of Western blot analysis, indicating that BBP (1 µM) induced the overproduction of COX-2 via AhR/$Ca^{2+}$/ERK/COX-2 pathway. ERK1/2 was phosphorylated at 15 min and dephosphorylated at 30 min after BBP treatment. (17e) illustrates results of Western blot analysis, indicating that the BBP-induced COX-2 expression was inhibited by pretreatment with chemical PD98059 (20 µM, 1 h, Calciochem), the letter C indicating control. (17f) illustrates that ARNT levels were significantly inhibited by treatment with BBP (1 µM) measured overnight. Data represent the means±SD, n=3 and *: Student's t-test, p<0.01. (17g) illustrates a schematic representation of the "pull and push" mechanism underlying the ligand-induced nongenomic AhR signaling pathway via GPCRs-G protein signaling.

To study the biochemical processes of G protein signaling, it was verified that upon activation by BBP, memAhR can interact with $Gαq_{/11}$, as described previously. Subsequently, a decrease in phosphatidylinositol (PIP2) levels was observed resulting from the cleavage of PIP2 into two secondary messengers: diacylglycerol (DAG) and IP3 (FIG. 17a, first panel). IP3 is known to induce the release of intracellular calcium through its receptor IP3R at the endoplasmic reticulum (FIG. 17a, second panel). Because G protein activation is often accompanied by an influx of calcium ions, the origin of the BBP-elicited intracellular fluo-4-tagged $Ca^{2+}$ levels was examined by real-time live cell immunofluorescence imaging microscopy (FIG. 17b, middle upper). The cells were cultivated in calcium free medium and found the release of intracellular calcium (FIG. 17b, middle lower), indicating release from the internal calcium store. This result was further confirmed by adding IP3R blocker 2-APB, which was found to dose-dependently inhibit intracellular calcium levels (FIG. 17b, right column). An aberrant calcium release, however, can induce inflammatory responses[4] and tumorigenesis. Accordingly, BBP was observed to induce production of COX-2 in 15 min, which could be blocked by adding 2-APB (FIG. 17c), linking the increase in intracellular calcium with the activation of COX-2. Moreover, BBP induced phosphorylation of an extracellular signal-regulated protein kinase ERK and activation of COX-2 (FIG. 17d), which was blocked by chemical PD98059, a potent and selective noncompetitive inhibitor of the MAPK pathway (FIG. 17e), indicating that ERK is the upstream activator of COX-2. To this end, BBP was shown to induce the activation of COX-2 via the memAhR-activated $G\alpha_{q/11}$ signaling in molecular processes. This indicates the existence of a nongenomic AhR pathway because BBP significantly inhibited ARNT expression, a gene encoding AhR nuclear translocator protein (FIG. 17f). This inhibitory effect can be interpreted as the action of co-activated $G\alpha_{13}$ as described previously.

It is demonstrated that AhR can be a signal transducer in response to external signals, resulting in the excitation of GPCR-G protein signaling. It is proposed that the signal "pulls" the nearby cytosolic memAhR (as activator) to the cell membrane to bind and activate the dissociated $G\alpha_{q/11}$ (as effector), and "pushes" the downstream molecular cascades for functions in human hepatic Huh-7 cancer cells. This "pull and push" model, as illustrated in FIG. 17g, contributes greatly to the understanding of how the regulation of GPCR-G protein signaling is initiated and how the AhR-mediated signal transduction is controlled beyond the classical AhR pathway. The findings can further make an impact on the development of therapeutics focusing on the mechanistic regulation of GPCRs and G proteins.

Cell Culture and Chemicals.

Huh-7 cells were obtained from the National Health Research Institute, Taiwan and cultured in DMEM (Gibco) supplemented with 10% fetal bovine serum (Gibco), 1% penicillin (100 U/mL), streptomycin (10 μg), amphotericin-α (0.25 mg) and grown at 37° C. in 5% $CO_2$. Culture media included BSS containing $CaCl_2$ (2 mM), D-glucose (5.5 mM), NaCl (130 mM), KCl (5.4 mM), HEPES (20 mM, pH 7.4) and $MgSO_4$ (1 mM). Calcium free medium contained D-glucose (5.5 mM), NaCl (130 mM), KCl (5.4 mM), HEPES (20 mM, pH 7.4) and $MgSO_4$ (3 mM). Chemicals included were Fluo-4 (Invitrogen), Benzyl butyl phthalate (BBP, Sigma), 2-aminoethoxydiphenyl borate (2-APB, Sigma), ERK1/2 inhibitor: PD98059 (Calbiochem), 6-diamidino-2-phenylindole (DAPI, Sigma). Antibodies included were AhR (Santa Cruz), Cox-2 (Minipore), $G\alpha_{q/11}$ (sc-392) and Gβ (sc-378, Santa Cruz), β-actin (Sigma), p44/42 MAPK (Erk1/2) (Cell Signaling), Phospho-α44/42 MAPK (Cell Signaling), Horseradish peroxidase (HRP)-labeled anti-mouse and anti-rabbit secondary antibodies (Santa Cruz), Dye Light 488-conjugated secondary antibody (green color) and Dye Light 549-conjugated secondary antibody (red color) (Rockland).

hTS cells obtained from the preimplantation embryos in women with early tubal ectopic pregnancy were described previously. Adherent hTS cells were cultured in conditioned α-MEM containing 10 μg/ml bFGF (JRH, Biosciences, San Jose, Calif.), 10% FBS, and 1% penicillin-streptomycin at 37° C. in 5% $CO_2$. Cells were treated by RA (10 μM) for various time intervals depending on the experiments.

RNA isolation and RT-PCR. Huh-7 cells (3×105) were seeded into a 6-well dish and incubated for 24 h. Cells cultured serum-free medium overnight were treated with BBP (1 μM) for various time intervals. After BBP stimulation, cells were washed twice with PBS. Total RNAs were extracted by TRIzol methods (Invitrogen). RNA (2 μg) was used to synthesize cDNA by Reverse Transcription System (Promega). The c-DNAs were amplified by the specific primers. The primer pairs were designed as follows: AhR, forward 5'-TAC TCT GCC GCC CAA ACT GG-3' (SEQ ID NO: 49), reverse 5'-GCT CTG CAA CCT CCG ATT CC-3' (SEQ ID NO: 50); β-actin, forward 5'-CTC GCT GTC CAC CTT CCA-3' (SEQ ID NO: 51), reverse 5'-GCT GTC ACC TTC ACC GTTC-3' (SEQ ID NO: 52). PCR conditions were set at 95° C. for 5 min and 95° C. for 30 sec, 54° C. for 30 sec, 72° C. for 1 min followed by 72° C. for 10 min (36 cycles). The products were separated by 2% agarose gels and visualized by ethidium bromide.

Western Blotting Analysis.

Huh-7 cells (1×10⁶) were seeded into 10 cm dish and cultured overnight. The culture medium was changed to serum-free medium for another night. Cells were treated with BBP (1 μM) for various time intervals. For other studies, cells were pretreated with the chemical PD98059 (20 μM) or 2-APB (30 μM) for 1 h followed by treatment with BBP. Cells were then washed twice with ice-cold PBS and lysed by RIPA lysis buffer (Minipore). Protein concentration was measured by BCA protein assay kit (Thermo). Equal amounts of protein (30 μg protein) were resolved by 8% SDS-PAGE, transferred onto PVDF membrane, and blocked with 5% non-fat dry milk for 1 h at room temperature. After blocking, the membrane was incubated with the primary antibodies including AhR (1:1000), Cox-2 (1:1000), $G\alpha_{q/11}$ (1:100), Gβ (1:100), β-actin (1:5000), p44/42 MAP kinase (1:1000) or phospho-p44/42 MAP kinase (1:1000) overnight at 4° C. Cells were washed three times with PBST and then incubated with HRP conjugated secondary antibodies for 1 h at room temperature. After washing, the blot was visualized using an enhanced chemiluminescence kit (ECL) (Amersham).

ChIP.

By using ChIP kit (Upstate Biotechnology, Lake Placid, N.Y.), cells were serum-deprived for overnight and treated with RA (10 μM) for 4 hr. For assay, briefly, the lysate was sonicated on ice to shear the DNA. The crosslinked chromatin was incubated with protein G agarose plus anti-RNA polymerase II (positive control), or normal mouse IgG (negative control) or primary antibody indicated. After sequential treatments with 5M NaCl, RNase A, EDTA, Tris, and proteinase K, the DNA mixtures were obtained by spin filter and subjected for polymerase chain reaction (PCR).

Immunoprecipitation.

Huh-7 cells were serum-deprived overnight and treated with BBP (1 μM) for 30 min. After pre-cleaning with protein G-agarose (Minipore) for 30 min, specific antibody $G\alpha_{q/11}$ or rabbit IgG was added to culture which was again incubated overnight. After incubation with protein G-agarose for 2 h, the beads were washed three times with RIPA lysis buffer, boiled in sample buffer, resolved by 8% SDS-PAGE and subjected to AhR immunoblotting analysis.

Cells were serum-deprived overnight and treated with RA (10 μM) for 4 hr. The cells were lysed by RIPA lysis buffer (Millipore). The mixtures of lysate and protein A or protein G agarose (Minipore) were incubated with rocking at 4° C. for 2 hr. Specific primary antibody or rabbit IgG (control)

was added and incubated overnight. The immune protein complex was then captured on beads with either protein A or protein G. The antibody-bound proteins were precipitated by rocking for overnight. The immunoprecipitated proteins were washed with RIPA lysis buffer followed by analysis with SDS-PAGE and immunoblotting with another specific antibody to measure the interaction.

Immunofluorescence.

For immunocytochemistry, cells were fixed with 4% paraformaldehyde in PBS followed by permeabilization with 2% FBS/0.4% Triton X-100 in PBS (15 min). By 5% FBS blocking solution (2 hr) and rinsed three times, cells were incubated with specific primary antibody in PBS at 4° C. overnight. Appropriate FITC or PE or Texas Red conjugated secondary antibody was added for 1 hr followed by DAPI staining for nucleus (5 min) and subjected for microscopy.

Total Internal Reflection Fluorescence (TIRF) Microscopy.

Huh-7 cells were pre-transfected with pGFP-C1-AhR (a gift of H. Li) by using LT1 transfection reagent (Minis Bio LLC, Madison, Wis.) for 24 h. For TIRF microscopy, cells were cultured in serum-free medium on cover-slip overnight followed by stimulation by BBP (1 µM, Sigma). The dynamic activities of GFP-tagged AhR at the cell membrane were observed and analyzed by using Zeiss TIRF microscope with Axio Vision Rel. 4.8 software.

Real-Time Live Cell Imaging Microscopy.

Cells were pre-treated with Fluo-4 (1 µM), a $Ca^{2+}$-specific dye, in BSS buffer at 37° C. for 20 min before treatment with BBP (1 µM). Measurements of relative intracellular calcium intensity were performed by real-time cell imaging microscopy and analyzed by Cell-R software system (Olympus). Either calcium-free medium or an IP3R inhibitor 2-APB used at various concentrations was used to test the intracellular calcium responses in the cell culture.

Confocal Immunofluorescence Imaging Microscopy.

Cells with or without transfection by AhR siRNA were cultured and treated with BBP (1 µM) for 5 and 15 min each. After treatment with primary and secondary antibodies for AhR and $G\alpha_{q/11}$, cells were subjected to confocal immunofluorescence microscopy to analyze the dynamic movement in the cell compartments.

Double Immunogold Transmission Electron Microscopy.

Ultrathin sections of plastic embedded cells obtained by microwave fixation and processing[24] were pretreated with 5% sodium metaperiodate (10 min). The grids were incubated with an aliquot of IgG antibody against AhR or $G\alpha_{q/11}$ (C-19, sc-392, Santa Cruz) followed by probing with a secondary anti-mouse IgG gold particles (6 nm in size) or anti-rabbit IgG gold particles (20 nm in size), respectively. After washing, the sections were blocked by placing the grids on a drop of PBS with 1% ovalbumin (15 min). Sections were then stained with uranyl acetate and lead citrate and observed by transmission electron microscopy (Hitachi H-700 model, Japan).

All publications, patents, and patent applications mentioned in this specification are herein incorporated by reference to the same extent as if each individual publication, patent, or patent application was specifically and individually indicated to be incorporated by reference. Olanow, C. W. The scientific basis for the current treatment of Parkinson's disease. An. Rev. Med. 55, 41-60 (2004).

Freed, C. R. et al. Transplantation of embryonic dopamine neurons for severe Parkinson's disease. N. Engl. J. Med. 344, 710-719 (2001).

Lindvall, O. & Kokaia, Z. Stem cells for the treatment of neurological disorders. Nature 441, 1094-1096 (2006).

Kim, J. H. et al. Dopamine neurons derived from embryonic stem cells function in an animal model of Parkinson's disease. Nature 418, 50-56 (2002).

Bjorklund, L. M. et al. Embryonic stem cells develop into functional dopaminergic neurons after transplantation in a Parkinson rat model. Proc. Natl. Acad. Sci. USA 99, 2344-2349 (2002).

Reubinoff, B. E., Itsykson, P., Turetsky T, Pera M F, Reinhartz E, Itzik, A. & Ben-Hur, T. Neural progenitors from human embryonic stem cells. Nat. Biotechnol. 19, 1134-1140 (2001).

Roy, N. S., Cleren, C., Singh, S. K., Yang, L., Beal, M. F. & Goldman, S. A. Functional engraftment of human ES cell-derived dopaminergic neurons enriched by co culture with telomerase-immortalized midbrain astrocytes. Nat. Med. 12, 1259-1268 (2006).

Dunnett, S. B., Bjorklund A. & Lindvall, O. Cell therapy in Parkinson's disease: stop or go? Nat. Rev. Neurosci. 2, 365-369 (2001).

Parolini, O. et al. Concise review: Isolation and characterization of cells from human term placenta: outcome of the first international Workshop on Placenta Derived Stem Cells. Stem Cells 26, 300-311 (2008).

Ilancheran. S. & Moodley, Y. & Manuelpillai, U. Human fetal membranes: a source of stem cells for tissue regeneration and repair? Placenta 30, 2-10 (2009).

Surani, M. A., Hayashi, K. & Hajkova, P. Genetic and epigenetic regulators of pluripotency. Cell 128, 747-762 (2007).

Yamanaka, Y., Ralston, A., Stephenson, R. O., & Rossant, J. Cell and molecular regulation of the mouse blastocyst. Dev. Dyn. 235, 2301-2314 (2006).

Chen, H. F., Chao, K. H., Shew, J. Y., Yang, Y. S. & Ho, H. N. Expression of leukemia inhibitory factor and its receptor is not altered in the decidua and chorionic villi of human anembryonic pregnancy. Hum. Reprod. 19, 1647-1654 (2004).

Wånggren, K., Lalitkumar, P. G., Hambiliki, F., Ståbi, B., Gemzell-Danielsson, K. & Stavreus-Evers, A. Leukaemia inhibitory factor receptor and gp130 in the human fallopian tube and endometrium before and after mifepristone treatment and in the human preimplantation embryo. Mol. Hum. Reprod. 13, 391-397 (2007).

Keltz, M., Attar, E., Buradagunta, S., Olive, D., Kliman, H. & Arici, A. Modulation of leukemia inhibitory factor gene expression and protein biosynthesis in the human fallopian tube. Am. J. Obs. Gyn. 175, 1611-1619 (1996).

Smith, A. G., Heath, J. K., Donaldson, D. D., Wong, G. G., Moreau, J., Stahl, M. & Rogers, D. Inhibition of pluripotential embryonic stem cell differentiation by purified polypeptides. Nature 336, 688-690 (1998).

Williams, R. L., Hilton, D. J., Pease, S., Willson, T. A., Stewart, C. L., Gearing, D. P., Wagner, E. F., Metcalf, D., Nicola, N. A. & Gough, N. M. Myeloid leukemia inhibitory factor maintains the developmental potential of embryonic stem cells. Nature 336, 684-687 (1988).

Chambers, I., Colby, D., Robertson, M., Nichols, J., Lee, S., Tweedie, S. & Smith, A. Functional expression cloning of Nanog, a pluripotency sustaining factor in embryonic stem cells. Cell 113, 643-655 (2003).

Boiani, L. A. & Scholer, H. R. Regulatory networks in embryo-derived pluripotent stem cell. Nat. Rev. Mol. Cell. Biol. 6, 872-884 (2005).

Adjaye, J. et al. Primary differentiation in the human blastocyst: comparative molecular portraits of inner cell mass and trophectoderm cells. Stem Cells 23, 1514-1525 (2005).

He, S., Pant, D., Schiffmacher, A., Meece, A. & Keefer, C. L. Lymphoid enhancer factor 1-mediated Wnt signaling promotes the initiation of trophoblast lineage differentiation in mouse embryonic stem cells. Stem Cells 26, 842-849 (2008).

Maden, M. Retinoic acid in the development, regeneration and maintenance of the nervous system. Nat. Rev. Neurosci. 8, 755-765 (2007).

Wichterle, H., Lieberam, I., Porter, J. A. & Jessell, T. M. Directed differentiation of embryonic stem cells into motor neurons. Cell. 110, 385-397 (2002).

Li, X. J., Du, Z. W., Zarnowska, E. D., Pankratz, M., Hansen, L. O., Pearce, R. A. & Zhang, S. C. Specification of motorneurons from human embryonic stem cells. Nat. Biotechnol. 23, 215-221 (2005).

Zhang, X., Klueber, K. M., Guo, Z., Cai, J., Lu, C., Winstead, W. I., Qiu, M. & Roisen, F. J. Induction of neuronal differentiation of adult human olfactory neuroepithelial-derived progenitors. Brain Res. 1073-1074, 109-119 (2006).

Jacobs, S., Lie, D. C., DeCicco, K. L., Shi, Y., DeLuca, L. M., Gage, F. H. & Evans, R. M. Retinoic acid is required early during adult neurogenesis in the dentate gyrus. Proc. Natl. Acad. Sci. USA. 103, 3902-3907 (2006).

Tsai, Y.-L., Tseng, S.-F., Chang, S.-H., Lin, C.-C. & Teng, S.-C. Involvement of replicative polymerases, Tel1p, Mec1p, Cdc13p, and the Ku complex in telomere-telomere recombination. Mol. Cell. Biol. 22, 5679-5687 (2002).

Niwa, H., Toyooka, Y., Shimosato, D., Strumpf, D., Takahashi, K., Yagi, R. & Rossant, J. Interaction between Oct3/4 and Cdx2 determines trophectoderm differentiation. Cell 123, 917-929 (2005).

Cavaleri, F. & Scholer, H. R. (2003). Nanog: a new recruit to the embryonic stem cell orchestra. Cell 113, 551-552 (2003).

Martín-Ibáñez, R, Urbán, N., Sergent-Tanguy, S., Pineda, J. R., Garrido-Clua, N., Alberch, J. & Canals, J. M. Interplay of leukemia inhibitory factor and retinoic acid on neural differentiation of mouse embryonic stem cells. J. Neuron. Res. 85, 2686-2710 (2007).

Bain, G., Kitchens, D., Yao, M., Huettner, J. E. & Gottlieb, D. I. Embryonic stem cells express neuronal properties in vitro. Dev. Biol. 168, 342-357 (1995).

Tropepe, V., Hitoshi, S., Sirard, C., Mak, T. W., Rossant, J. & van der Kooy, D. Direct neural fate specification from embryonic stem cells: a primitive mammalian neural stem cell stage acquired through a default mechanism. Neuron 30, 65-78 (2001).

Smith, C. R., Chan, H. S. & deSa, D. J. Placental involvement in congenital neuroblastoma. J. Clin. Pathol. 34, 785-789 (1981).

Panicker, M. M. & Rao, M. Stem cells and neurogenesis. in Stem Cell Biology (eds Msrshak, D. R., Gardner, R. L. & Gottlieb, D.) 399-438 (Cold Spring Harbor Laboratory Press, Cold Spring Harbor, N.Y., 2001).

Yan, J., Tanaka, S., Oda, M., Makino, T., Ohgane, J. & Shiota, K. Retinoic acid promotes differentiation of trophoblast stem cells to a giant cell fate. Dev. Biol. 235, 422-432 (2001).

Chen, L. & Khillan, J. S. Promotion of feeder-independent self-renewal of embryonic stem cells by retinol (vitamin A). Stem Cells 26, 1858-1864 (2008).

Li, L. et al. Human Embryonic Stem Cells Possess Immune-Privileged Properties. Stem Cells 22, 448-456 (2004).

Swijnenburg, R. J. et al. Immunosuppresive therapy mitigates immunological rejection of human embryonic stem cell xenografts. Proc. Natl. Acad. Sci. USA. 105, 12991-12996 (2008).

Bavaresco, L., Bernardi, A., Braganhol, E., Cappellari, A. R., Rockenbach, L., Farias, P. F., Wink, M. R., Delgado-Cañedo, A. & Battastini, A. M. The role of ecto-5′-nucleotidase/CD73 in glioma cell line proliferation. Mol. Cell. Biochem. 319, 61-68 (2008).

Napoli, I. & Neumann, H. Microglial clearance function in health and disease. Neuroscience 158, 1030-1038 (2009).

Song, H., Stevens, C. F. & Gage, F. H. Astroglia induce neurogenesis from adult neural stem cells. Nature 417, 39-44 (2002).

Annerén, C., Cowan, C. A & Melton, D. A. The Src family of tyrosine kinases is important for embryonic stem cell self-renewal. J. Biol. Chem. 279, 590-598 (2004).

Torres, J. & Watt, F. M. Nanog maintains pluripotency of mouse embryonic stem cells by inhibiting NFkappaB and cooperating with Stat3. Nat. Cell Biol. 10, 194-201 (2008).

Myers, R., L., Ray, S. K., Eldridge, R., Chotani, M. A., Chiu, I-M. Functional characterization of the brain-specific FGF-1 promoter, FGF-1B. J. Biol. Chem. 270, 8257-8266 (1995).

Wu, R. M., Murphy, D. L. & Chiueh, C. C. Suppression of hydroxyl radical formation and protection of nigral neurons by 1-deprenyl (Selegiline). Ann. N.Y. Acad. Sci. 786, 379-389 (1996).

Götz, M. Glial cells generate neurons—master control within CNS regions: developmental perspectives on neural stem cells. Neuroscientist 9, 379-97 (2003).

Singh, S. K., Hawkins, C., Clarke, I. D., Squire, J. A., Bayani, J., Hide, T., Henkelman, R. M., Cusimano, M. D. & Dirks, P. B. Identification of human brain tumour initiating cells. Nature 432, 396-401 (2004).

Zhu, Q. F., Ma, J., Yu, L. I. & Yuan, C. G. Grafted neural stem cells migrate to substantia nigra and improve behavior in Parkinsonian rats. Neurosci. Lett. 462, 213-218 (2009).

Lindvall O, Kokaia Z. & Martinez-Serrano A. Stem cell therapy for human neurodegenerative disorders-how to make it work. Nat. Med. 10 (Suppl), S42-50 (2004).

Wagner, J. et al. Induction of a midbrain dopaminergic phenotype in Nurr1-overexpressing neural stem cells by type 1 astrocytes. Nat. Biotechnol. 17, 653-659 (1999).

While some embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. An isolated human neural stem cell produced from an isolated human trophoblastic stem cell, wherein the isolated human neural stem cell expresses Cdx2, Nanog, Ngn3, RARβ, RXRα, RXRβ, RALDH-2, and RALDH-3 proteins, and wherein the isolated human neural stem cell has low levels of expression or an absence of expression of CD33 or CD133 cell surface proteins as compared to the isolated human trophoblastic stem cell.

* * * * *

SEQUENCE LISTING

<160> NUMBER OF SEQ ID NOS: 52

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatctgccg ctttgagg                                                 18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgagggttt ctgctttgc                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatcggcggc tccatcctg                                                19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gactcgtcat actcctgctt gc                                            22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtgtacacgg accaccagcg                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtggctgct gctgctgttg                                               20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
tccactacca agagacaggc tt                                             22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 8
tcaagctgtg ttgcacccaa                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
ggaggagaac aagcggacgc                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
cgcgcttctt gtcctcctcc                                                20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
ctaggcatca cctgtgccat acc                                            23

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12
cagtgaccag ttcatcagat tcatc                                          25

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgcagccacc gagacaccat                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggcaagggc aagggcaaga                                              20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catagagacc gtcacagcaa g                                            21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgaacacca cactgacaac c                                            21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acggcgagaa gggagaagtt g                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggggtccag ggttgccatt g                                            21

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
agcgccccct cgtgtatg                                                    18

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
tgtccccggc aacttcagc                                                   19

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cggcggcgga actgctacga a                                                21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ggggcggggg cggaaactt                                                   19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gctgttatgg gtgaaactct g                                                21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ataaggtgga gatgcaggct c                                                21

<210> SEQ ID NO 25

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggtcacccaa gcaacaaagt                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctcctgcgt tcaagtcatc                                                   20

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctcgcgctac tctctctctt tctgg                                             25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcttacatgt ctcgatccca cttaa                                             25

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtggggcgcc ccaggcacca                                                   20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctccttaatg tcacgcacga tttc                                              24

<210> SEQ ID NO 31
<211> LENGTH: 26
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggaaaggctt cccctcagg gaaagg                                         26

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aagaacatgt gtaagctgcg gccc                                          24

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgtacacgg accaccagcg                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggtggctgct gctgctgttg                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agccaagtga aaaccaggac                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tttcctctcc tttgctctgc                                               20

<210> SEQ ID NO 37
<211> LENGTH: 19
<212> TYPE: DNA

<213> ORGANISM: Artificial Sequence
<220> FEATURE:
<223> OTHER INFORMATION: Description of Artificial Sequence: Synthetic primer

<400> SEQUENCE: 37
ctcagcctcc agcagatgc                                                    19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
aggcatccct ggtggtagg                                                    19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ggccactgcg cgctactcc                                                    19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ggctcctggg ccgaactgc                                                    19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
cctggtggcg ctctcgttg                                                    19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gcaggctgtc gcgggtgtc                                                    19

<210> SEQ ID NO 43
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 43
caccgtggcc gtgaagatg                                                    19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gggctcggag gtattctcg                                                    19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgctggaccc gggagaagc                                                    19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctccggcgtc gggtcaagg                                                    19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgtgtacctt ggcacctcc                                                    19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccttacccga ggtgtcagg                                                    19

<210> SEQ ID NO 49
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 49
tactctgccg cccaaactgg                                                  20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gctctgcaac ctccgattcc                                                  20

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctcgctgtcc accttcca                                                    18

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctgtcacct tcaccgttc                                                   19
```